(12) United States Patent
Hou et al.

(10) Patent No.: US 9,567,297 B2
(45) Date of Patent: Feb. 14, 2017

(54) METHOD FOR SYNTHESIZING OF THIOESTERS BY USING COMPOUND AS CATALYST

(71) Applicant: National Central University, Taoyuan (TW)

(72) Inventors: Duen-Ren Hou, Taipei (TW); Sharada Prasanna Swain, Bhirang Village (IN)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 14/885,863

(22) Filed: Oct. 16, 2015

(65) Prior Publication Data

US 2016/0340303 A1   Nov. 24, 2016

(30) Foreign Application Priority Data

May 22, 2015   (TW) .............................. 104116575 A

(51) Int. Cl.
| | | |
|---|---|---|
| *C07C 327/32* | (2006.01) | |
| *C07C 335/32* | (2006.01) | |
| *C07C 327/26* | (2006.01) | |
| *B01J 31/02* | (2006.01) | |

(52) U.S. Cl.
CPC .......... *C07C 327/32* (2013.01); *B01J 31/0222* (2013.01); *B01J 31/0237* (2013.01); *B01J 31/0271* (2013.01); *C07C 327/26* (2013.01); *C07C 335/32* (2013.01); *B01J 2231/32* (2013.01)

(58) Field of Classification Search
CPC .......................... C07C 327/32; B01J 31/0222
See application file for complete search history.

(56) References Cited

U.S. PATENT DOCUMENTS 2,752,373 A * 6/1956 Acker ................... C07C 323/00
                                                        549/39

OTHER PUBLICATIONS

Office Action of corresponding TW application, published on Apr. 7, 2016.
Olga V. Serdyuk, Christina M. Heckel and Svetlana B. Tsogoeva; "Bifunctional primary amine-thioureas in asymmetric organocatalysis"; Organic & Biomolecular Chemistry; Aug. 21, 2013; pp. 7051-7071; vol. 11; RSCPublishing.

* cited by examiner

*Primary Examiner* — Golam M M Shameem
(74) *Attorney, Agent, or Firm* — Wang Law Firm, Inc.

(57) ABSTRACT

A method for synthesizing of thioesters by using a compound as a catalyst is disclosed. The compound is represented by formula I below:

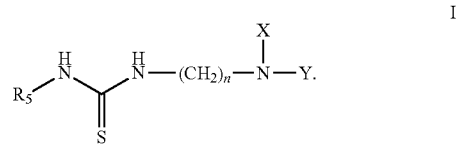

In formula I, $R^5$ represents H, a substituted or unsubstituted alkyl, a substituted or unsubstituted aryl, or a substituted or unsubstituted heteroaryl; X and Y each independently represents one of H, $C_{1-10}$ alkyl, $C_{5-10}$ aryl, $C_{1-10}$ alkyl alcohol, thiohydroxy, carbonyl, sulfonyl, sulfamoyl, carbamoyl, $C_{1-10}$ alkoxycarbonyl, $C_{1-10}$ alkoxycarbamoyl, $C_{1-10}$ alkylamino, $C_{1-10}$ alkylsulfonyl, $C_{1-10}$ haloalkylsulfonyl, ureido, amido, and $C_{1-10}$ alkoxylcarbamoyl; and n is 0, 1, 2, 3, 4 or 5.

4 Claims, 44 Drawing Sheets

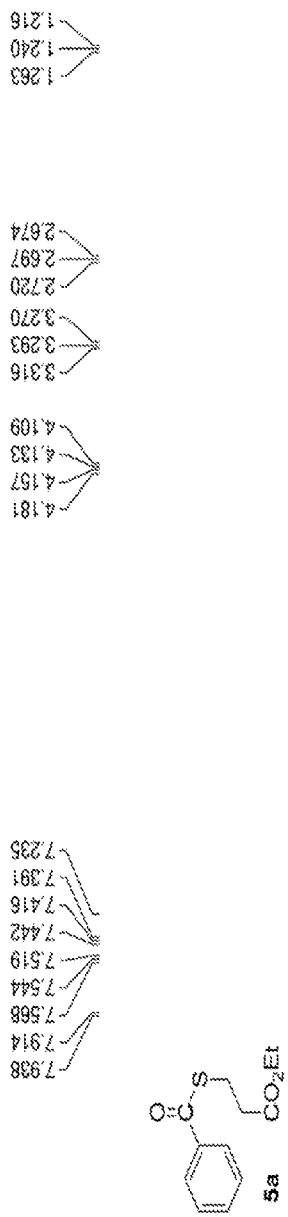
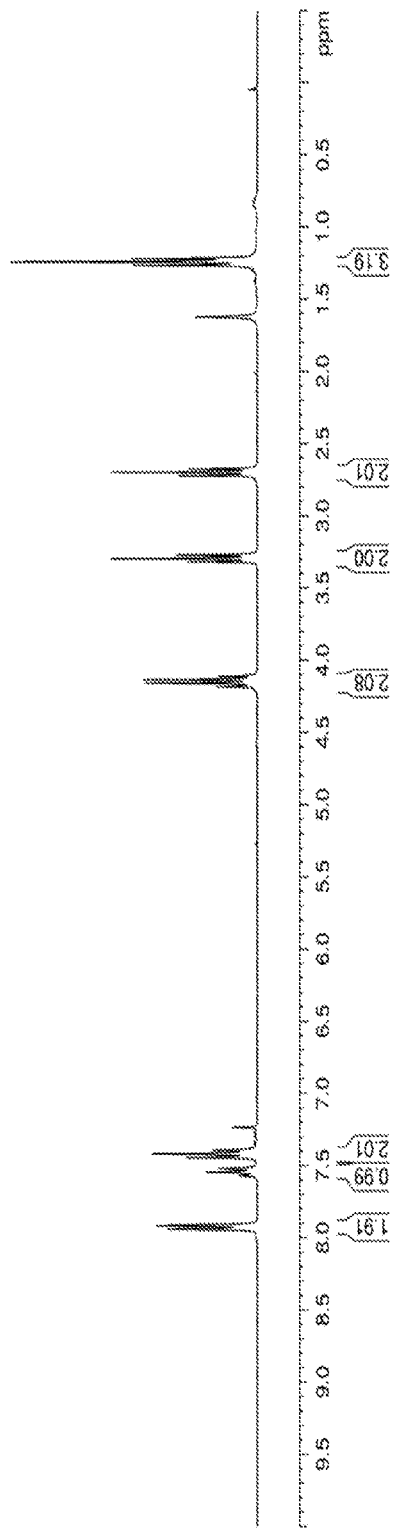
Fig. 3
1H NMR (300 MHz CDCl₃)

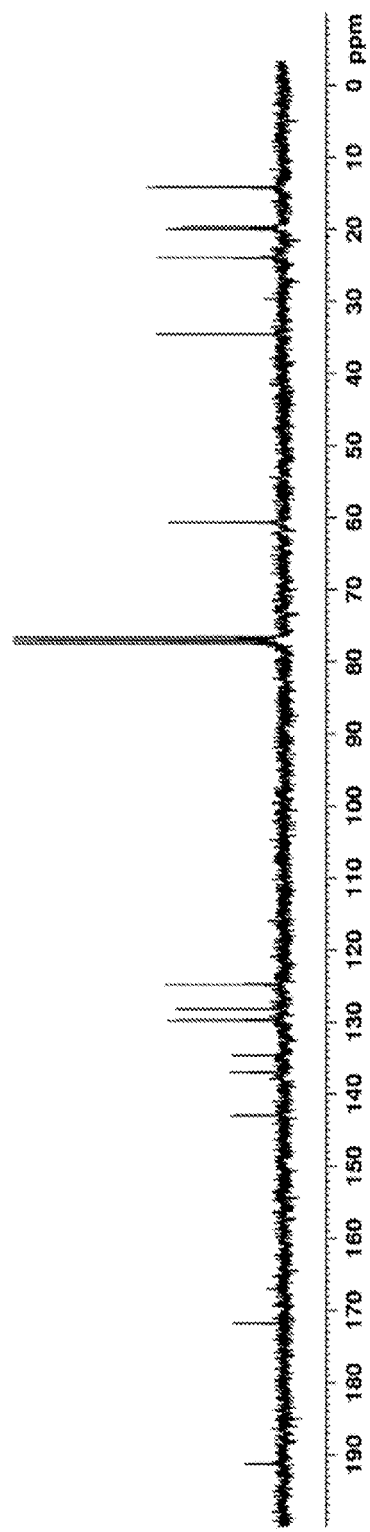
Fig. 8

1H NMR (300 MHz CDCl₃)

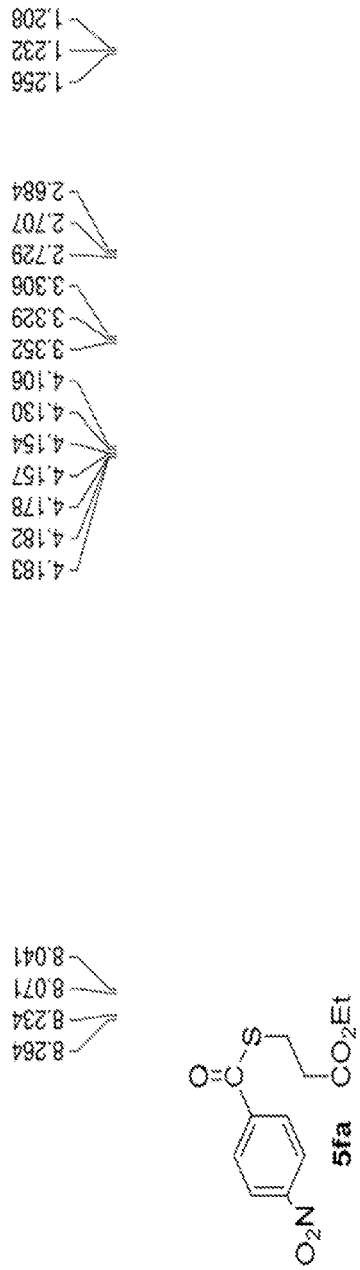
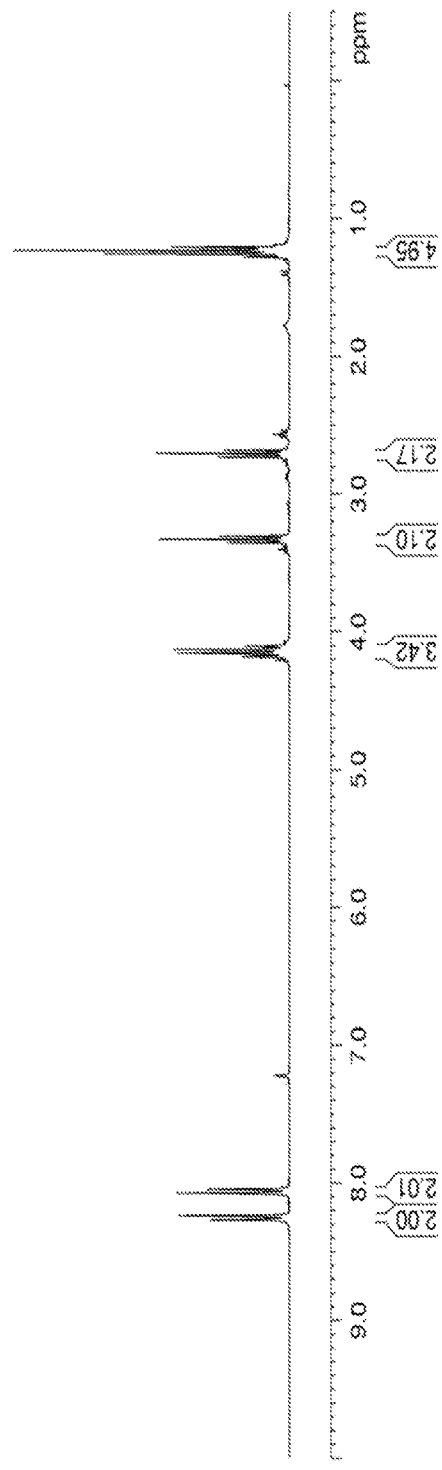
Fig. 13

1H NMR (300 MHz CDCl3)

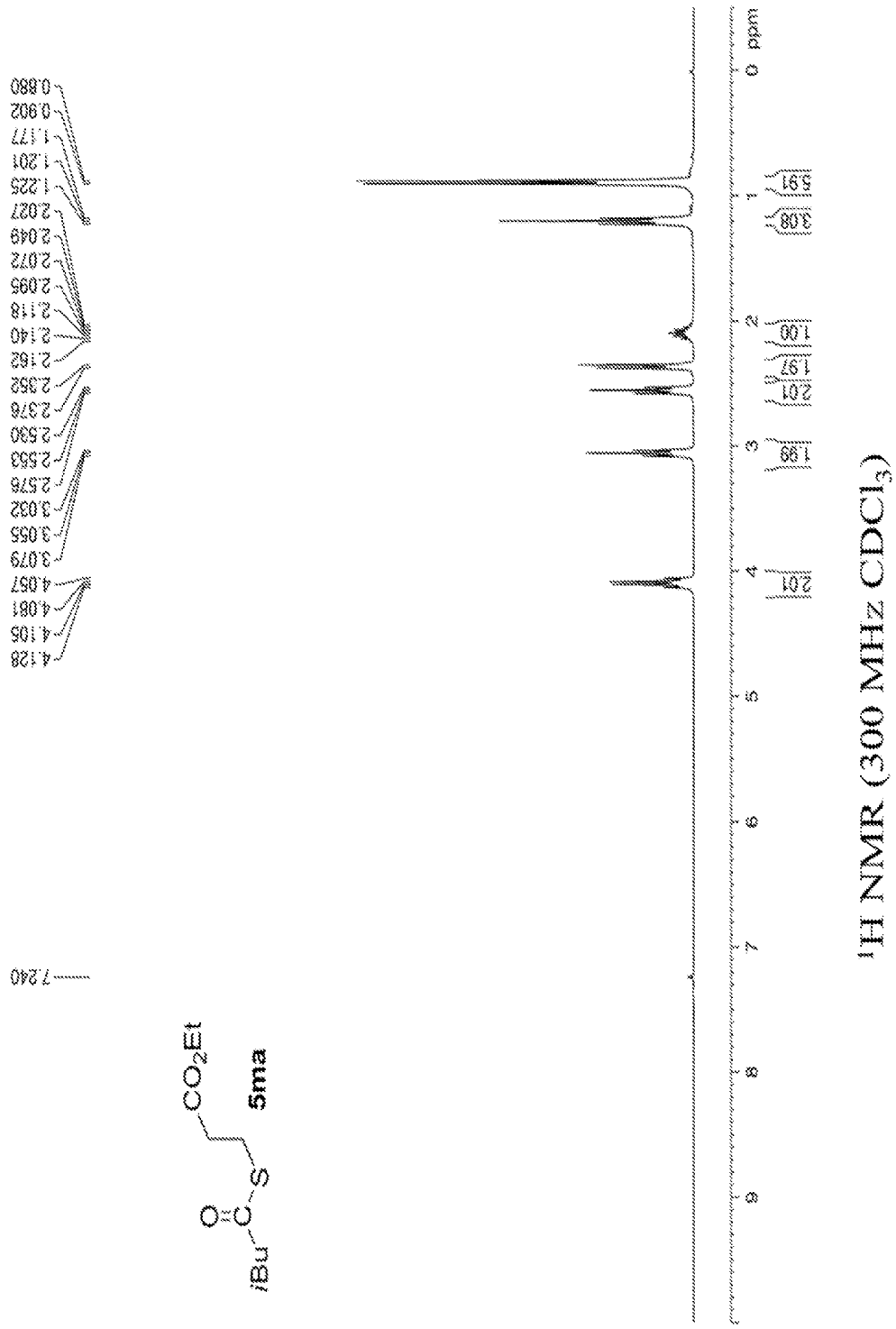
Fig. 27

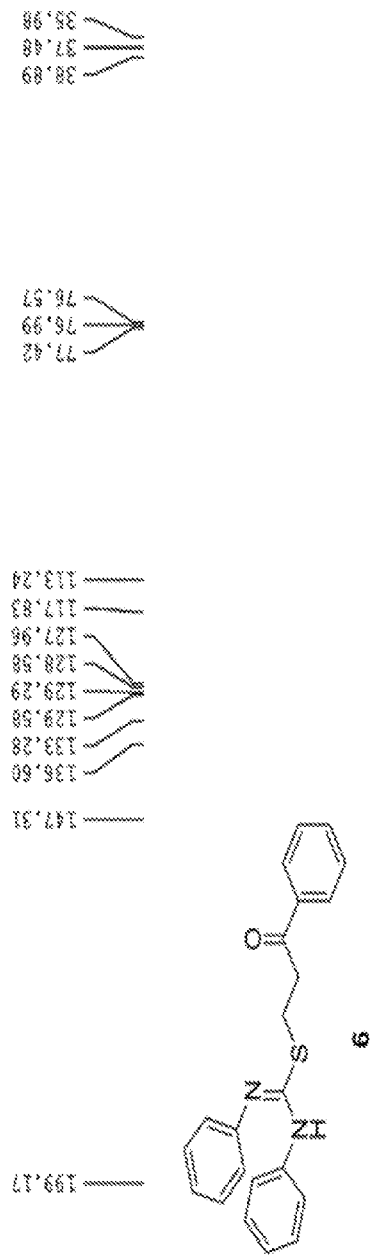
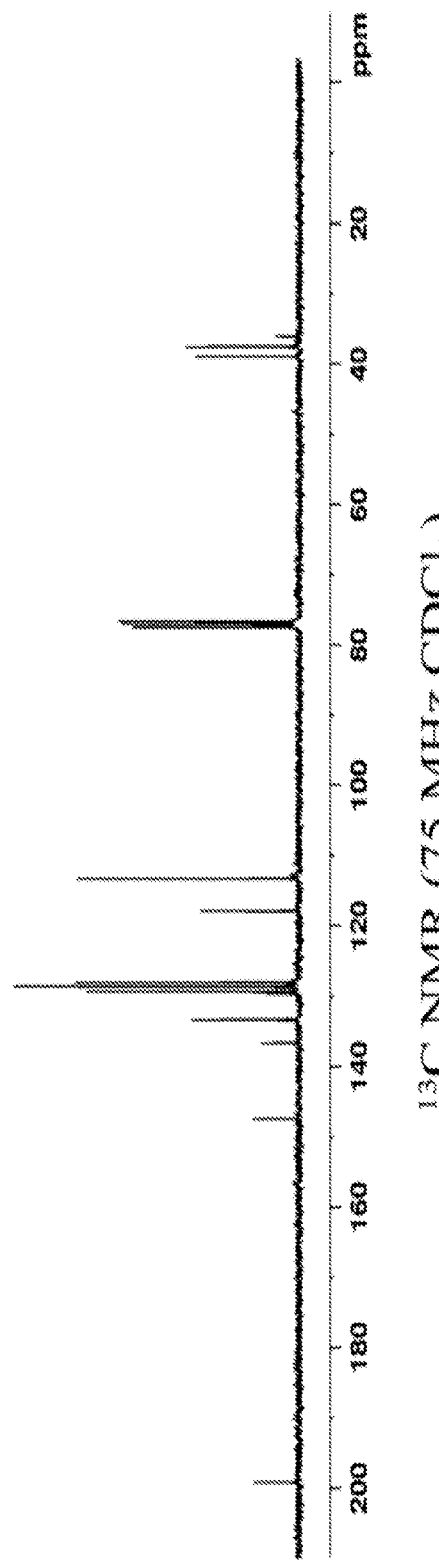
Fig. 30

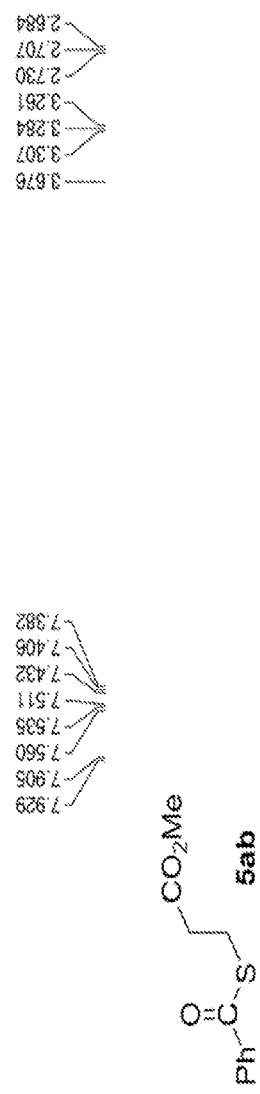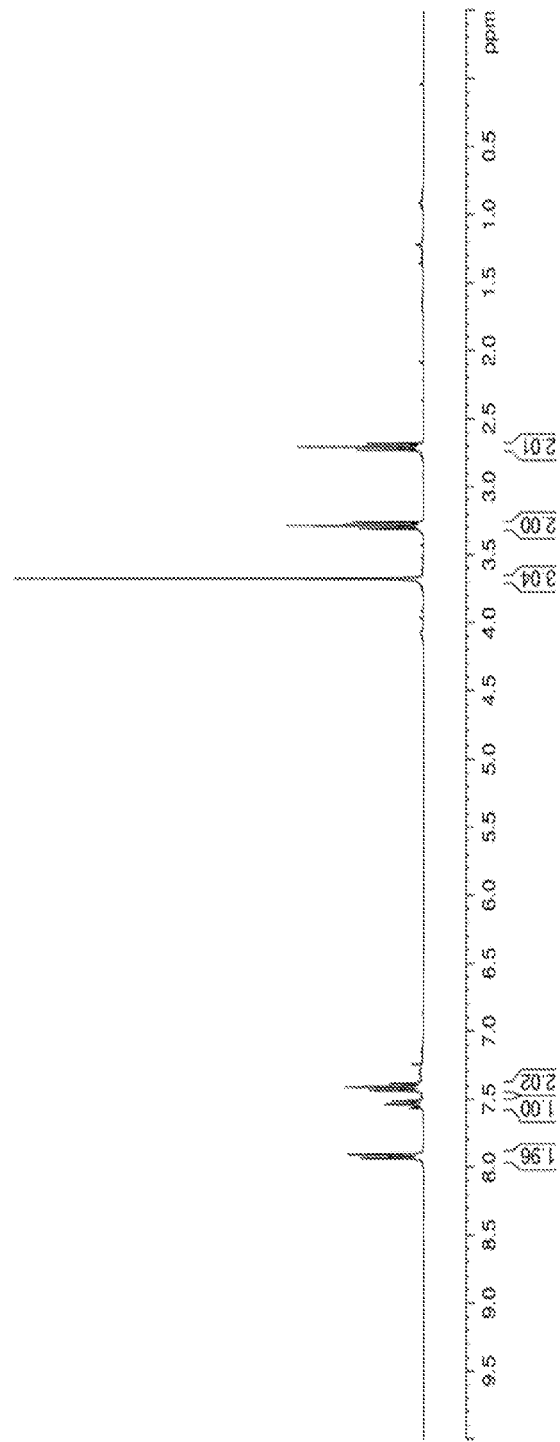
Fig. 31

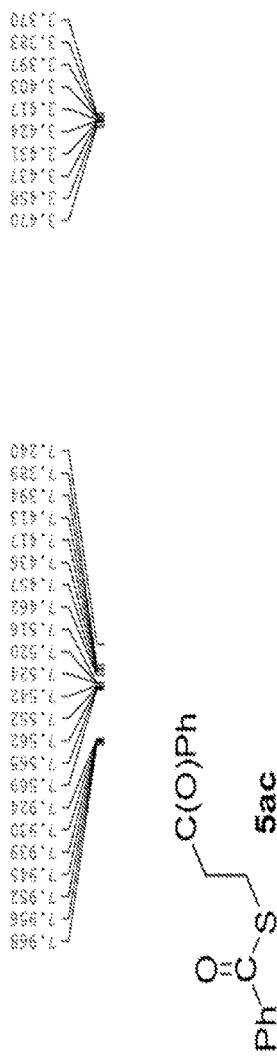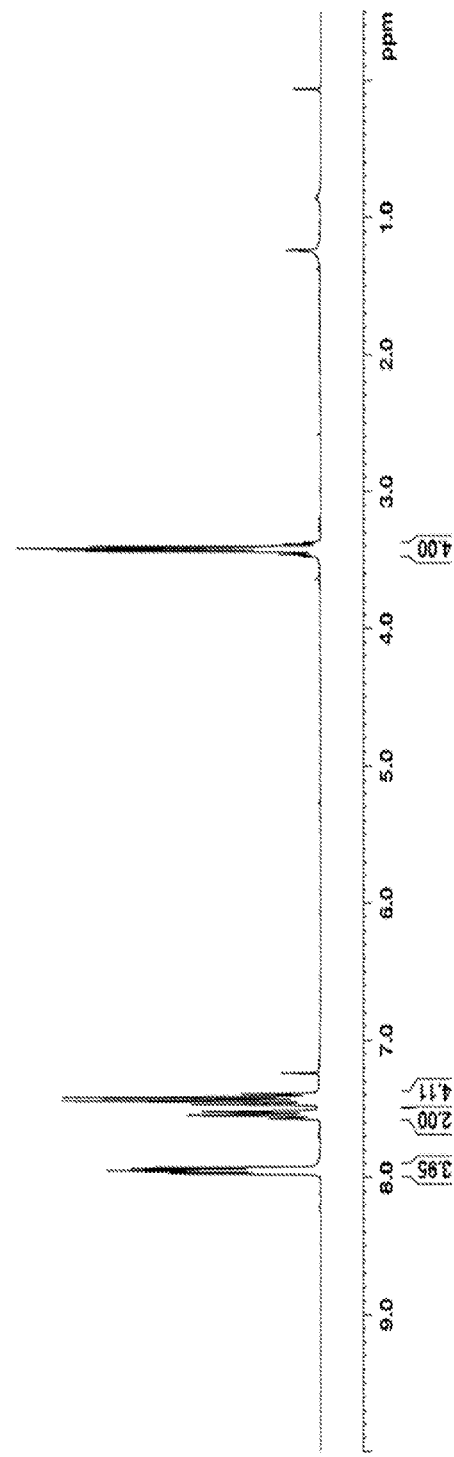
Fig. 33
1H NMR (300 MHz CDCl3)

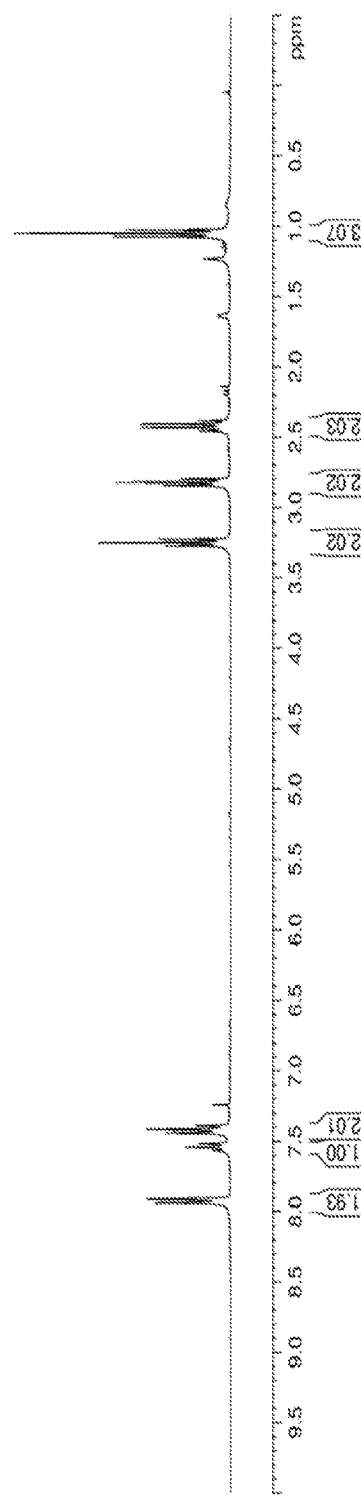
Fig. 35

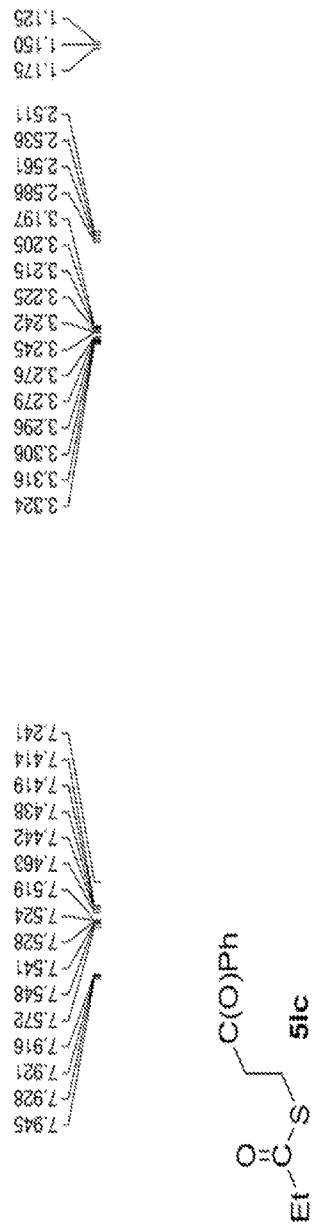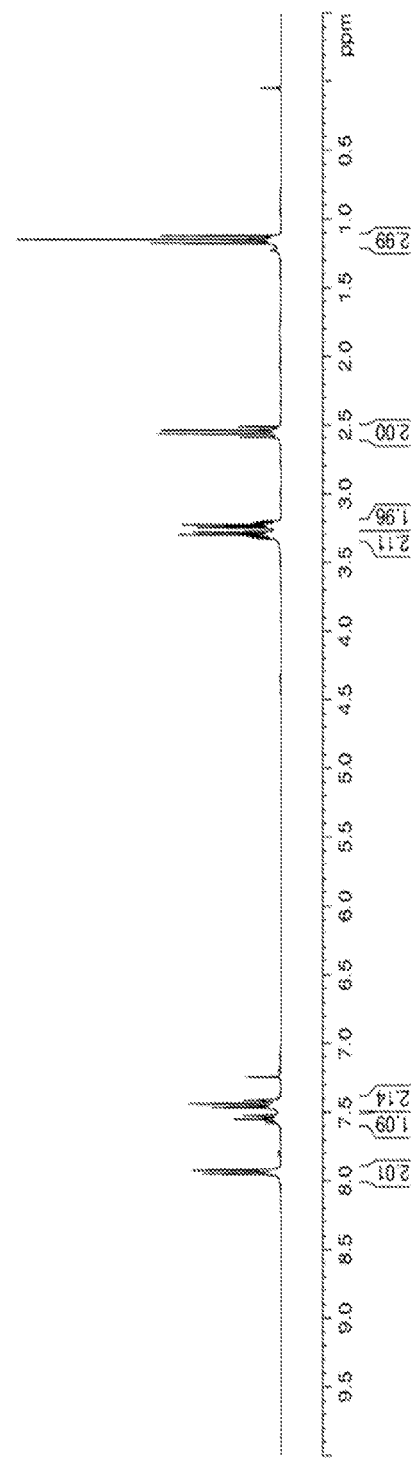
Fig. 39
$^1$H NMR (300 MHz CDCl$_3$)

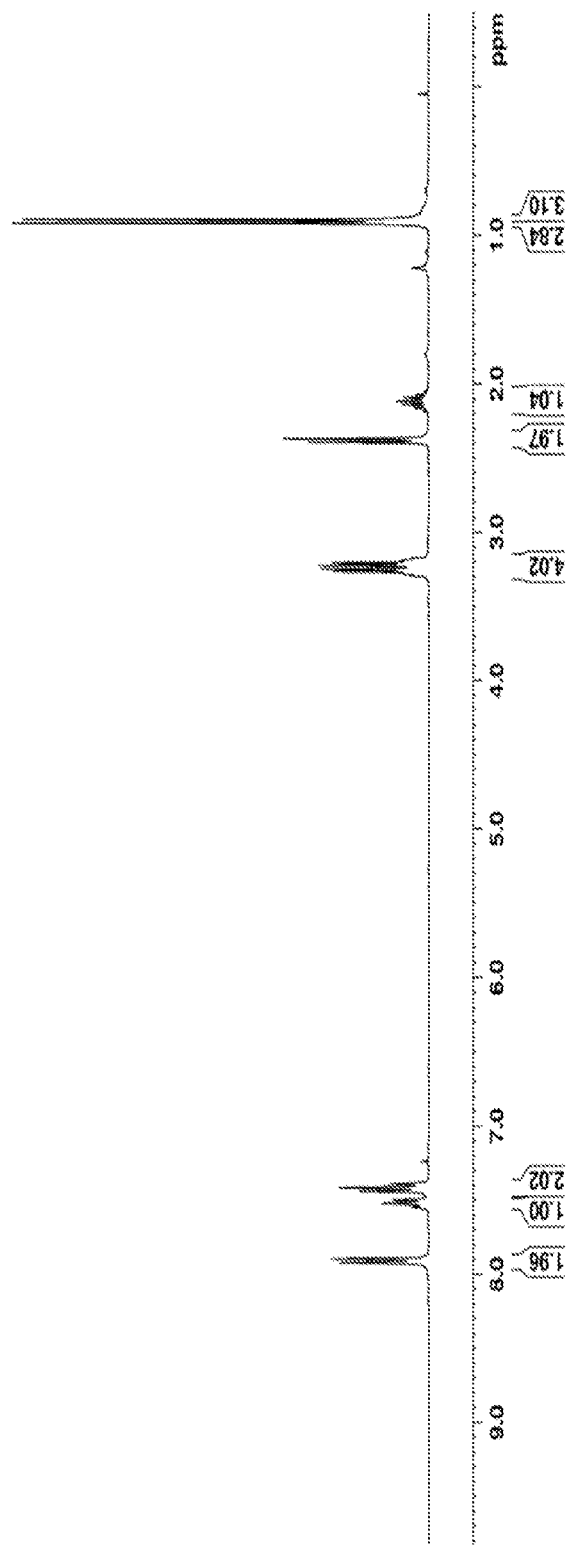
Fig. 41
1H NMR (300 MHz CDCl3)

METHOD FOR SYNTHESIZING OF THIOESTERS BY USING COMPOUND AS CATALYST

FIELD

This application claims priority to and the benefit of Taiwan Patent Application No. 104116575, filed on May 22, 2015, in the Taiwan Intellectual Property Office, the entire content of which is incorporated herein by reference.

A method for synthesizing of thioesters is disclosed, and more particularly, a method for synthesizing of thioesters by using a compound as a catalyst is disclosed.

BACKGROUND

The thioesters are chemical substances formed by covalently bonding a sulfur atom to a acyl group, which is provided with a general formula as follows:

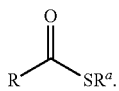

The thioesters are abundantly present in natural compounds, and are intermediate products during the hydrolysis or synthesis of ATP. The thioesters are required for forming all the ester bonds (including lipids). These substances are involved in the intracellular synthesis of a variety of materials, including peptides, fatty acids, steroids, terpenes, porphyrins, etc. The thioesters are also building blocks useful for organic synthesis and chemical synthesis of proteins. For example, the thioesters may be used to synthesize the thioesters with more complex structure, multi-substituted alkenes, thioethers, thiophene compounds and to react with amine compounds. The thioesters are also used as activated carboxylic acids and as acyl transfer agents for various nucleophiles.

Due to the unique structure of the thioesters, some thioesters possess biological activities and medicinal potential. For example, compound A as follows is an anti-inflammatory corticosteroid drug and compound B as follows may be used to treat Parkinson's disease.

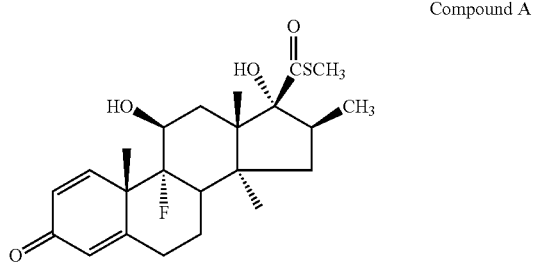

Compound A

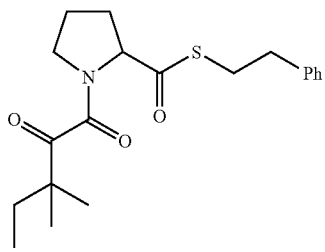

Compound B

Currently, the method in preparation of thioesters includes: (1) an esterification reaction between a carboxylic acid and a thiol; (2) a catalyzed transesterification reaction between a β-ketoester and a thiol; (3) a nucleophilic reaction between a cyclopropane derivative and a thiophenol; (4) carbonylation of allyl alcohol, propargyl alcohol, or diene and thiophenol; (5) carbonylation of a thioether. All of the methods mentioned above involve using a thiol, a thioether, or a thiophenol with a pungent smell.

In addition to the methods mentioned above, there is also a method for synthesizing of thioesters by using a thiourea instead of a thiol, a thioether, or a thiophenol with a pungent smell. The reaction scheme of the method is shown below. However, in addition to a thiourea, acyl halides, and organic halide, a surfactant and a base, such as $K_2CO_3$, NaOH, and the like, are further required for the method to obtain a thioester in higher yields.

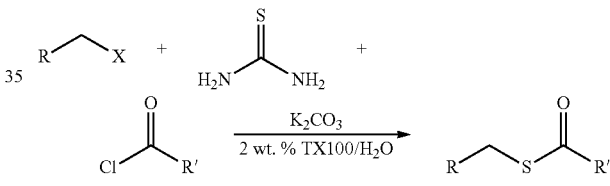

Compared to the method mentioned above, the present invention provides a method for synthesizing of thioesters by a thiourea without a pungent smell, and free of activating agent.

SUMMARY

In view of the above problems, it is a primary object of the present invention to provide a use of a compound as a catalyst and a method for synthesizing of thioesters. Compared to the conventional methods, the present invention provides a method for synthesizing of thioesters by using a catalyst, without activating the carboxylic acids. On top of that, the provided method is a one-pot synthesis under mild conditions while free of activating agent and base.

According to an aspect of the present invention, there is provided a method of synthesizing thioester, using a compound as a catalyst. The compound is represented by Formula (A) below:

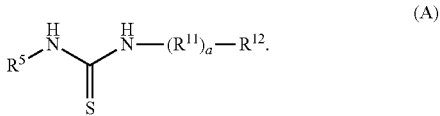

wherein, in Formula (A), $R^5$ may represent H, a substituted or unsubstituted alkyl, a substituted or unsubstituted aryl, or a substituted or unsubstituted heteroaryl; $R^{11}$ may be independently selected from a substituted or unsubstituted $C_1$-$C_{60}$ alkylene, a substituted or unsubstituted $C_3$-$C_{10}$ cycloalkylene, a substituted or unsubstituted $C_2$-$C_{10}$ heterocycloalkylene, a substituted or unsubstituted $C_2$-$C_{60}$ alkenylene, a substituted or unsubstituted $C_3$-$C_{10}$ cycloalkenylene, a substituted or unsubstituted $C_2$-$C_{10}$ heterocycloalkenylene, a substituted or unsubstituted $C_3$-$C_{10}$ cycloalkylene, a substituted or unsubstituted $C_6$-$C_{60}$ arylene, a substituted or unsubstituted $C_2$-$C_{60}$ heteroarylene, a substituted or unsubstituted divalent non-aromatic condensed polycyclic, a substituted or unsubstituted divalent non-aromatic condensed heteropolycyclic, —COO—, —O—, —(C=O)—, —N=N—, C=N—, —N—, —N($Q_{11}$)($Q_{12}$)-, —S—, —S($Q_{13}$)($Q_{14}$)-, —S(=O)—, or —S(=O)$_2$— ($Q_{11}$ to $Q_{14}$ may be each independently a hydrogen, a deuterium, —F, —Cl, —Br, —I, a hydroxyl, a cyano, a nitro, an amino, an amidino, a hydrazine, a hydrazone, a carboxylic acid or a salt thereof, a sulfonic acid group or a salt thereof, a phosphoric acid group or a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_2$-$C_{10}$ heterocycloalkenyl, a $C_6$-$C_{60}$ aryl, a $C_1$-$C_{60}$ heteroaryl, a monovalent non-aromatic condensed polycyclic group, or a monovalent non-aromatic condensed heteropolycyclic group); $R^{12}$ may be independently selected from a halogen atom, a hydroxyl, a cyano, a nitro, a thiohydroxy, an amino, a carbonyl, a carbamoyl, a sulfamoyl, a substituted or unsubstituted $C_{1-20}$ alkyl, a substituted or unsubstituted $C_2$-$C_{20}$ alkenyl, a substituted or unsubstituted $C_2$-$C_{20}$ alkynyl, a substituted or unsubstituted $C_1$-$C_{20}$ alkoxy, a substituted or unsubstituted $C_{1-20}$ alkyl alcohol, a substituted or unsubstituted $C_{1-20}$ haloalkyl, a substituted or unsubstituted $C_{1-20}$ alkylthio, a substituted or unsubstituted $C_{1-20}$ haloalkylthio, a substituted or unsubstituted $C_{1-4}$ alkylamino, a substituted or unsubstituted $C_{1-20}$ alkylamido, a substituted or unsubstituted $C_{1-20}$ alkylsulfonyl, a substituted or unsubstituted $C_{1-20}$ haloalkylsulfonyl, a substituted or unsubstituted $C_{1-20}$ alkoxycarbonyl, a substituted or unsubstituted $C_{1-20}$ alkylcarbamoyl, a substituted or unsubstituted $C_{6-10}$ aryl, a substituted or unsubstituted $C_{4-9}$ cycloalkyl, a substituted or unsubstituted $C_{4-9}$ heteroaryl, and a substituted or unsubstituted $C_{4-9}$ heterocycloalkyl; and a may be an integer selected from 0 to 10.

The compound represented by Formula (A) may be represented by Formula I below:

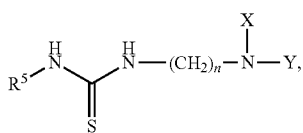

I wherein, in Formula I, $R^5$ may represent H, a substituted or unsubstituted alkyl, a substituted or unsubstituted aryl, or a substituted or unsubstituted heteroaryl; X and Y each independently may represent one of H, $C_{1-10}$ alkyl, $C_{6-10}$ aryl, $C_{1-10}$ alkyl alcohol, thiohydroxy, carbonyl, sulfonyl, sulfamoyl, carbamoyl, $C_{1-10}$ alkoxycarbonyl, $C_{1-10}$ alkoxycarbamoyl, $C_{1-10}$ alkylamino, $C_{1-10}$ alkylsulfonyl, $C_{1-10}$ haloalkylsulfonyl, ureido, amido, and $C_{1-10}$ alkoxylcarbamoyl; and n may be 0, 1, 2, 3, 4 or 5.

One or more substituents of the substituted alkyl, the substituted aryl, the substituted heteroaryl, the substituted $C_1$-$C_{60}$ alkylene, the substituted $C_3$-$C_{10}$ cycloalkylene, the substituted $C_2$-$C_{10}$ heterocycloalkylene, the substituted $C_2$-$C_{60}$ alkenylene, the substituted $C_3$-$C_{10}$ cycloalkenylene, the substituted $C_2$-$C_{10}$ heterocycloalkenylene, the substituted $C_3$-$C_{10}$ cycloalkylene, the substituted $C_6$-$C_{60}$ arylene, the substituted $C_2$-$C_{60}$ heteroarylene, the substituted divalent non-aromatic condensed polycyclic group, the substituted divalent non-aromatic condensed heteropolycyclic group, the substituted $C_2$-$C_{20}$ alkenyl, the substituted $C_2$-$C_{20}$ alkynyl, the substituted $C_1$-$C_{20}$ alkoxy, the substituted $C_{1-20}$ alkyl alcohol, the substituted $C_{1-20}$ haloalkyl, the substituted $C_{1-20}$ alkylthio, the substituted $C_{1-20}$ haloalkylthio, the substituted $C_{1-4}$ alkylamino, the substituted $C_{1-20}$ alkylamido, the substituted $C_{1-20}$ alkylsulfonyl, the substituted $C_{1-20}$ haloalkylsulfonyl, the substituted $C_{1-20}$ alkoxycarbonyl, the substituted $C_{1-20}$ alkylcarbamoyl, the substituted $C_{4-9}$ cycloalkyl, and the substituted $C_{4-9}$ heterocycloalkyl may be selected from the group consisting of:

a halogen atom, a hydroxyl, a cyano, a nitro, a thiohydroxy, an amino, a carbonyl, a carbamoyl, a sulfamoyl, a $C_{1-20}$ alkyl, a $C_2$-$C_{20}$ alkenyl, a $C_2$-$C_{20}$ alkynyl, a $C_1$-$C_{20}$ alkoxy, $C_{1-20}$ alkyl alcohol, $C_{1-20}$ haloalkyl, $C_{1-20}$ haloalkylthio, $C_{1-4}$ alkylamino, $C_{1-20}$ alkylamido, $C_{1-20}$ alkylsulfonyl, $C_{1-20}$ haloalkylsulfonyl, $C_{1-20}$ alkoxycarbonyl, $C_{1-20}$ alkylcarbamoyl, $C_{6-10}$ aryl, $C_{4-9}$ cycloalkyl, $C_{4-9}$ heteroaryl, and $C_{4-9}$ heterocycloalkyl.

$R^5$ in Formula I may represent a substituted or unsubstituted phenyl, a substituted or unsubstituted thienyl, or a substituted or unsubstituted pyridinyl; One of X and Y may be H and another may be a $C_{1-10}$ alkyl; and n may be 2.

$R^5$ in Formula I may represent a phenyl, One of X and Y may be H and another may be methyl; and n may be 2.

The method may include Reaction Scheme 1 shown below:

Reaction Scheme 1

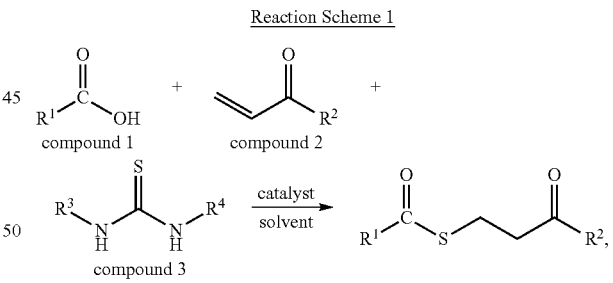

wherein $R^1$, $R^2$, $R^3$, and $R^4$ may be one group selected from the group consisting of H, a substituted or unsubstituted alkyl, a substituted or unsubstituted alkoxy, a substituted or unsubstituted aryl, or a substituted or unsubstituted heteroaryl, wherein the catalyst in Reaction Scheme 1 may be a compound represented by Formula I.

One or more substituents of the substituted alkyl, the substituted alkoxy, the substituted aryl, and the substituted heteroaryl may be selected from the group consisting of:

a halogen atom, a hydroxyl, a cyano, a nitro, a thiohydroxy, an amino, a carbonyl, a carbamoyl, a sulfamoyl, a $C_{1-20}$ alkyl, a $C_2$-$C_{20}$ alkenyl, a $C_2$-$C_{20}$ alkynyl, a $C_1$-$C_{20}$ alkoxy, $C_{1-20}$ alkyl alcohol, $C_{1-20}$ haloalkyl, $C_{1-20}$ haloalkylthio, $C_{1-4}$ alkylamino, $C_{1-20}$ alkylamido, $C_{1-20}$ alkylsulfonyl, $C_{1-20}$ haloalkylsulfonyl, $C_{1-20}$ alkoxycarbonyl, $C_{1-20}$ alkylcarbamoyl, $C_{6-10}$ aryl, $C_{4-9}$ cycloalkyl, $C_{4-9}$ heteroaryl, and $C_{4-9}$ heterocycloalkyl.

$R^1$ may represent a substituted or unsubstituted alkyl or a substituted or unsubstituted aryl; $R^2$ may represent a substituted or unsubstituted alkyl, a substituted or unsubstituted alkoxy, or a substituted or unsubstituted aryl; and $R^3$ and $R^4$ may represent a substituted or unsubstituted alkyl or a substituted or unsubstituted aryl.

The molar ratio of compound 1:compound 2:compound 3:catalyst is 1-1.5:1-1.5:1-1.5:0.1-0.5.

The solvent used in Reaction Scheme 1 may be a polar aprotic solvent.

The polar aprotic solvent may include one selected from the group consisting of $CH_2Cl_2$, toluene, dimethylformamide (DMF), tetrahydrofuran (THF) and methanol (MeOH) or any combination thereof.

The method may include Reaction Scheme 2 shown below:

Reaction Scheme 2

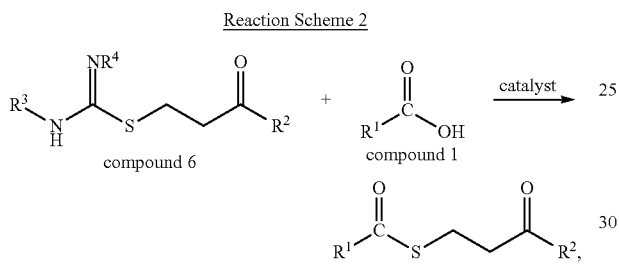

wherein $R^1$, $R^2$, $R^3$, and $R^4$ is each independently selected from one of the group consisting of H, a substituted or unsubstituted alkyl, a substituted or unsubstituted alkoxy, a substituted or unsubstituted aryl, or a substituted or unsubstituted heteroaryl, and the catalyst in Reaction Scheme 2 is the compound represented by Formula I.

One or more substituents of the substituted alkyl, the substituted alkoxy, the substituted aryl, and the substituted heteroaryl may be selected from the group consisting of:
a halogen atom, a hydroxyl, a cyano, a nitro, a thiohydroxy, an amino, a carbonyl, a carbamoyl, a sulfamoyl, a $C_{1-20}$ alkyl, a $C_2$-$C_{20}$ alkenyl, a $C_2$-$C_{20}$ alkynyl, a $C_1$-$C_{20}$ alkoxy, $C_{1-20}$ alkyl alcohol, $C_{1-20}$ haloalkyl, $C_{1-20}$ haloalkylthio, $C_{1-4}$ alkylamino, $C_{1-20}$ alkylamido, $C_{1-20}$ alkylsulfonyl, $C_{1-20}$ haloalkylsulfonyl, $C_{1-20}$ alkoxycarbonyl, $C_{1-20}$ alkylcarbamoyl, $C_{6-10}$ aryl, $C_{4-9}$ cycloalkyl, $C_{4-9}$ heteroaryl, and $C_{4-9}$ heterocycloalkyl.

$R^1$ may represent a substituted or unsubstituted alkyl or a substituted or unsubstituted aryl; $R^2$ may represent a substituted or unsubstituted alkyl, a substituted or unsubstituted alkoxy, or a substituted or unsubstituted aryl; and $R^3$ and $R^4$ may represent a substituted or unsubstituted alkyl or a substituted or unsubstituted aryl.

Compound 6 used in Reaction Scheme 2 is synthesized by Reaction Scheme 3 below:

Reaction Scheme 3

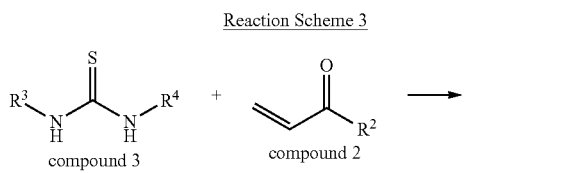

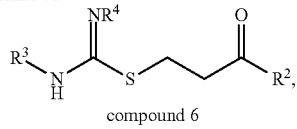

compound 6 wherein $R^2$, $R^3$, and $R^4$ are defined as above.

In summary, by using the compound represented by Formula I as a catalyst, a new method for synthesizing of thioesters may be provided. The method may prepare the thioesters by a one-pot synthesis under mild conditions, without using a thiol, a thioether, or a thiophenol with a pungent smell and activating agent.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

FIG. 3 shows $^1$H NMR spectrum for compound 5a.
FIG. 4 shows $^{13}$C NMR spectrum for compound 5a.
FIG. 8 shows $^{13}$C NMR spectrum for compound 5ca.
FIG. 13 shows $^1$H NMR spectrum for compound 5fa.
FIG. 27 shows $^1$H NMR spectrum for compound 5ma.
FIG. 30 shows $^{13}$C NMR spectrum for compound 6.
FIG. 31 shows $^1$H NMR spectrum for compound 5ab.
FIG. 33 shows $^1$H NMR spectrum for compound 5ac.
FIG. 35 shows $^1$H NMR spectrum for compound 5ad.
FIG. 39 shows $^1$H NMR spectrum for compound 5lc.
FIG. 41 shows $^1$H NMR spectrum for compound 5mc.

DETAILED DESCRIPTION

Figure 1:
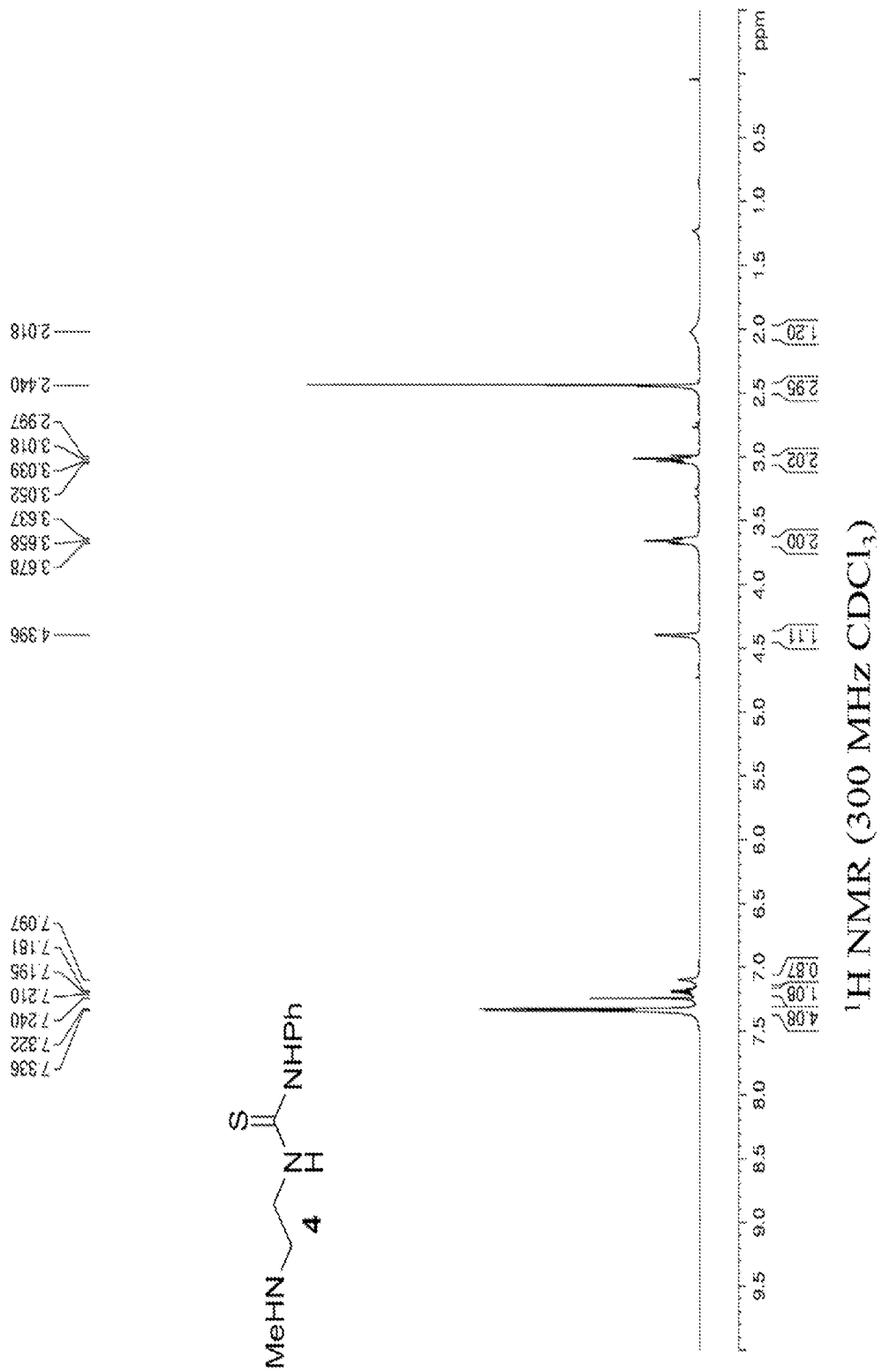
FIG. 1 shows $^1$H NMR spectrum for compound 4.

Exemplary embodiments of the present invention are described herein in the context of an illuminating system and a method thereof.

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as illustrated in the accompanying drawings.

According to an aspect of the present invention, there is provided a method of synthesizing thioester, by using a compound as a catalyst. The compound is represented by Formula (A) below:

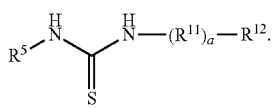

(A)

wherein, in Formula (A), $R^5$ may represent H, a substituted or unsubstituted alkyl, a substituted or unsubstituted aryl, or a substituted or unsubstituted heteroaryl; $R^{11}$ may be a divalent linking group, for example, $R^{11}$ may be independently selected from a substituted or unsubstituted $C_1$-$C_{60}$ alkylene, a substituted or unsubstituted $C_3$-$C_{10}$ cycloalkylene, a substituted or unsubstituted $C_2$-$C_{10}$ heterocycloalkylene, a substituted or unsubstituted $C_2$-$C_{60}$ alkenylene, a substituted or unsubstituted $C_3$-$C_{10}$ cycloalkenylene, a substituted or unsubstituted $C_2$-$C_{10}$ heterocycloalkenylene, a substituted or unsubstituted $C_3$-$C_{10}$ cycloalkylene, a substituted or unsubstituted $C_6$-$C_{60}$ arylene, a substituted or unsubstituted $C_2$-$C_{60}$ heteroarylene, a substituted or unsubstituted divalent non-aromatic condensed polycyclic, a substituted or unsubstituted divalent non-aromatic condensed heteropolycyclic, —COO—, —O—, —(C=O)—, —N=N—, C=N—, —N—, —N($Q_{11}$)($Q_{12}$)-, —S—, —S($Q_{13}$)($Q_{14}$)-, —S(=O)—, or —S(=O)$_2$— ($Q_{11}$ to $Q_{14}$ may be each independently a hydrogen, a deuterium, —F, —Cl, —Br, —I, a hydroxyl, a cyano, a nitro, an amino, an amidino, a hydrazine, a hydrazone, a carboxylic acid or a salt thereof, a sulfonic acid group or a salt thereof, a phosphoric acid group or a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, a $C_3$-$C_{10}$ cycloalkyl, a $C_1$-$C_{10}$ heterocycloalkyl, a $C_3$-$C_{10}$ cycloalkenyl, a $C_2$-$C_{10}$ heterocycloalkenyl, a $C_6$-$C_{60}$ aryl, a $C_1$-$C_{60}$ heteroaryl, a monovalent non-aromatic condensed polycyclic group, or a monovalent non-aromatic condensed heteropolycyclic group); $R^{12}$ may be independently selected from a halogen atom, a hydroxyl, a cyano, a nitro, a thiohydroxy, an amino, a carbonyl, a carbamoyl, a sulfamoyl, a substituted or unsubstituted $C_{1\text{-}20}$ alkyl, a substituted or unsubstituted $C_{2\text{-}20}$ alkenyl, a substituted or unsubstituted $C_{2\text{-}20}$ alkynyl, a substituted or unsubstituted $C_{1\text{-}20}$ alkoxy, a substituted or unsubstituted $C_{1\text{-}20}$ alkyl alcohol, a substituted or unsubstituted $C_{1\text{-}20}$ haloalkyl, a substituted or unsubstituted $C_{1\text{-}20}$ alkylthio, a substituted or unsubstituted $C_{1\text{-}20}$ haloalkylthio, a substituted or unsubstituted $C_{1\text{-}4}$ alkylamino, a substituted or unsubstituted $C_{1\text{-}20}$ alkylamido, a substituted or unsubstituted $C_{1\text{-}20}$ alkylsulfonyl, a substituted or unsubstituted $C_{1\text{-}20}$ haloalkylsulfonyl, a substituted or unsubstituted $C_{1\text{-}20}$ alkoxycarbonyl, a substituted or unsubstituted $C_{1\text{-}20}$ alkylcarbamoyl, a substituted or unsubstituted $C_{6\text{-}10}$ aryl, a substituted or unsubstituted $C_{4\text{-}9}$ cycloalkyl, a substituted or unsubstituted $C_{4\text{-}9}$ heteroaryl, and a substituted or unsubstituted $C_{4\text{-}9}$ heterocycloalkyl; and a may be an integer selected from 0 to 10.

According to embodiments of the present invention, the compound represented by Formula (A) may be represented by Formula I below:

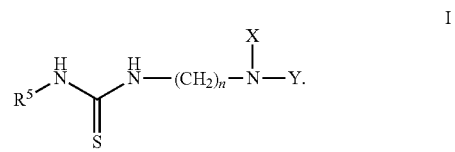

I

In one embodiment, $R^5$ in Formula I may represent H, a substituted or unsubstituted alkyl, a substituted or unsubstituted aryl, or a substituted or unsubstituted heteroaryl; X and Y each independently represents one of H, $C_{1\text{-}10}$ alkyl, $C_{6\text{-}10}$ aryl, $C_{1\text{-}10}$ alkyl alcohol, thiohydroxy, carbonyl, sulfonyl, sulfamoyl, carbamoyl, $C_{1\text{-}10}$ alkoxycarbonyl, $C_{1\text{-}10}$ alkoxycarbamoyl, $C_{1\text{-}10}$ alkylamino, $C_{1\text{-}10}$ alkylsulfonyl, $C_{1\text{-}10}$ haloalkylsulfonyl, ureido, amido, and $C_{1\text{-}10}$ alkoxylcarbamoyl; and n is 0, 1, 2, 3, 4 or 5.

Substituents of the substituted alkyl, the substituted aryl, the substituted heteroaryl, the substituted $C_1$-$C_{60}$ alkylene, the substituted $C_3$-$C_{10}$ cycloalkylene, the substituted $C_2$-$C_{10}$ heterocycloalkylene, the substituted $C_2$-$C_{60}$ alkenylene, the substituted $C_3$-$C_{10}$ cycloalkenylene, the substituted $C_2$-$C_{10}$ heterocycloalkenylene, the substituted $C_3$-$C_{10}$ cycloalkylene, the substituted $C_6$-$C_{60}$ arylene, the substituted $C_2$-$C_{60}$ heteroarylene, the substituted divalent non-aromatic condensed polycyclic group, the substituted divalent non-aromatic condensed heteropolycyclic group, the substituted $C_2$-$C_{20}$ alkenyl, the substituted $C_2$-$C_{20}$ alkynyl, the substituted $C_1$-$C_{20}$ alkoxy, the substituted $C_{1\text{-}20}$ alkyl alcohol, the substituted $C_{1\text{-}20}$ haloalkyl, the substituted $C_{1\text{-}20}$ alkylthio, the substituted $C_{1\text{-}20}$ haloalkylthio, the substituted $C_{1\text{-}4}$ alkylamino, the substituted $C_{1\text{-}20}$ alkylamido, the substituted $C_{1\text{-}20}$ alkylsulfonyl, the substituted $C_{1\text{-}20}$ haloalkylsulfonyl, the substituted $C_{1\text{-}20}$ alkoxycarbonyl, the substituted $C_{1\text{-}20}$ alkylcarbamoyl, the substituted $C_{4\text{-}9}$ cycloalkyl, and the substituted $C_{4\text{-}9}$ heterocycloalkyl may be one or more selected from the group consisting of: a halogen atom, a hydroxyl, a cyano, a nitro, a thiohydroxy, an amino, a carbonyl, a carbamoyl, a sulfamoyl, a $C_{1\text{-}20}$ alkyl, a $C_2$-$C_{20}$ alkenyl, a $C_2$-$C_{20}$ alkynyl, a $C_{1\text{-}20}$ alkoxy, $C_{1\text{-}20}$ alkyl alcohol, $C_{1\text{-}20}$ haloalkyl, $C_{1\text{-}20}$ haloalkylthio, $C_{1\text{-}4}$ alkylamino, $C_{1\text{-}20}$ alkylamido, $C_{1\text{-}20}$ alkylsulfonyl, $C_{1\text{-}20}$ haloalkylsulfonyl, $C_{1\text{-}20}$ alkoxycarbonyl, $C_{1\text{-}20}$ alkylcarbamoyl, $C_{6\text{-}10}$ aryl, $C_{4\text{-}9}$ cycloalkyl, $C_{4\text{-}9}$ heteroaryl, and $C_{4\text{-}9}$ heterocycloalkyl.

In another embodiment, $R^5$ in Formula I may represent a substituted or unsubstituted phenyl, a substituted or unsubstituted thienyl, or a substituted or unsubstituted pyridinyl; One of X and Y may be H and another may be a $C_{1\text{-}10}$ alkyl; and n may be 2.

In yet another embodiment, $R^5$ in Formula I may represent a phenyl, One of X and Y may be H and another may be methyl; and n may be 2.

According to embodiments of the present invention, a method for synthesizing of thioesters is provided, the thioesters are synthesized by using a compound represented by Formula 1 as a catalyst, the method includes the process shown in Reaction Scheme 1 below:

Reaction Scheme 1

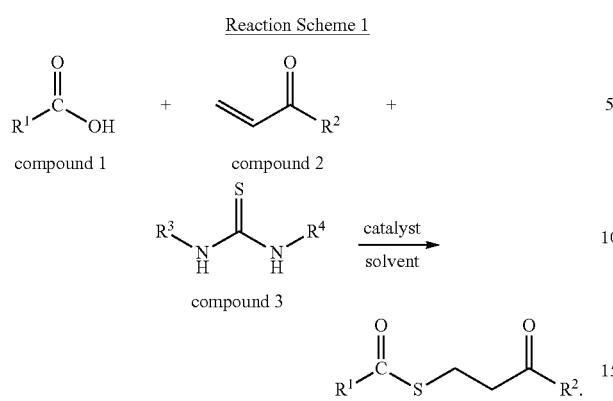

When monitoring the process by $^1$H NMR, the formation and the reduction, accompanied by the formation of the final product, of an intermediate product may be detected.

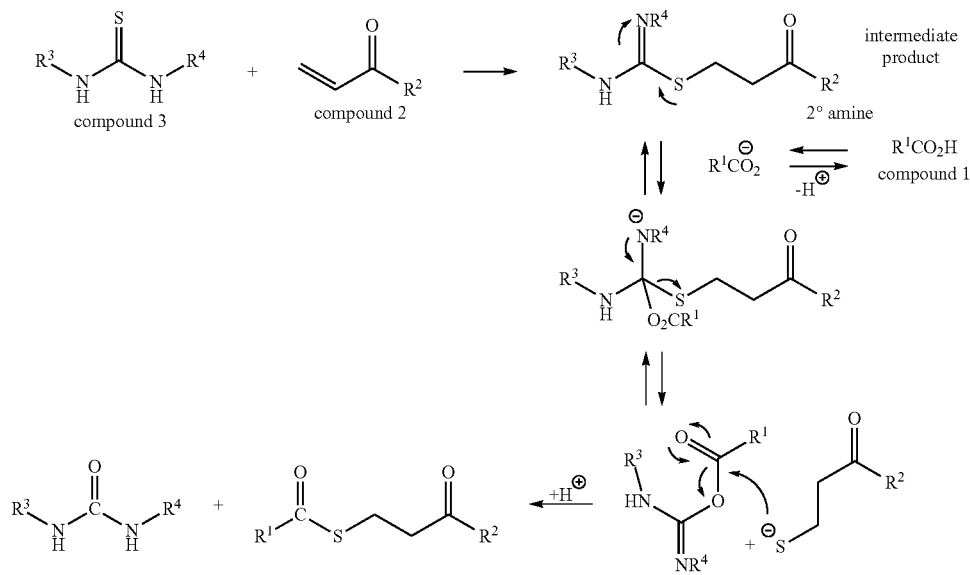

According to the formation of the intermediate product detected above, a method for synthesizing of thioesters is provided. The method includes the process shown in Reaction Scheme 2 below:

Reaction Scheme 2

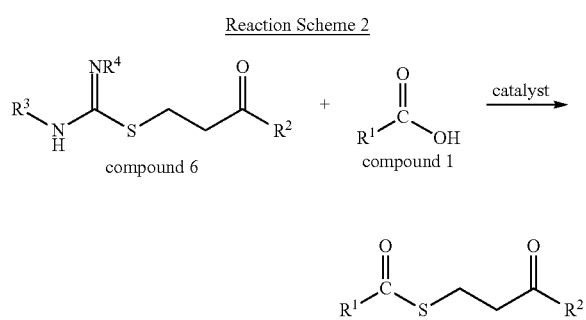

Compound 6 in Reaction Scheme 2 is the intermediate product detected in Reaction Scheme 1, when Reaction Scheme 1 is monitored by $^1$H NMR. Compound 6 may be otherwise synthesized by Reaction Scheme 3 below, which is an addition reaction between compound 2 and compound 3:

Reaction Scheme 3

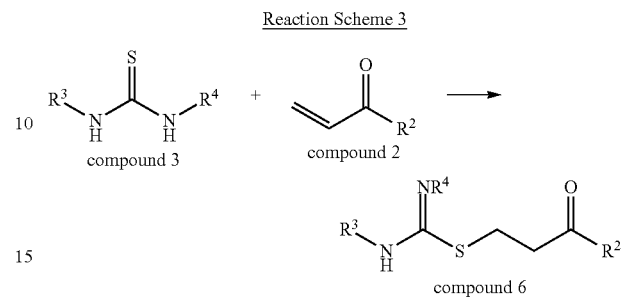

According to embodiments of the present invention, $R^1$, $R^2$, $R^3$, and $R^4$ in Reaction Scheme 1, Reaction Scheme 2, and Reaction Scheme 3 may be each independently selected from one of the group consisting of H, a substituted or unsubstituted alkyl, a substituted or unsubstituted alkoxy, a substituted or unsubstituted aryl, or a substituted or unsubstituted heteroaryl.

Substituents of the substituted alkyl, the substituted alkoxy, and the substituted heteroaryl may be one or more selected from the group consisting of: a halogen atom, a hydroxyl, a cyano, a nitro, a thiohydroxy, an amino, a carbonyl, a carbamoyl, a sulfamoyl, a $C_{1-20}$ alkyl, a $C_2$-$C_{20}$ alkenyl, a $C_2$-$C_{20}$ alkynyl, a $C_{1}$-$C_{20}$ alkoxy, $C_{1-20}$ alkyl alcohol, $C_{1-20}$ haloalkyl, $C_{1-20}$ haloalkylthio, $C_{1-4}$ alkylamino, $C_{1-20}$ alkylamido, $C_{1-20}$ alkylsulfonyl, $C_{1-20}$ haloalkylsulfonyl, $C_{1-20}$ alkoxycarbonyl, $C_{1-20}$ alkylcarbamoyl, $C_{6-10}$ aryl, $C_{4-9}$ cycloalkyl, $C_{4-9}$ heteroaryl, and $C_{4-9}$ heterocycloalkyl.

In an embodiment, $R^1$ of compound 1 may represent a substituted or unsubstituted alkyl or a substituted or unsubstituted aryl; $R^2$ of compound 2 may represent a substituted or unsubstituted alkyl, a substituted or unsubstituted alkoxy, or a substituted or unsubstituted aryl; $R^3$ and $R^4$ of compound 3 may each independently represent a substituted or unsubstituted alkyl or a substituted or unsubstituted aryl; and $R^2$, $R^3$, and $R^4$ of compound 6 may be based on $R^2$, $R^3$, and $R^4$ of compound 2 and compound 3 used in Reaction Scheme 3.

In an embodiment, $R^1$ of compound 1 may represent a substituted or unsubstituted alkyl or a substituted or unsubstituted aryl; $R^2$ of compound 2 may represent a methyl, a phenyl, and an ethoxy; $R^3$ and $R^4$ of compound 3 may each independently represent phenyl and methyl.

In an embodiment, compound 1 may be a carboxylic acid compound, such as acetic acid, benzoic acid, (S)-3-phenyl-2-propionamidopropanoic acid, 3,4-dimethyl benzoic acid, 2,6-dimethyl benzoic acid, o-toluic acid, 4-methoxy benzoic acid, 4-nitro benzoic acid, 2-iodo benzoic acid, 1-naphthoic acid, 2-naphthoic acid, 4-methoxyphenyl acetic acid, 2-(t-butoxycarbonyl amino)-3-phenyl-propionic acid, 4-chloro-1-naphthoic acid, propionic acid, isovaleric acid, dimethylfumarate, and the like, but is not limited thereto. In a preferred embodiment, compound 1 is benzoic acid, o-toluic acid, 3,4-dimethyl benzoic acid, 2,6-dimethyl benzoic acid, 4-methoxy benzoic acid, 2-iodo benzoic acid, 1-naphthoic acid, 2-naphthoic acid, 4-methoxyphenyl acetic acid, propionic acid, isovaleric acid, dimethylfumarate, or (S)-3-phenyl-2-propionamidopropanoic acid.

In an embodiment, compound 2 may be a α,β-unsaturated esters or ketones used as a Michael acceptor in Michael Addition reaction, such as ethylacrylate, methylacrylate, phenyl vinyl ketone, dimethylfumarate, 1-phenyl-2-en-1-one, butenone, naphthoic acid, 4-chloro-1-naphthoic acid, phenyl vinyl ketone, pent-1-en-3-one, and the like, but is not limited thereto. In a preferred embodiment, compound 2 is ethylacrylate, methylacrylate, dimethylfumarate, vinyl phenyl ketone, pent-1-en-3-one or 1-phenylprop-2-en-1-one.

In an embodiment, compound 3 may be a thiourea compound, such as N,N'-diphenylthiourea, N,N'-dimethylthiourea, N-methyl-N'-phenylthiourea, α-naphthylthiourea, and the like, but is not limited thereto. In a preferred embodiment, compound 3 is N,N'-diphenylthiourea.

According to embodiments of the present invention, the solvent used in Reaction Scheme 1 may be a polar aprotic solvent. The example of the polar aprotic solvent include, but not limited to, $CH_2Cl_2$, toluene, dimethylformamide (DMF), tetrahydrofuran (THF) and methanol (MeOH) and any combination thereof. In a preferred embodiment, the polar aprotic solvent is $CH_2Cl_2$ or toluene. The reaction temperature in the process of Reaction Scheme 1 may be varied according to the solvent with different boil point which is used in Reaction Scheme 1. When the solvent with higher boil point is used, it allows Reaction Scheme 1 to progress in a condition with higher temperature. The reaction time of Reaction Scheme 1 may be shortened by raising the reaction temperature in the process of Reaction Scheme 1.

According to embodiments of the present invention, in Reaction Scheme 1, the molar ratio of compound 1:compound 2:compound 3:catalyst is 1-1.5:1-1.5:1-1.5:0.1-0.5. The thioesters are obtained in a poor yield, when the molar ratio of lower than 0.1.

In Reaction Scheme 1, in the presence of a catalyst, a thioester compound may be synthesized by a carboxylic acid compound, an α,β-unsaturated esters or ketones which is a Michael acceptor, and a thiourea compound, at the temperature range from about 40° C. to 90° C. for about 10 hours to about 48 hours, by using the thiourea compound as a dual role reagent, the 2° amine base and the source of the sulfur.

Compound 1 and the catalyst used in Reaction Scheme 2 may be same as which in Reaction Scheme 1. Therefore, the definition of compound 1 and the catalyst are omitted. The solvent used in Reaction Scheme 2 may be the same as that in Reaction Scheme 1 as well. Therefore, the description of the solvent is omitted.

In Reaction Scheme 2, a thioester compound may be synthesized by compound 6, compound 2, and the catalyst. The thioester compound may be synthesized by Reaction Scheme 2 at the temperature range from about 20° C. to 110° C. for about 12 h to about 48 h, when the molar ratio of compound 2:compound 6:catalyst is 1-1.5:1-1.5:0.1-0.5.

Compound 6 used in Reaction Scheme 2 may be synthesized by Reaction Scheme 3, which is an addition reaction between compound 2 and compound 3. The solvent used in Reaction Scheme 3 may be same as which in Reaction Scheme 1 and Reaction Scheme 2. Compound 6 may be synthesized by Reaction Scheme 3 at the temperature range from about 20° C. to 110° C. for about 12 h to about 48 h, when the molar ratio of compound 2:compound 3 is 1-1.5:1-1.5.

The following is the examples of synthesizing compounds represented by Formula I, which may be used as a catalyst, according to the present invention.

The Synthesis of Compound 4

Figure 2:
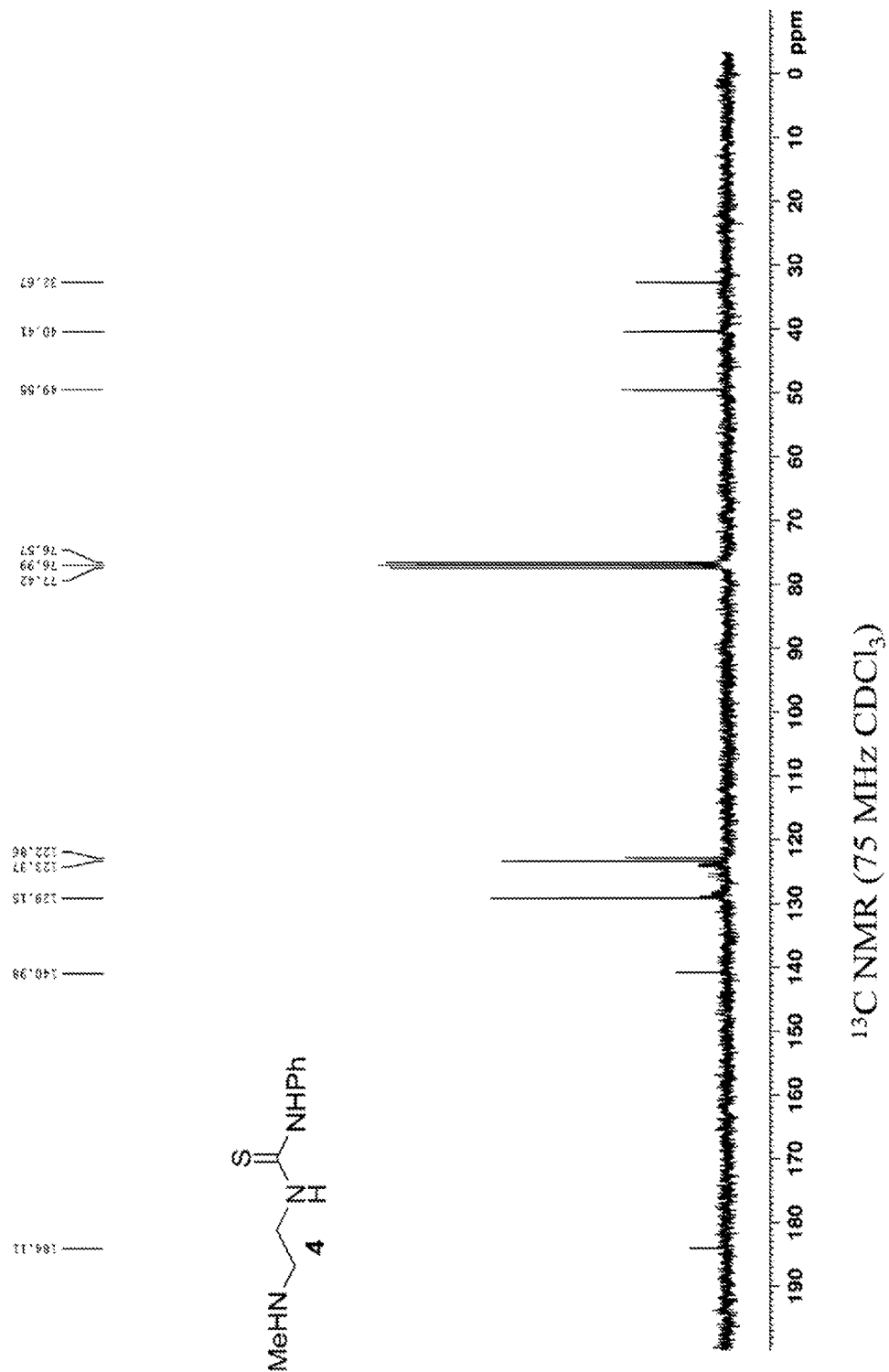
FIG. 2 shows $^{13}$C NMR spectrum for compound 4.

Triethylamine (328.3 mg, 3.24 mmol) was added to a solution of N-methylethane-1,2-diamine (15.2 mg, 3.24 mmol), and phenylisothiocyanate (438.5 mg, 3.24 mmol) in THF (0.5 mL). The reaction was stirred at room temperature for 18 h, and then the excess solvent was evaporated under vacuum. The crude product was purified by column chromatography ($SiO_2$:MeOH/EtOAc, 1:4; $R_f$ 0.35) to give the compound 4 which is 1-(2-(Methylamino)ethyl)-3-phenyl-thiourea (549.5 mg, 2.62 mmol, 81%), as a white solid. FIG. 1 shows $^1$H NMR spectrum for compound 4, and FIG. 2 shows $^{13}$C NMR spectrum for compound 4.

Mp 161.0-163.0° C.; $^1$H NMR (300 MHz, CDCl3) δ 7.33-7.32 (m, 4H), 7.21-7.18 (m, 1H), 7.09 (s, 1H), 4.39 (s, 1H), 3.65 (t, J=6.3 Hz, 2H), 3.01 (t, J=6.3 Hz, 2H), 2.44 (s, 3H), 2.01 (s, 1H); $^{13}$C NMR (75 MHz, CDCl3) 184.1, 140.9, 129.1, 123.3, 122.8, 49.5, 40.4, 32.6; HRMS (ESI⁻) calcd for [M−H]⁻ ($C_{10}H_{14}N_3S$) 208.0908. found 208.0909.

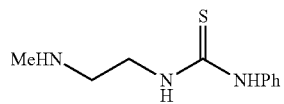

4

The following are examples of the thioesters, which is synthesized according to Reaction Scheme 1 of the present invention, by using compound 4 prepared above as a catalyst.

Example 1

Figure 4:
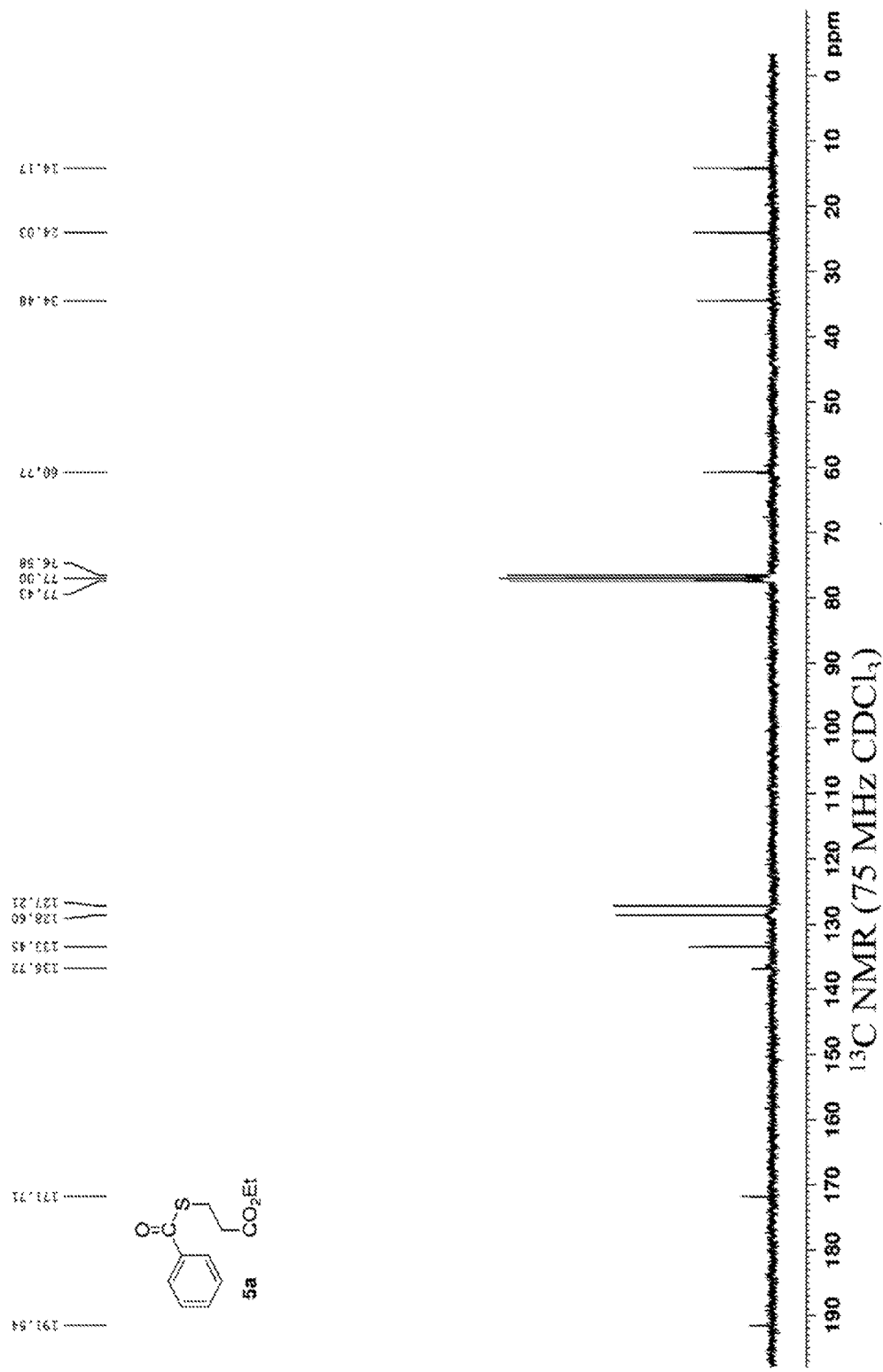

42.3 mg of compound 4 (0.20 mmol, 20 mol %) used as a catalyst was added to a solution of 184.4 mg of benzoic acid (1.51 mmol, 1.5 equiv), 100.9 mg of ethylacrylate (1.01 mmol, 1.0 equiv), and 344.7 mg of N,N'-diphenylthiourea (1.51 mmol, 1.5 equiv) in toluene (5.0 mL). The reaction was heated in an oil bath (80° C.) for 24 h, and then the excess solvent was evaporated under vacuum. The crude product was purified by column chromatography ($SiO_2$:

EtOAc/n-hexane, 1:5; $R_f$ 0.76), and 131.2 mg of compound 5a (0.55 mmol, 55%), which is ethyl 3-(benzoylthio)propanoate, was isolated as a colorless oil after column chromatography. FIG. 3 shows $^1$H NMR spectrum for compound 5a, and FIG. 4 shows $^{13}$C NMR spectrum for compound 5a.

$^1$H NMR (300 MHz, CDCl3) δ 7.93 (d, J=7.2 Hz, 2H), 7.54 (t, J=7.3 Hz, 1H), 7.41 (t, J=7.6 Hz, 2H), 4.18 (q, J=7.2 Hz, 2H), 3.29 (t, J=6.9 Hz, 2H), 2.69 (t, J=6.9 Hz, 2H), 1.21 (t, J=7.2 Hz, 3H); $^{13}$C NMR (75 MHz, CDCl3) 191.5, 171.7, 136.7, 133.4, 128.6, 127.2, 60.7, 34.4, 24.0, 14.1; IR (neat) 2981 (m), 2360 (m), 1735 (s), 1664 (s), 1207 (s), 912 (s), 690 (s) cm$^1$; HRMS (ESI$^+$) calcd for [M+Na]$^+$ ($C_{12}F_{14}O_3NaS$) 261.0561. found 261.0556.

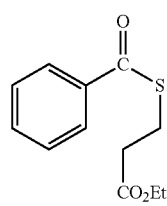

5a

Example 2

Figure 5:
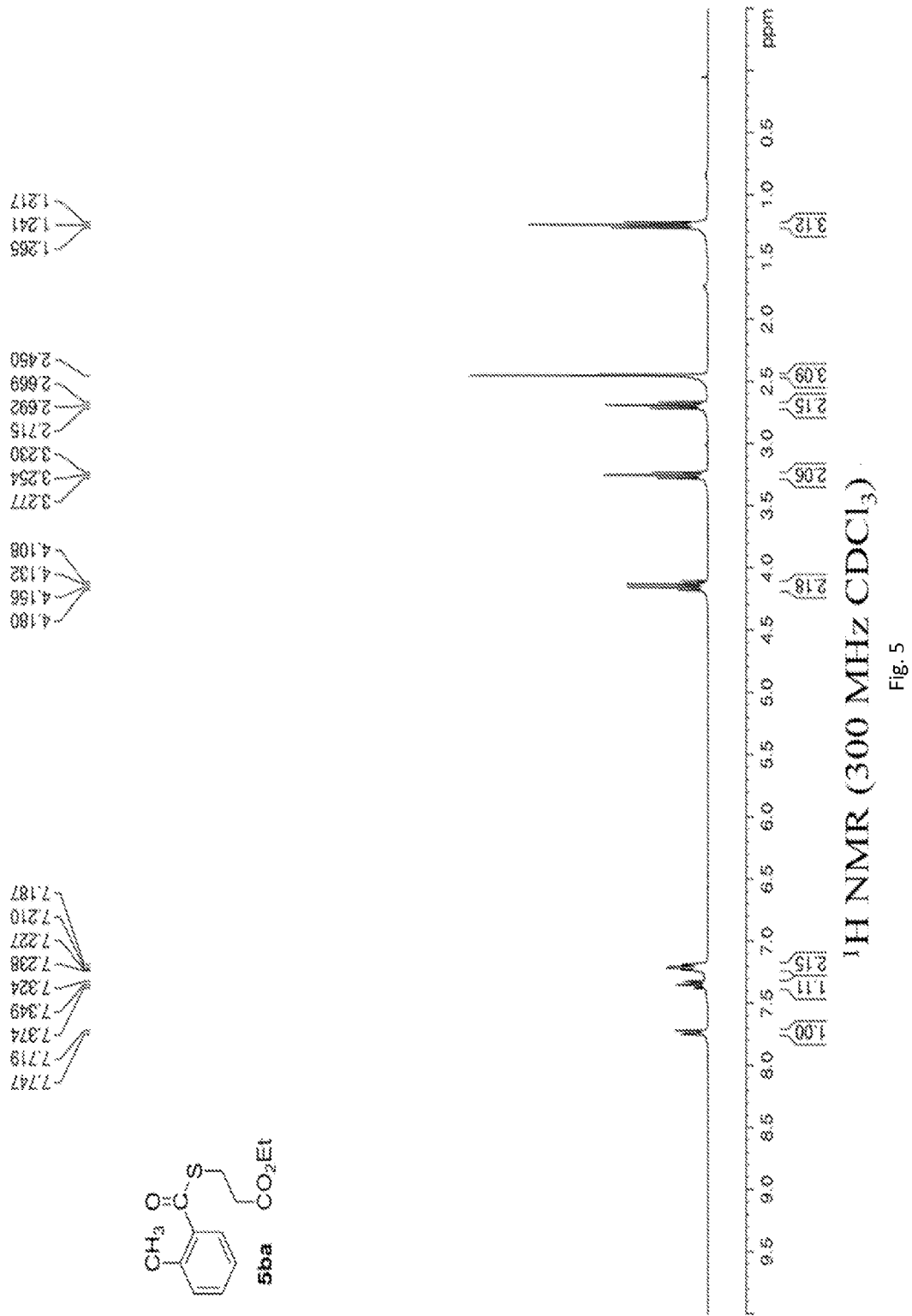
FIG. 5 shows $^1$H NMR spectrum for compound 5ba.
Figure 6:
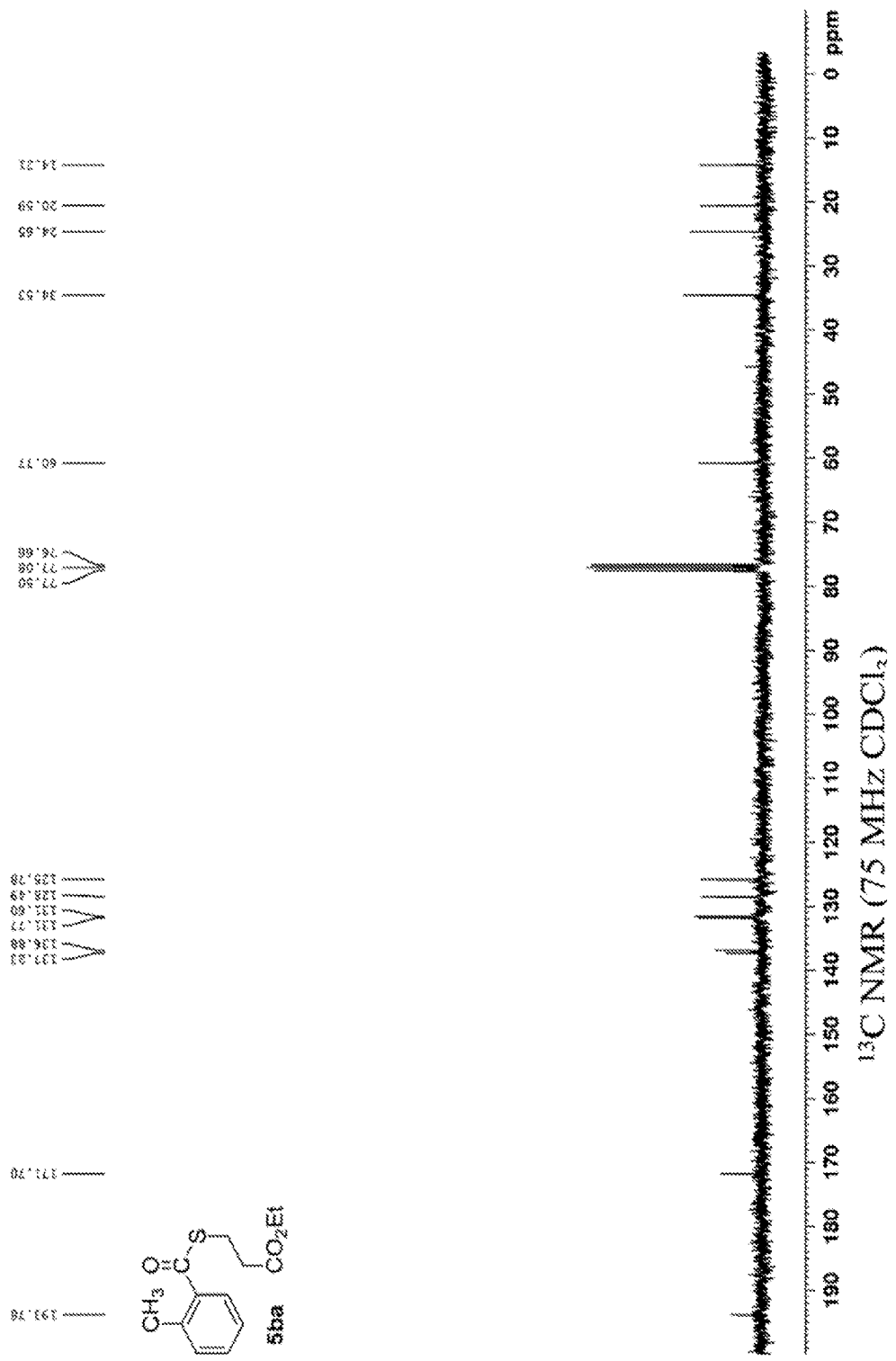
FIG. 6 shows $^{13}$C NMR spectrum for compound 5ba.

154.5 mg of compound 5ba (0.61 mmol, 60%), which is ethyl 3-(2-methylbenzoylthio)propanoate, was isolated as a colorless oil after column chromatography (SiO$_2$:EtOAc/n-hexane, 1:5; $R_f$ 0.78) in the same (or substantially the same) manner as in Example 1, except that o-toluic acid (208.3 mg, 1.53 mmol) was used instead of benzoic acid, and 102.5 mg of ethylacrylate (1.03 mmol), and 349.3 mg of N,N'-diphenylthiourea (1.53 mmol) were used. FIG. 5 shows $^1$H NMR spectrum for compound 5ba, and FIG. 6 shows $^{13}$C NMR spectrum for compound 5ba.

$^1$H NMR (300 MHz, CDCl3) δ 7.74 (d, J=8.4 Hz, 1H), 7.37 (t, J=7.5 Hz, 1H), 7.22-7.18 (m, 2H), 4.18 (q, J=7.2 Hz, 2H), 3.25 (t, J=6.9 Hz, 2H), 2.69 (t, J=6.9 Hz, 2H), 2.45 (s, 3H), 1.24 (t, J=7.2 Hz, 3H); $^{13}$C NMR (75 MHz, CDCl3) 191.7, 171.7, 137.2, 136.8, 131.7, 131.6, 128.4, 125.7, 60.7, 34.5, 24.6, 20.5, 14.2; HRMS (ESI$^+$) calcd for [M+H]$^+$ ($C_{13}H_{17}O_3S$) 253.0898. found 253.0895.

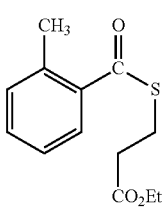

5ba

Example 3

Figure 7:
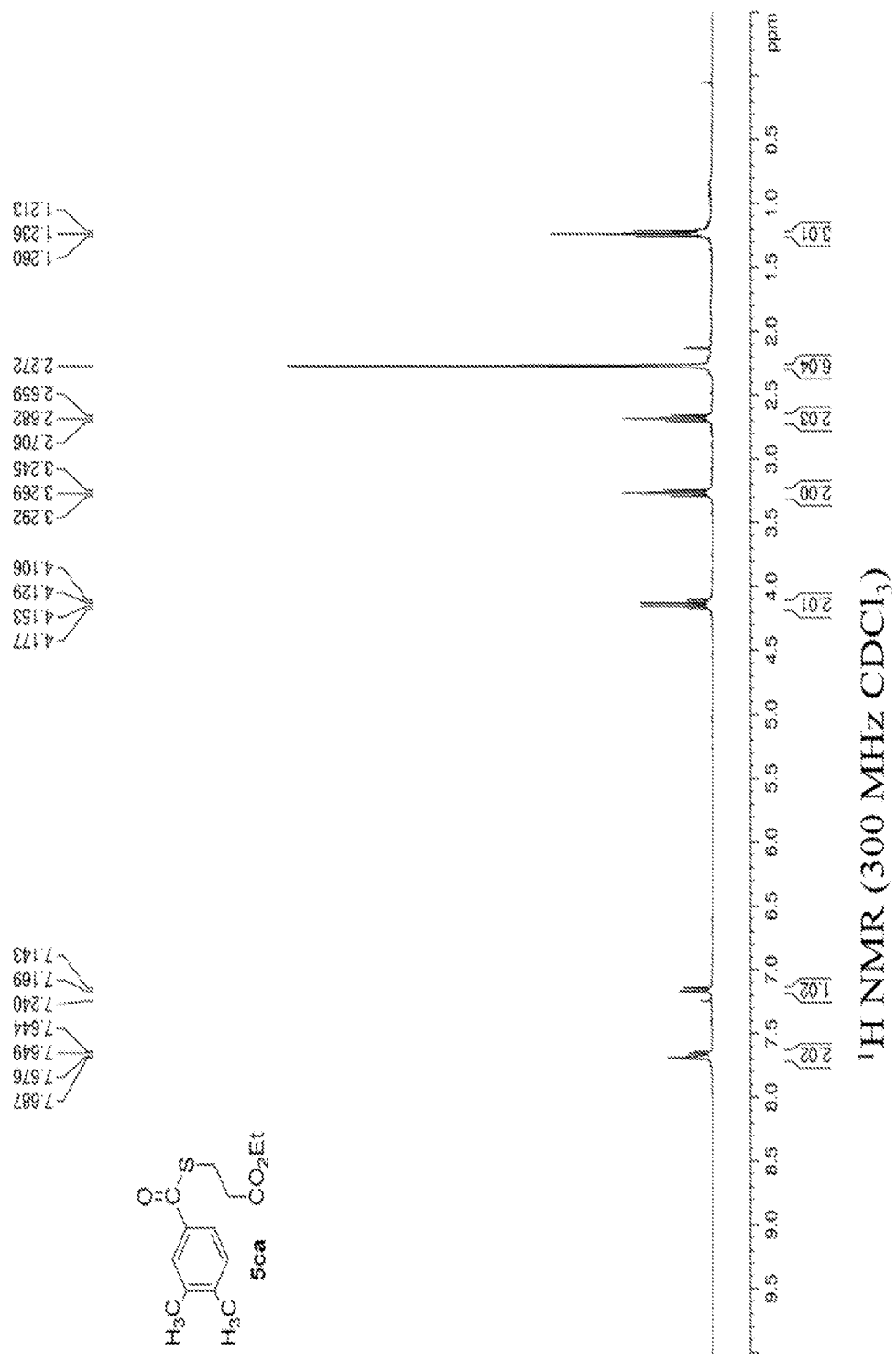
FIG. 7 shows $^1$H NMR spectrum for compound 5ca.

139.2 mg of compound 5ca (0.52 mmol, 55%), which is ethyl 3-(3,4-dimethylbenzoylthio)propanoate, was isolated as a colorless oil after column chromatography (SiO$_2$: EtOAc/n-hexane, 1:5; $R_f$ 0.72) in the same (or substantially the same) manner as in Example 1, except that 3,4-dimethyl benzoic acid (214.1 mg, 1.42 mmol) was used instead of benzoic acid, and 95.3 mg of ethylacrylate (0.951 mmol), and 325.6 mg of N,N'-diphenylthiourea (1.42 mmol) were used. FIG. 7 shows $^1$H NMR spectrum for compound 5ca, and FIG. 8 shows $^{13}$C NMR spectrum for compound 5ca.

$^1$H NMR (300 MHz, CDCl3) δ 7.68-7.64 (m, 2H), 7.16 (d, J=7.8 Hz, 1H), 4.17 (q, J=7.2 Hz, 2H), 3.26 (t, J=7.0 Hz, 2H), 2.68 (t, J=7.0 Hz, 2H), 2.27 (s, 6H), 1.23 (t, J=7.2 Hz, 3H); $^{13}$C NMR (75 MHz, CDCl3) 191.2, 171.7, 143.0, 136.9, 134.6, 129.7, 128.2, 124.8, 60.6, 34.5, 23.8, 19.9, 19.6, 14.1; HRMS (ESI$^+$) calcd for [M+H]$^+$ ($C_{14}H_{19}O_3S$) 267.1055. found 267.1057.

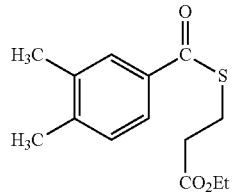

5ca

Example 4

Figure 9:
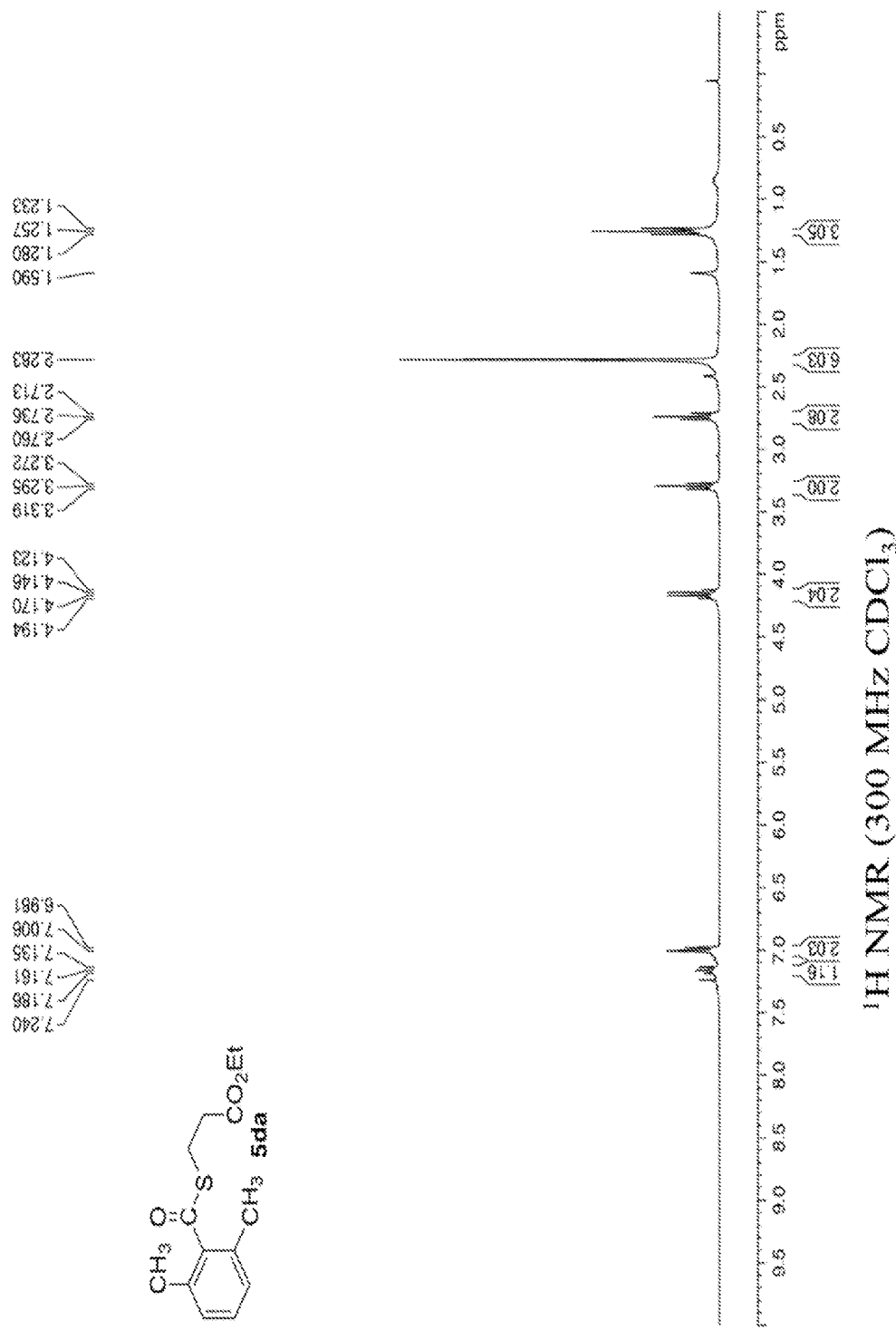
FIG. 9 shows $^1$H NMR spectrum for compound 5da.
Figure 10:
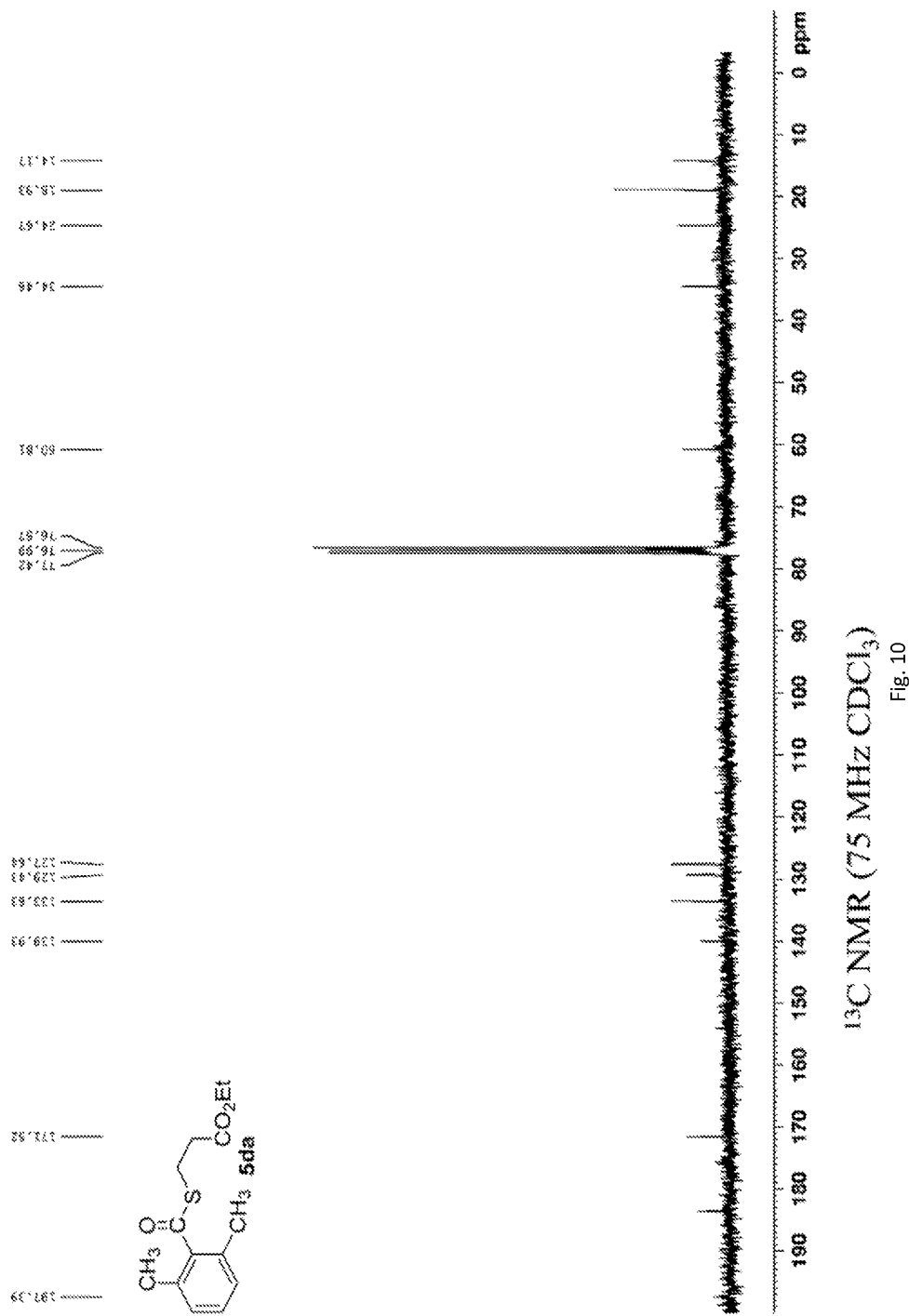
FIG. 10 shows $^{13}$C NMR spectrum for compound 5da.

138.5 mg of compound 5da (0.52 mmol, 52%), which is ethyl 3-(2,6-dimethylbenzoylthio)propanoate, was isolated as a colorless oil after column chromatography (SiO$_2$: EtOAc/n-hexane, 1:5; $R_f$ 0.72) in the same (or substantially the same) manner as in Example 1, except that 2,6-dimethyl benzoic acid (226.7 mg, 1.51 mmol) was used instead of benzoic acid, and 101.2 mg of ethylacrylate (1.01 mmol), and 344.7 mg of N,N'-diphenylthiourea (1.51 mmol) were used. FIG. 9 shows $^1$H NMR spectrum for compound 5da, and FIG. 10 shows $^{13}$C NMR spectrum for compound 5da.

$^1$H NMR (300 MHz, CDCl3) δ 7.16 (t, J=7.5 Hz, 1H), 7.01 (d, J=7.5 Hz, 2H), 4.19 (q, J=7.2 Hz, 2H), 3.29 (t, J=7.0 Hz, 2H), 2.73 (t, J=7.0 Hz, 2H), 2.28 (s, 6H), 1.25 (t, J=7.2 Hz, 3H); $^{13}$C NMR (75 MHz, CDCl3) 197.2, 171.5, 139.9, 133.6, 129.4, 127.6, 60.8, 34.4, 24.6, 18.9, 14.1; HRMS (ESI$^+$) calcd for [M+H]$^+$ ($C_{14}H_{19}O_3S$) 267.1055. found 267.1059.

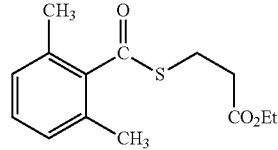

5da

Example 5

Figure 11:
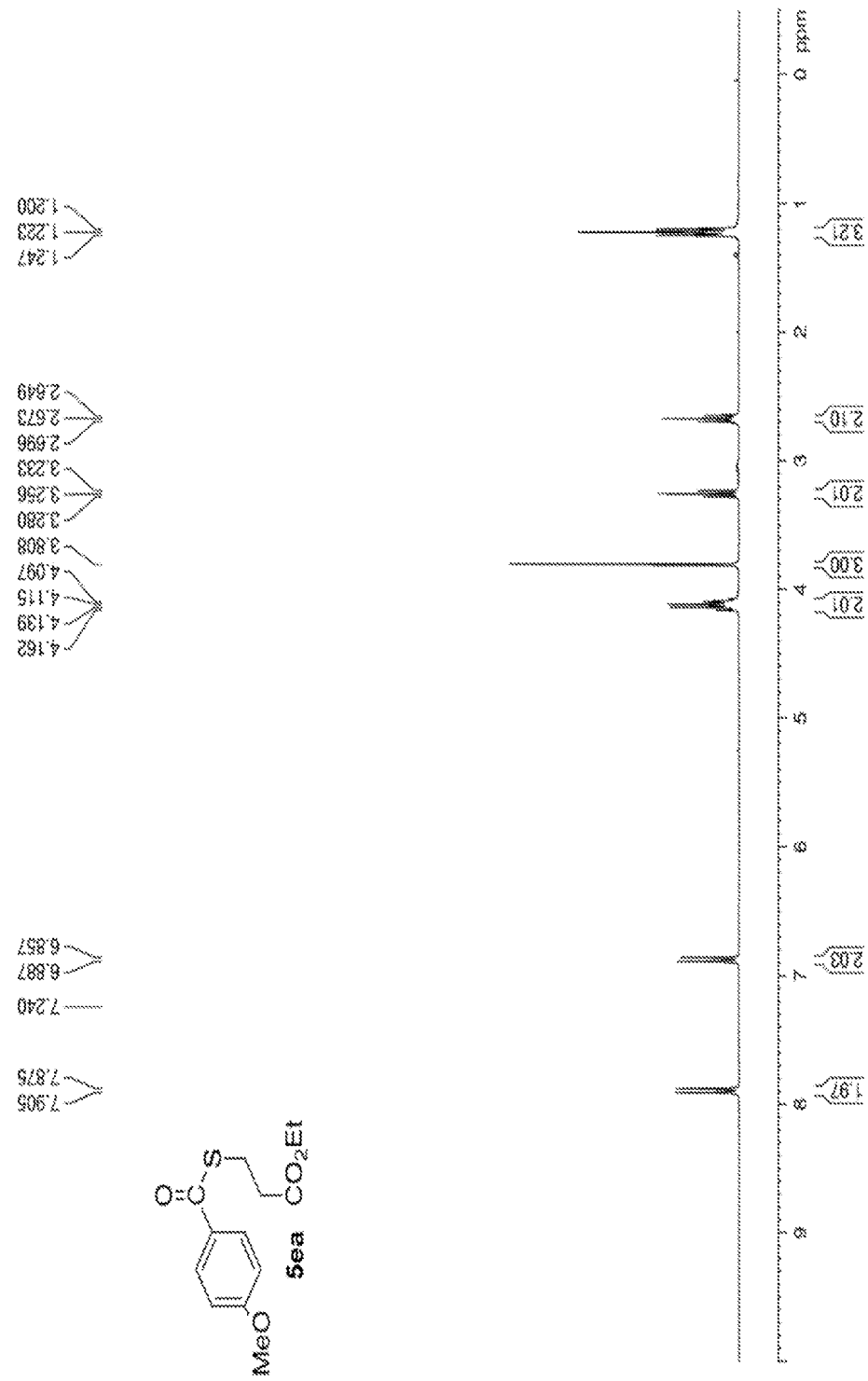
FIG. 11 shows $^1$H NMR spectrum for compound 5ea.
Figure 12:
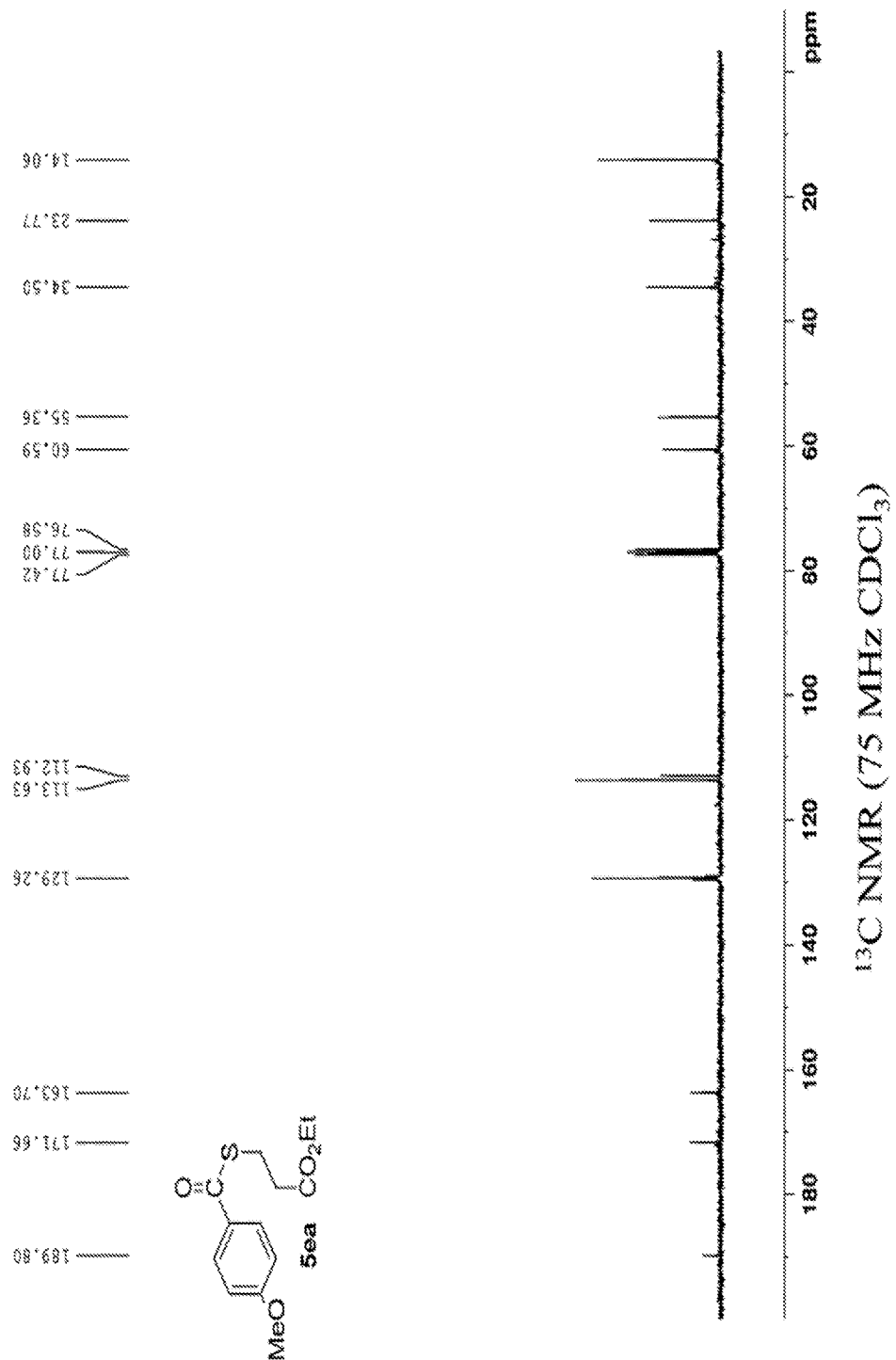
FIG. 12 shows $^{13}$C NMR spectrum for compound 5ea.

85.5 mg of compound 5ea (0.32 mmol, 62%), which is ethyl 3-(4-methoxybenzoylthio)propanoate, was isolated as a light yellow oil after column chromatography (SiO$_2$: EtOAc/n-hexane, 1:5; $R_f$ 0.75) in the same (or substantially the same) manner as in Example 1, except that 4-methoxy benzoic acid (117.7 mg, 0.77 mmol) was used instead of benzoic acid, and 51.7 mg of ethylacrylate (0.52 mmol), 176.7 mg of N,N'-diphenylthiourea (0.77 mmol) in 2.5 mL of toluene were used. FIG. 11 shows $^1$H NMR spectrum for compound 5ea, and FIG. 12 shows $^{13}$C NMR spectrum for compound 5ea.

$^1$H NMR (300 MHz, CDCl3) δ 7.91 (d, J=9.0 Hz, 2H), 6.88 (d, J=9.0 Hz, 2H), 4.16 (q, J=7.0 Hz, 2H), 3.81 (s, 3H), 3.25 (t, J=7.0 Hz, 2H), 2.67 (t, J=7.0 Hz, 2H), 1.25 (t, J=7.0 Hz, 3H); $^{13}$C NMR (75 MHz, CDCl3) 189.8, 171.6, 163.0, 129.2, 113.6, 112.9, 60.5, 55.3, 34.5, 23.7, 14.1; HRMS (ESI$^+$) calcd for [M+H]$^+$ (C$_{14}$H$_{19}$O$_3$S) 291.0667. found 291.0675.

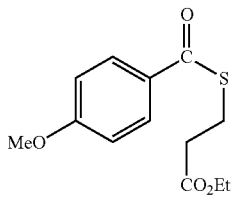

5ea

Example 6

Figure 14:
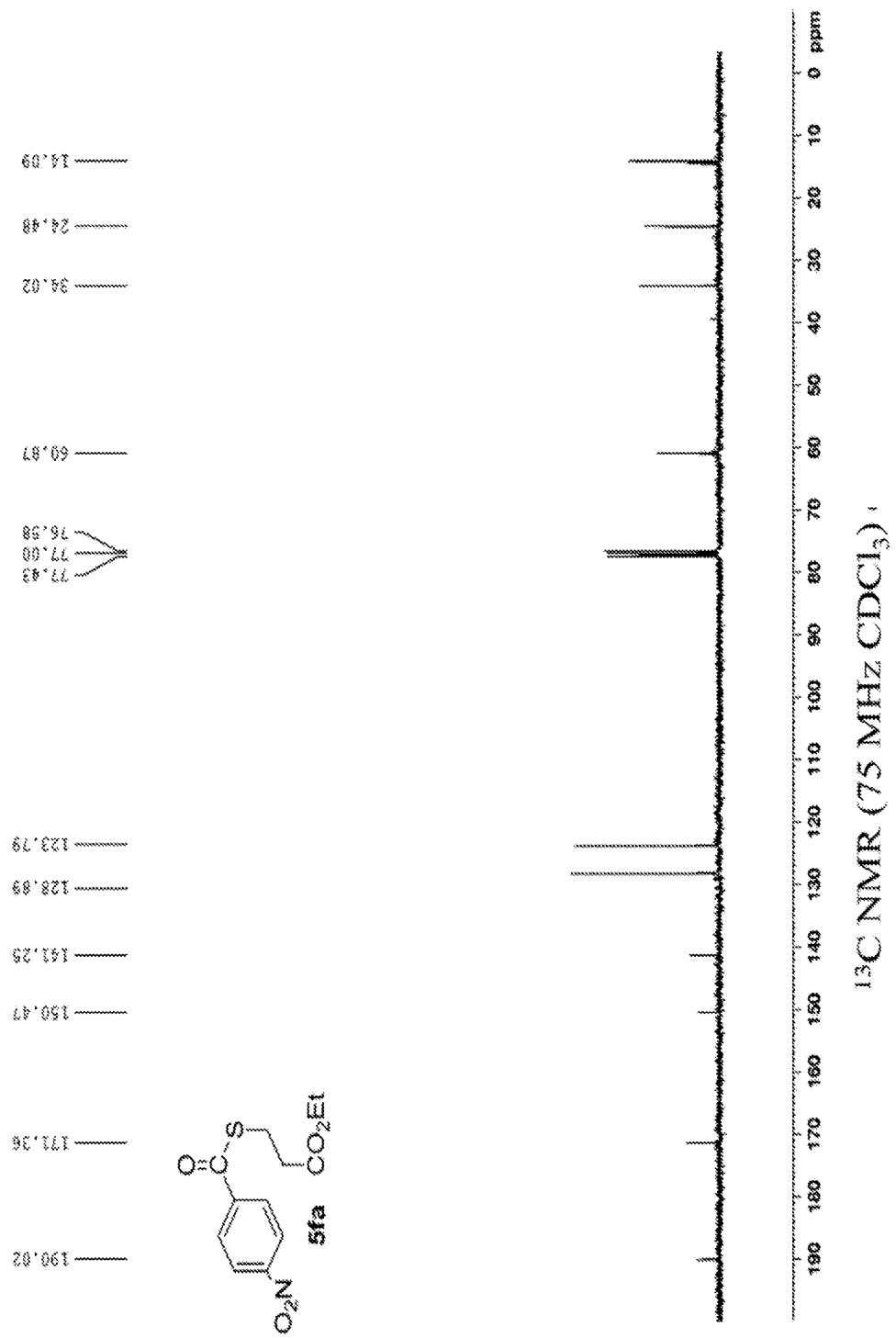
FIG. 14 shows $^{13}$C NMR spectrum for compound 5fa.

117.3 mg of compound 5fa (0.41 mmol, 41%), which is ethyl 3-(4-nitrobenzoylthio)propanoate, was isolated as a light yellow oil after column chromatography (SiO$_2$:EtOAc/n-hexane, 1:5; R$_f$ 0.78) in the same (or substantially the same) manner as in Example 1, except that 4-nitro benzoic acid (252.3 mg, 1.51 mmol) was used instead of benzoic acid, and 100.9 mg of ethylacrylate (1.01 mmol), 344.7 mg of N,N'-diphenylthiourea (1.51 mmol) and 41.8 mg of compound 4 (0.20 mmol) in toluene (5.0 mL) were used. FIG. 13 shows $^1$H NMR spectrum for compound 5fa, and FIG. 14 shows $^{13}$C NMR spectrum for compound 5fa.

$^1$H NMR (300 MHz, CDCl3) δ 8.26 (d, J=9.0 Hz, 2H), 8.07 (d, J=9.0 Hz, 2H), 4.17 (q, J=7.2 Hz, 2H), 3.32 (t, J=6.9 Hz, 2H), 2.67 (t, J=6.9 Hz, 2H), 1.23 (t, J=7.2 Hz, 3H); $^{13}$C NMR (75 MHz, CDCl3) 190.0, 171.3, 150.4, 141.2, 128.8, 123.7, 60.8, 34.0, 24.4, 14.1; HRMS (ESI$^+$) calcd for [M+H]$^+$ (C$_{12}$H$_{14}$O$_5$NS) 284.0593. found 284.0586.

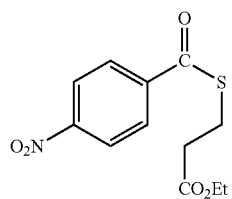

5fa

Example 7

Figure 15:
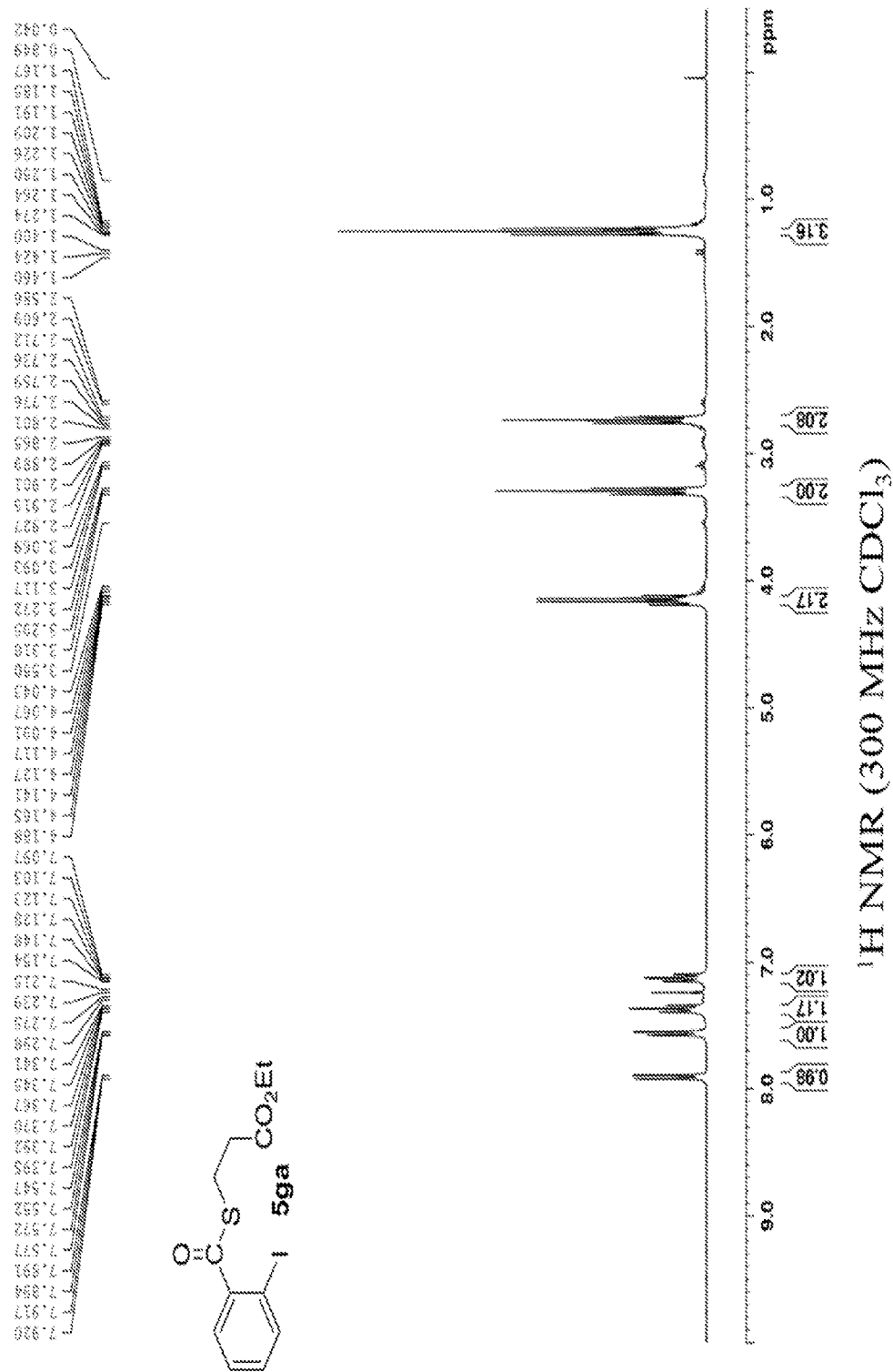
FIG. 15 shows $^1$H NMR spectrum for compound 5ga.
Figure 16:
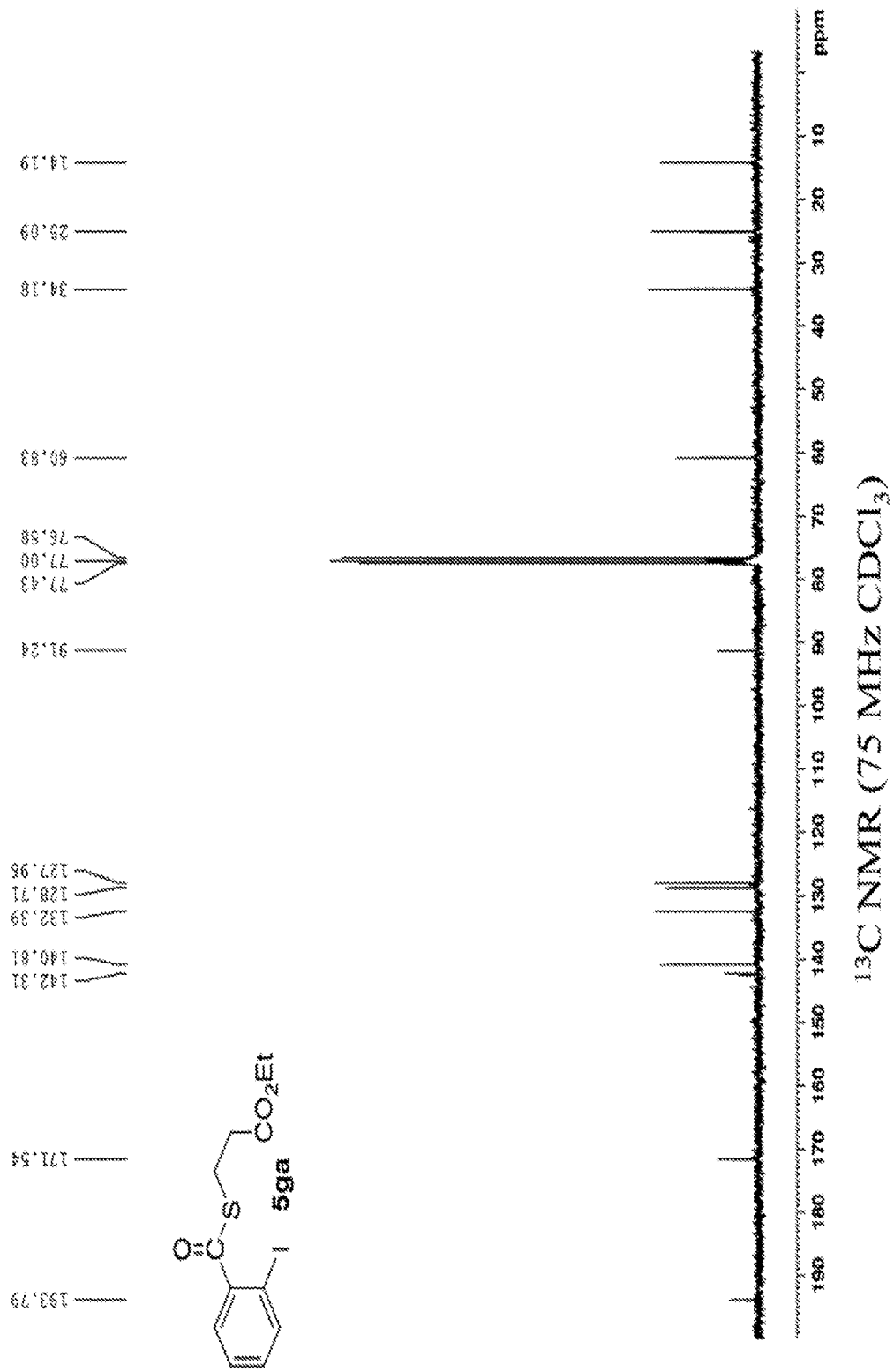
FIG. 16 shows $^{13}$C NMR spectrum for compound 5ga.

57.1 mg of compound 5ga (0.157 mmol, 30%), which is ethyl 3-(2-iodobenzoylthio)propanoate, was isolated as a light yellow oil after column chromatography (SiO$_2$:EtOAc/n-hexane, 1:5; R$_f$ 0.72) in the same (or substantially the same) manner as in Example 1, except that 2-iodo benzoic acid (194.7 mg, 0.78 mmol) was used instead of benzoic acid, and 52.4 mg of ethylacrylate (0.52 mmol), 179.2 mg of N,N'-diphenylthiourea (0.78 mmol) and 21.9 mg of compound 4 (0.10 mmol) in toluene (2.5 mL) were used. FIG. 15 shows $^1$H NMR spectrum for compound 5ga, and FIG. 16 shows $^{13}$C NMR spectrum for compound 5ga.

$^1$H NMR (300 MHz, CDCl3) δ 7.92 (dd, J=7.8 Hz, J=0.9 Hz, 1H), 7.57 (dd, J=7.5 Hz, J=1.5 Hz, 1H), 7.39 (dt, J=7.8 Hz, J=0.9 Hz, 1H), 7.39 (dt, J=7.8 Hz, J=1.5 Hz, 1H), 4.17 (q, J=7.2 Hz, 2H), 3.32 (t, J=6.9 Hz, 2H), 2.67 (t, J=6.9 Hz, 2H), 1.23 (t, J=7.2 Hz, 3H); $^{13}$C NMR (75 MHz, CDCl3) 193.7, 171.5, 142.3, 140.8, 132.3, 128.7, 127.9, 91.2, 60.8, 34.1, 25.1, 14.1; HRMS (ESI$^+$) calcd for [M+H]$^+$ (C$_{12}$H$_{14}$O$_3$SI) 364.9708. found 364.9701.

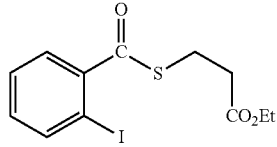

5ga

Example 8

Figure 17:
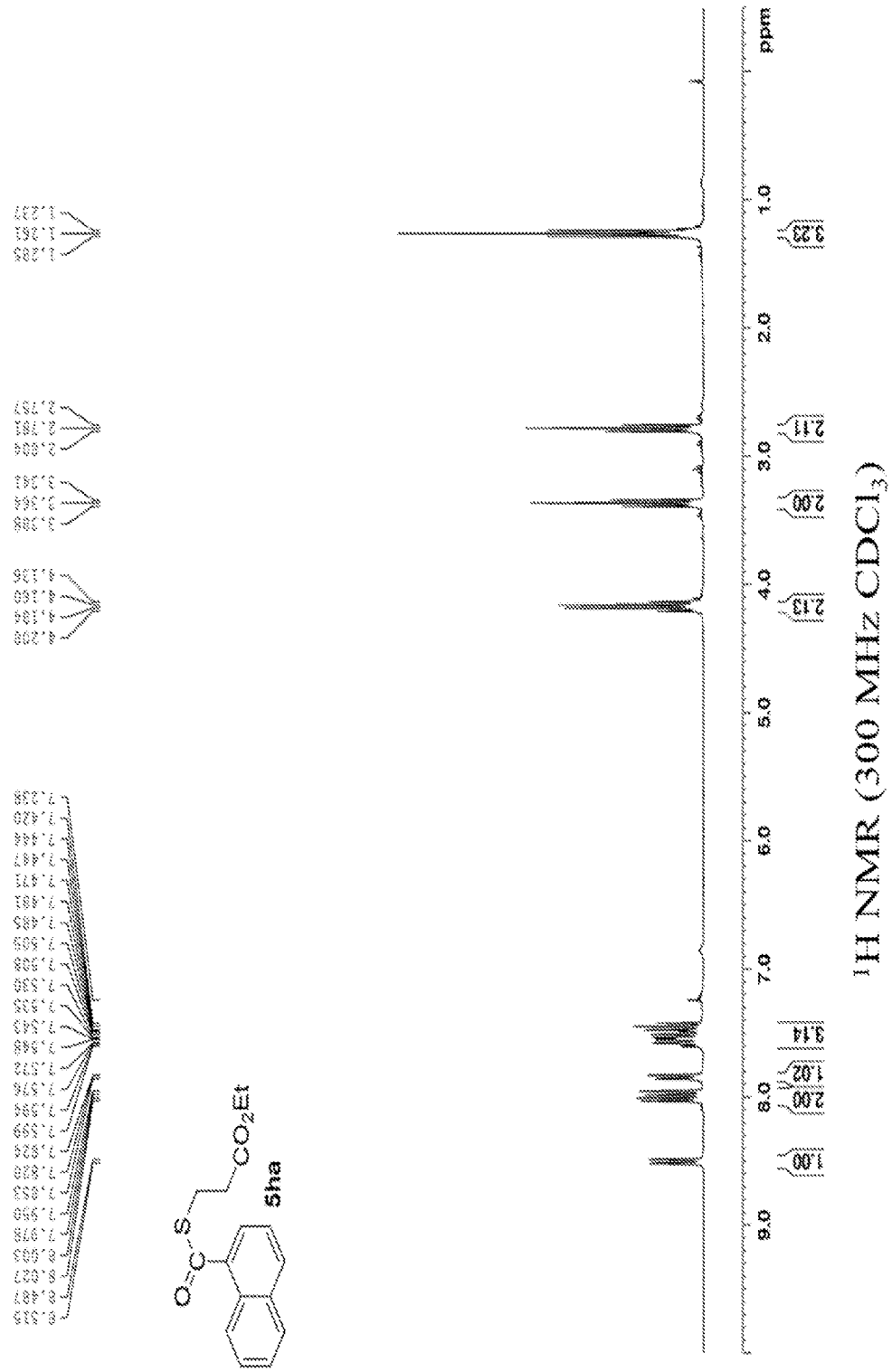
FIG. 17 shows $^1$H NMR spectrum for compound 5ha.
Figure 18:
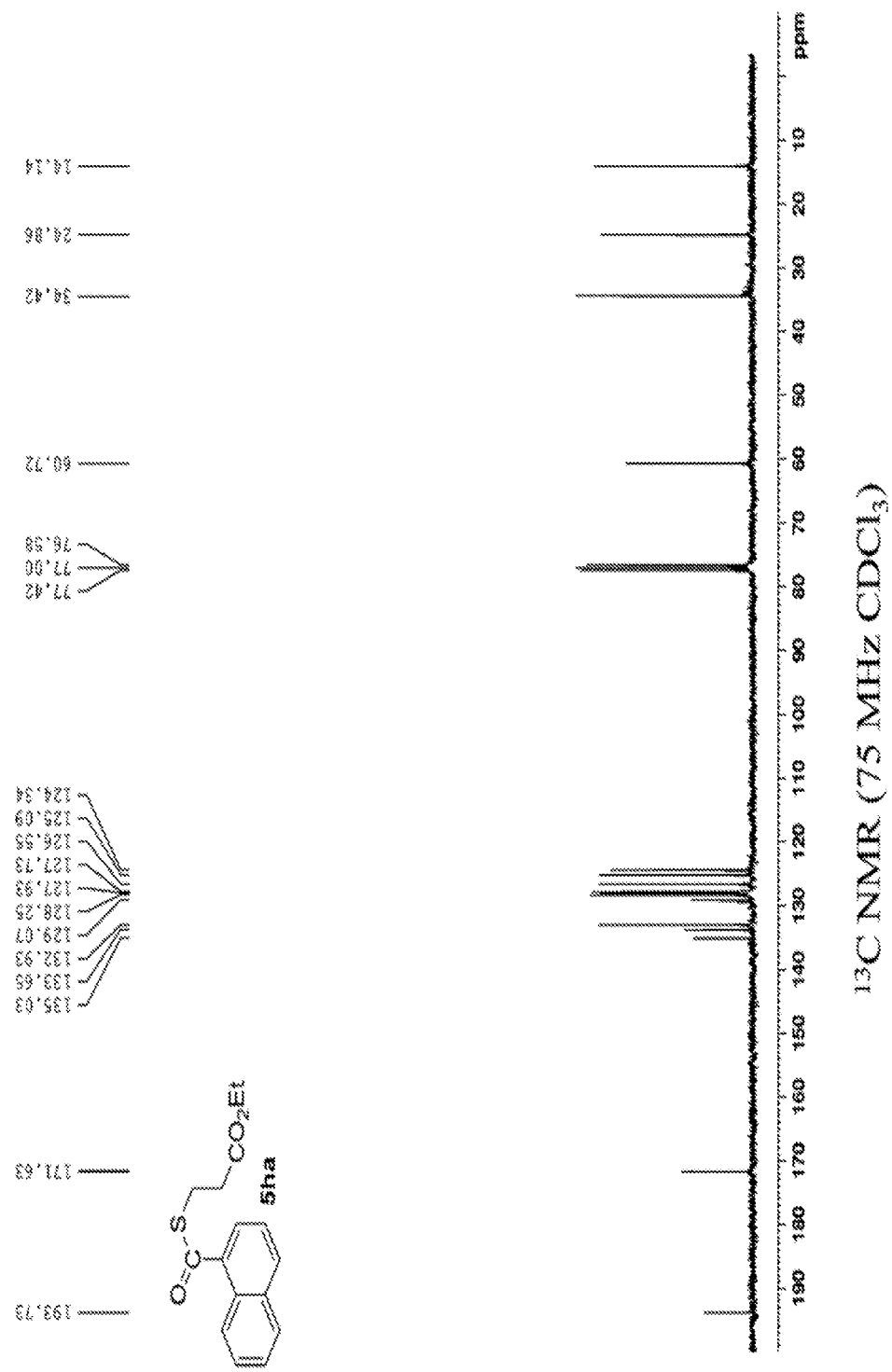
FIG. 18 shows $^{13}$C NMR spectrum for compound 5ha.

39.5 mg of compound 4 (0.19 mmol, 20 mol %) was added as a catalyst to a solution of 1-naphthoic acid (237.2 mg, 1.38 mmol), ethylacrylate (95.1 mg, 0.95 mmol), and N,N'-diphenylthiourea (314.6 mg, 1.38 mmol) in toluene (5.0 mL). The reaction was heated in an oil bath (80° C.) for 48 h, and then the excess solvent was evaporated under vacuum. The crude product was purified by column chromatography (SiO$_2$:EtOAc/n-hexane, 1:5; R$_f$ 0.72), and 125.5 mg of compound 5ha (0.43 mmol, 46%), which is ethyl 3-(1-naphthoylthio)propanoate, was isolated as a light yellow oil after column chromatography. FIG. 17 shows $^1$H NMR spectrum for compound 5ha, and FIG. 18 shows $^{13}$C NMR spectrum for compound 5ha.

$^1$H NMR (300 MHz, CDCl3) δ 8.51 (d, J=8.4 Hz, 1H), 8.07 (d, J=7.2 Hz, 1H), 7.97 (d, J=8.4 Hz, 1H), 7.85 (d, J=8.7 Hz, 1H), 7.59-7.42 (m, 3H), 4.21 (q, J=7.2 Hz, 2H), 3.36 (t, J=7.0 Hz, 2H), 2.78 (t, J=7.0 Hz, 2H), 1.26 (t, J=7.2 Hz, 3H); $^{13}$C NMR (75 MHz, CDCl3) 193.7, 171.6, 135.0, 133.6, 132.9, 129.1, 128.2, 127.9, 127.6, 125.1, 124.3, 60.7, 34.4, 24.8, 14.1; HRMS (ESI$^+$) calcd for [M+H]$^+$ (C$_{16}$H$_{17}$O$_3$S) 289.0898. found 289.0901.

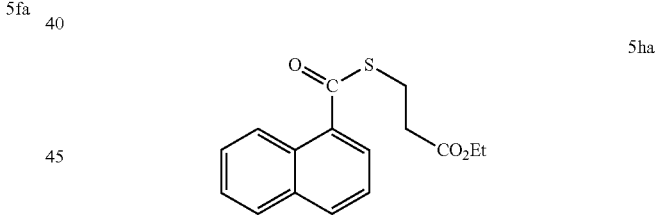

Figure 19:
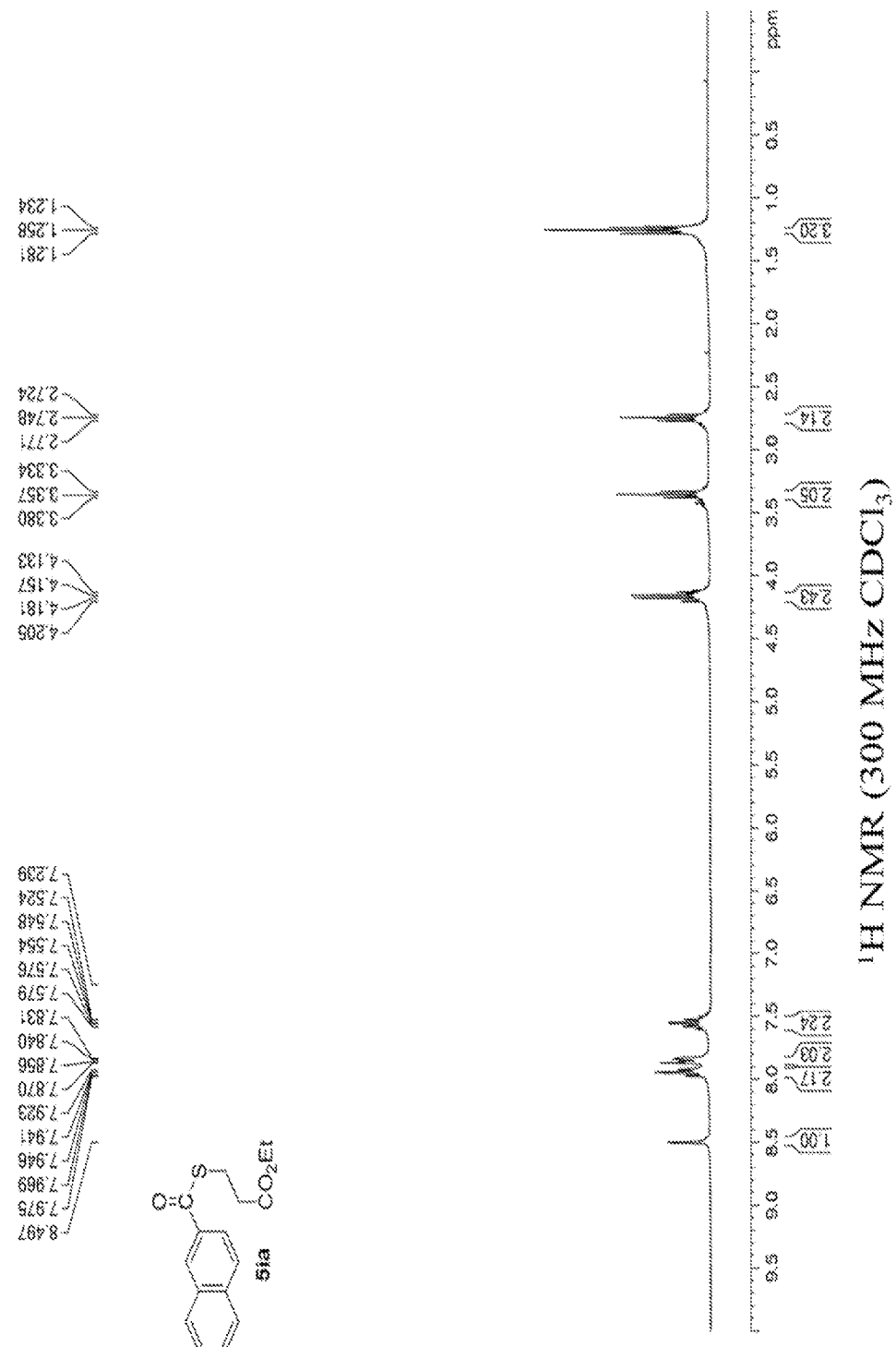
FIG. 19 shows $^1$H NMR spectrum for compound 5ia.
Figure 20:
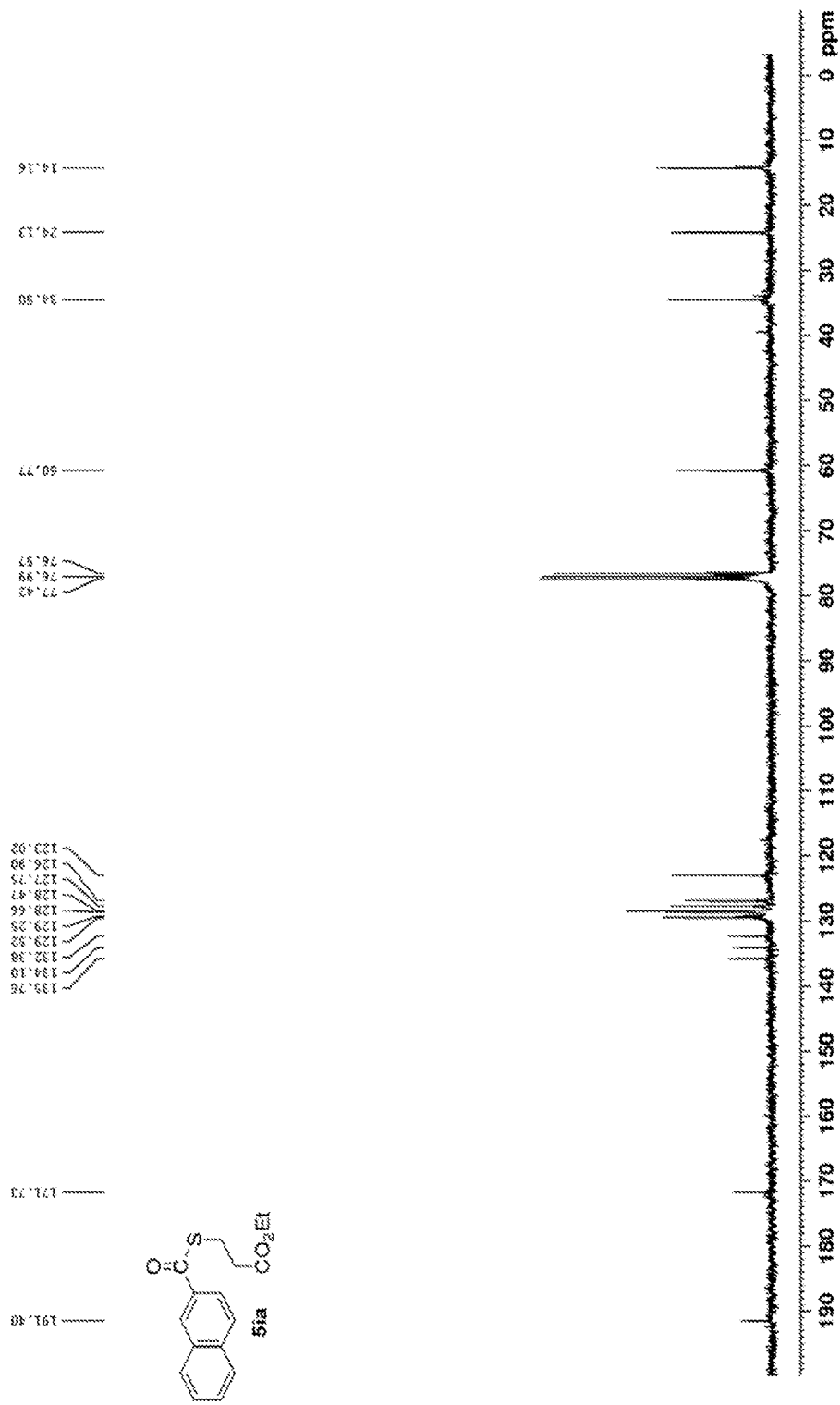
FIG. 20 shows $^{13}$C NMR spectrum for compound 5ia.

5ha 147.5 mg of compound 5ia (0.51 mmol, 52%), which is ethyl 3-(2-naphthoylthio)propanoate, was isolated as a light yellow oil after column chromatography (SiO$_2$:EtOAc/n-hexane, 1:5; R$_f$ 0.72) in the same (or substantially the same) manner as in Example 8, except that 2-naphthoicacid (254.1 mg, 1.47 mmol) was used instead of 1-naphthoic acid, and 98.6 mg of ethylacrylate (0.98 mmol), 336.4 mg of N,N'-diphenylthiourea (0.78 mmol) and 41.8 mg of compound 4 (0.20 mmol) in toluene (5.0 mL) were used. FIG. 19 shows $^1$H NMR spectrum for compound 5ia, and FIG. 20 shows $^{13}$C NMR spectrum for compound 5ia.

$^1$H NMR (300 MHz, CDCl3) δ 8.49 (s, 1H), 7.97-7.92 (m, 2H), 7.87-7.83 (m, 2H), 7.57-7.52 (m, 2H), 4.21 (q, J=7.2 Hz, 2H), 3.35 (t, J=6.9 Hz, 2H), 2.74 (t, J=6.9 Hz, 2H), 1.25 (t, J=7.2 Hz, 3H); $^{13}$C NMR (75 MHz, CDCl3) 191.4, 171.7, 135.7, 134.1, 132.3, 129.5, 129.2, 128.6, 128.4, 127.7, 126.9, 123.0, 60.7, 34.5, 24.1, 14.1; HRMS (ESI$^+$) calcd for [M+H]$^+$ (C$_{16}$H$_{17}$O$_3$S) 289.0898. found 289.0896.

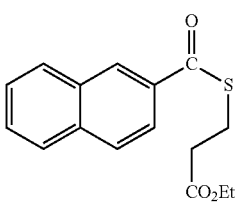

5ia

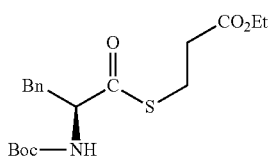

5ka

Example 10

Figure 21:
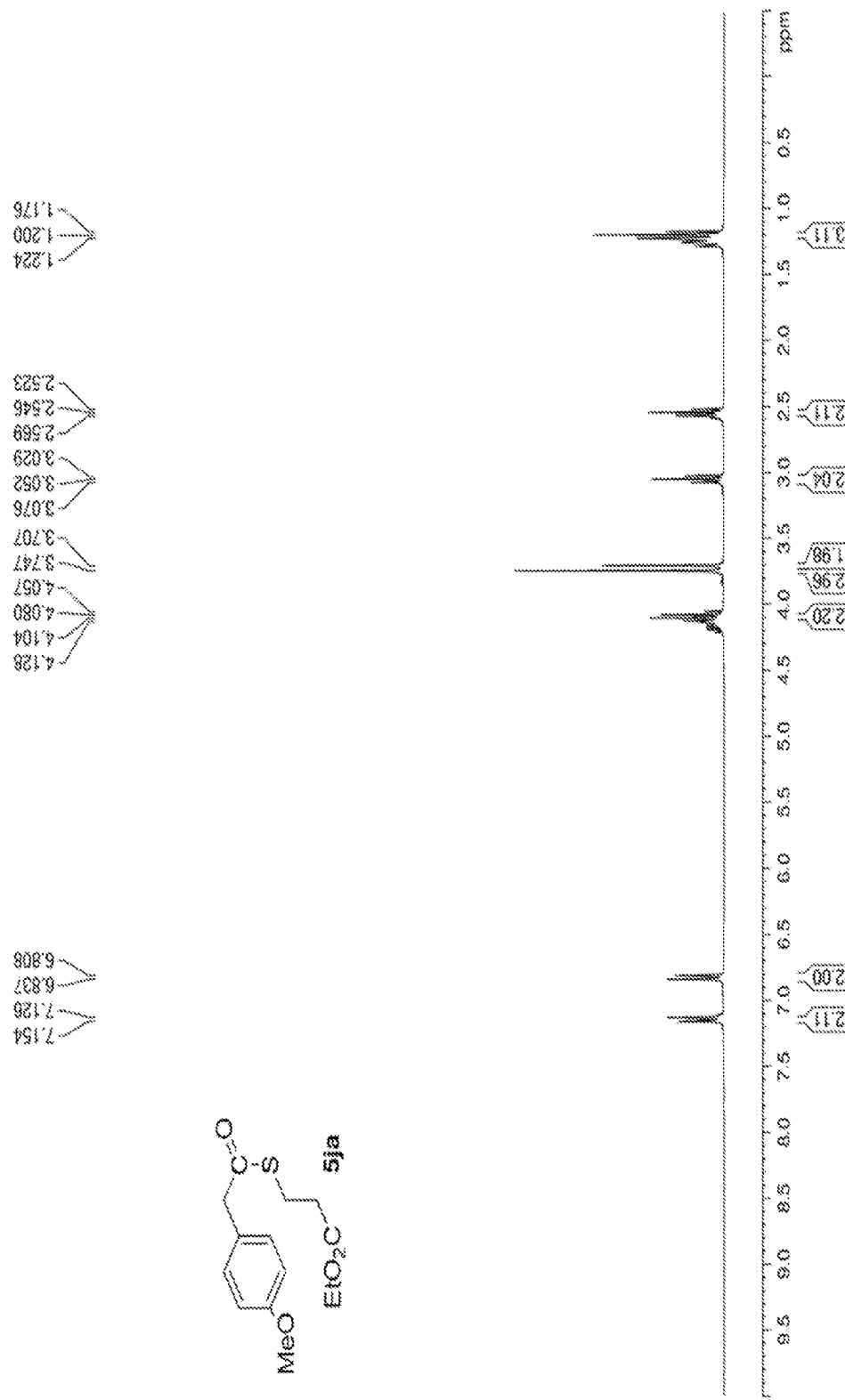
FIG. 21 shows $^1$H NMR spectrum for compound 5ja.
Figure 22:
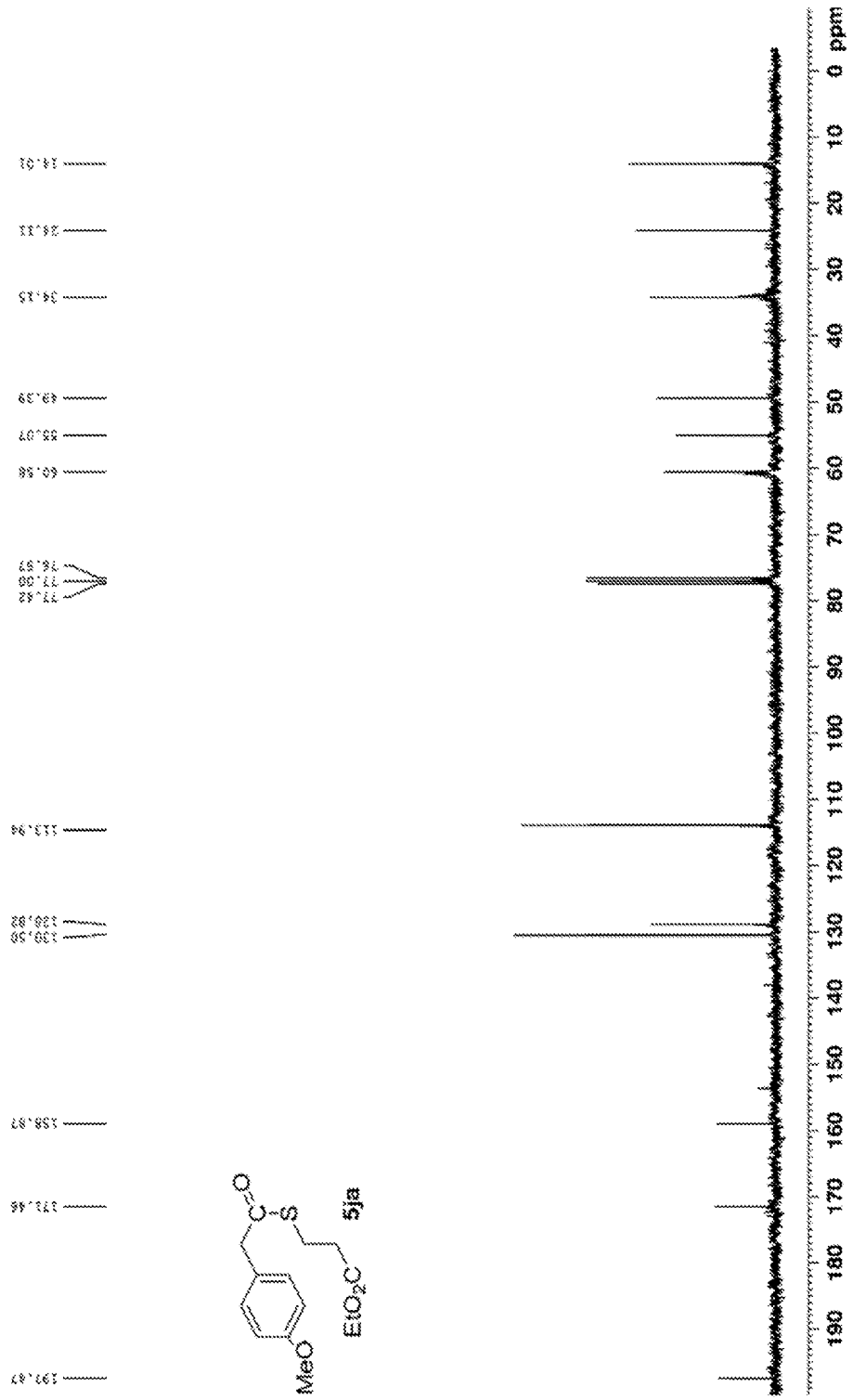
FIG. 22 shows $^{13}$C NMR spectrum for compound 5ja.

171.5 mg of compound 5ja (0.61 mmol, 58%), which is ethyl 3-(2-(4-methoxyphenyl)acetylthio)propanoate, was isolated as a colorless oil after column chromatography (SiO$_2$:EtOAc/n-hexane, 1:4; R$_f$ 0.70) in the same (or substantially the same) manner as in Example 8, except that 4-methoxyphenyl acetic acid (260.8 mg, 1.57 mmol) was used instead of 1-naphthoic acid, and 105.8 mg of ethylacrylate (1.05 mmol), 358.4 mg of N,N'-diphenylthiourea (1.57 mmol) and 43.9 mg of compound 4 (0.21 mmol) in toluene (5.0 mL) were used. FIG. 21 shows $^1$H NMR spectrum for compound 5ja, and FIG. 22 shows $^{13}$C NMR spectrum for compound 5ja.

$^1$H NMR (300 MHz, CDCl3) δ 7.15 (d, J=8.4 Hz, 2H), 6.83 (d, J=8.4 Hz, 2H), 4.12 (q, J=7.2 Hz, 2H), 3.74 (s, 1H), 3.71 (s, 1H), 3.05 (t, J=6.9 Hz, 2H), 2.54 (t, J=6.9 Hz, 2H), 1.20 (t, J=7.2 Hz, 3H); $^{13}$C NMR (75 MHz, CDCl3) 197.4, 171.4, 158.8, 130.5, 128.8, 113.9, 60.5, 55.1, 49.3, 34.1, 24.1, 14.0; HRMS (ESI$^+$) calcd for [M+H]$^+$ (C$_{16}$H$_{17}$O$_3$S) 283.1004. found 283.1013.

Example 12

Figure 25:
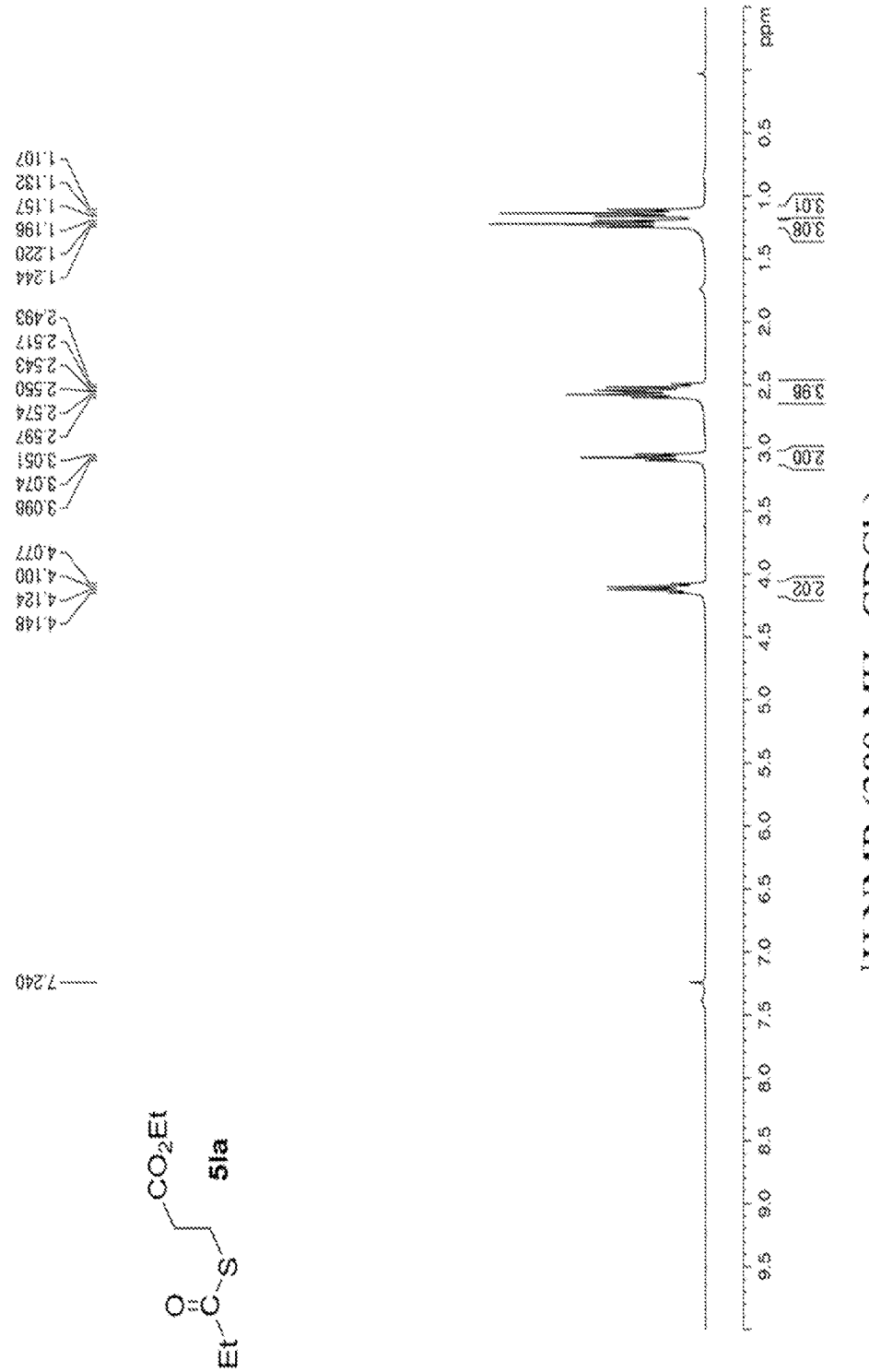
FIG. 25 shows $^1$H NMR spectrum for compound 5la.
Figure 26:
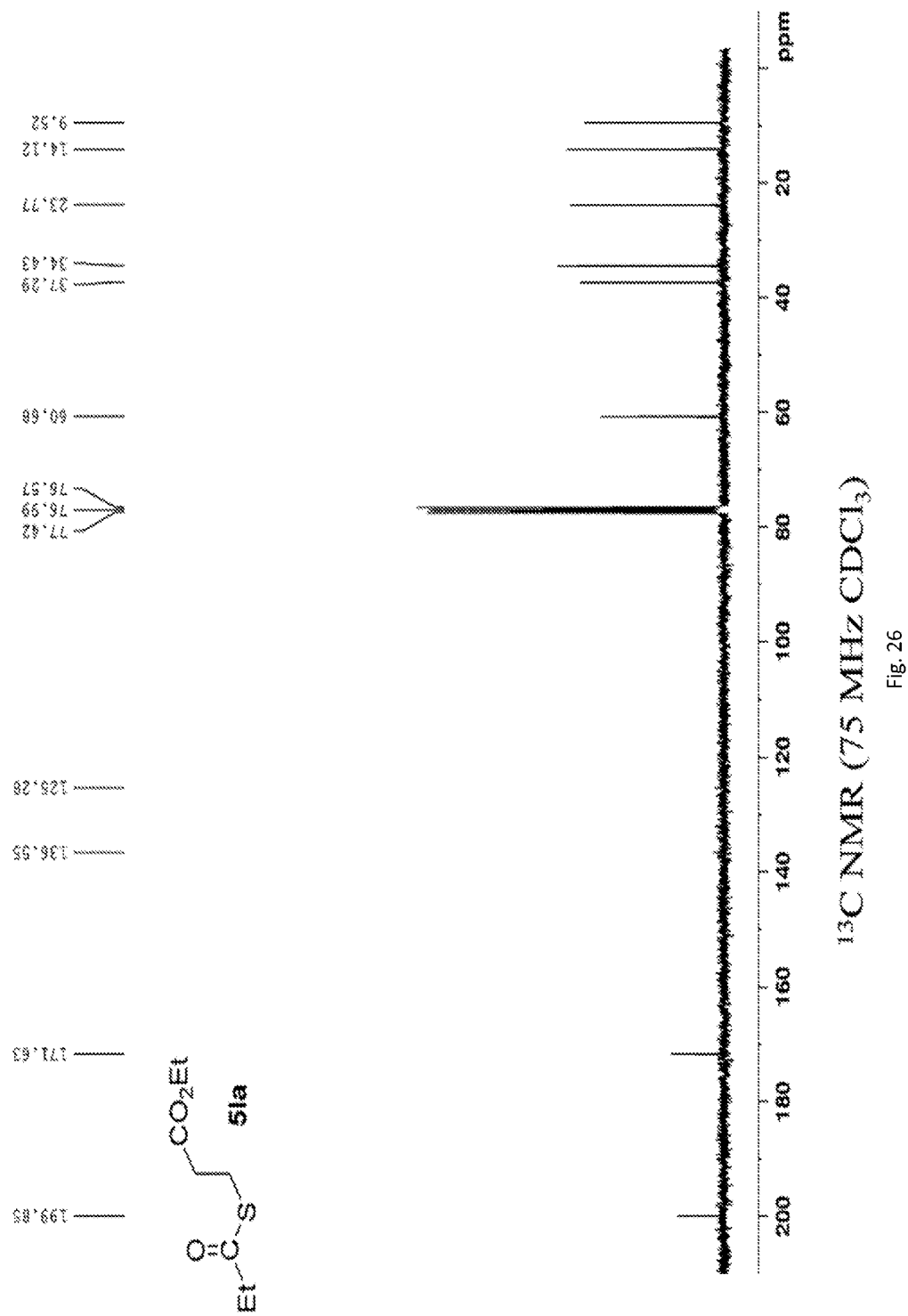
FIG. 26 shows $^{13}$C NMR spectrum for compound 5la.

24.8 mg of compound 5la (0.13 mmol, 25%), which is ethyl 3-(propionylthio)propanoate, was isolated as a colorless oil after column chromatography (SiO$_2$:EtOAc/n-hexane, 1:5; R$_f$ 0.82) in the same (or substantially the same) manner as in Example 1, except that propionic acid (58.1 mg, 0.78 mmol) was used instead of benzoic acid, and 52.4 mg of ethylacrylate (0.52 mmol), 178.9 mg of N,N'-diphenylthiourea (0.78 mmol) and 21.9 mg of compound 4 (0.10 mmol) in toluene (2.5 mL) were used. FIG. 25 shows $^1$H NMR spectrum for compound 5la, and FIG. 26 shows $^{13}$C NMR spectrum for compound 5la.

$^1$H NMR (300 MHz, CDCl3) δ 4.14 (q, J=7.2 Hz, 2H), 3.07 (t, J=7.2 Hz, 2H), 2.59-2.49 (m, 4H), 1.22 (t, J=7.2 Hz, 3H), 1.13 (t, J=7.5 Hz, 3H); $^{13}$C NMR (75 MHz, CDCl3) 199.8, 171.6, 70.6, 37.2, 34.4, 23.7, 14.1, 9.5; HRMS (FAB$^+$) calcd for [M]$^+$ (C$_8$H$_{14}$O$_3$S) 190.0664. found 190.0659.

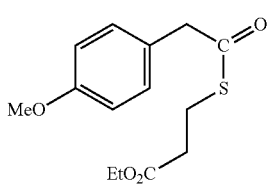

5ja

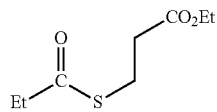

5la

Example 11

Figure 23:
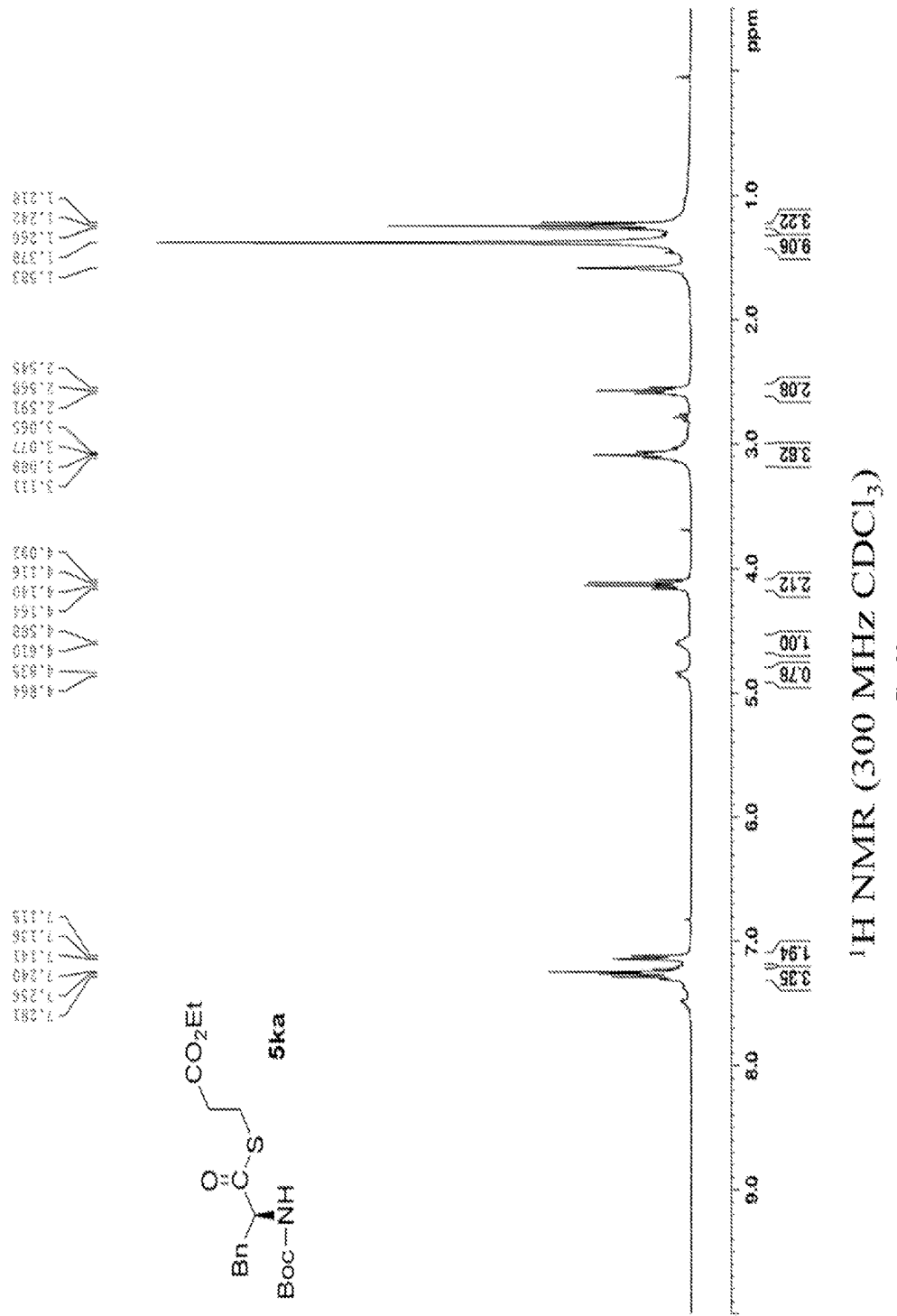
FIG. 23 shows $^1$H NMR spectrum for compound 5ka.
Figure 24:
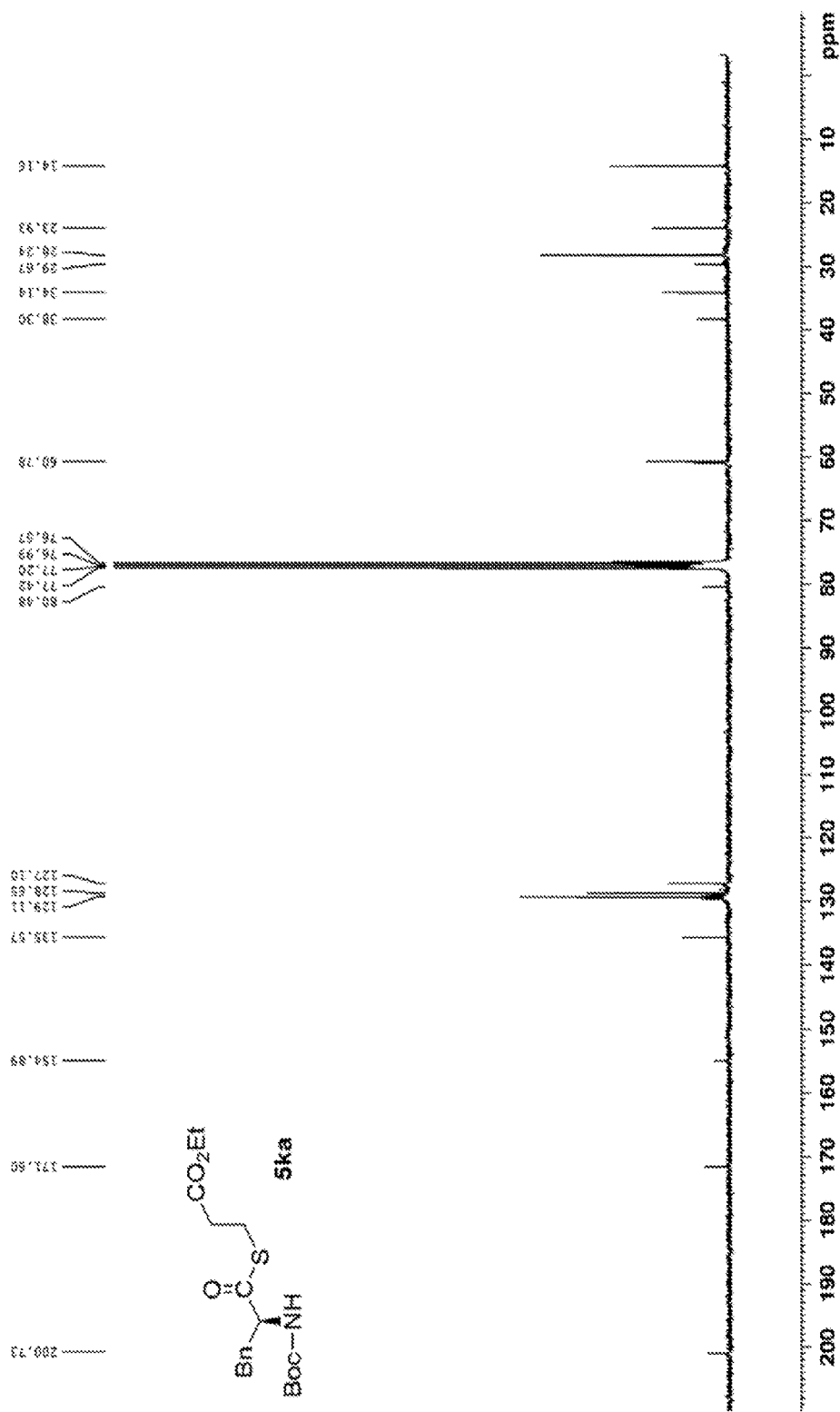
FIG. 24 shows $^{13}$C NMR spectrum for compound 5ka.

77.5 mg of compound 5ka (0.20 mmol, 40%), which is (5)-ethyl 3-(2-(tert-butoxycarbonylamino)-3-phenylpropanoylthio)propanoate, was isolated as a colorless oil after column chromatography (SiO$_2$:EtOAc/n-hexane, 1:5; R$_f$ 0.76) in the same (or substantially the same) manner as in Example 8, except that 2-(tert-butoxycarbonylamino)-3-phenylpropanoic acid (203.2 mg, 0.76 mmol) was used instead of 1-naphthoic acid, and 51.2 mg of ethylacrylate (0.511 mmol), 174.8 mg of N,N'-diphenylthiourea (0.76 mmol) and 21.3 mg of compound 4 (0.10 mmol) in toluene (2.5 mL) were used. FIG. 23 shows $^1$H NMR spectrum for compound 5ka, and FIG. 24 shows $^{13}$C NMR spectrum for compound 5ka.

$^1$H NMR (300 MHz, CDCl3) δ 7.28-7.25 (m, 3H), 7.14 (dd, J=7.8 Hz, J=1.5 Hz, 2H), 4.86 (d, J=8.7 Hz, 1H), 4.61-4.58 (m, 1H), 4.16 (q, J=7.2 Hz, 2H), 3.11-3.06 (m, 4H), 2.56 (t, J=6.9 Hz, 2H), 1.37 (s, 9H), 1.24 (t, J=7.2 Hz, 3H); $^{13}$C NMR (75 MHz, CDCl3) 200.7, 171.6, 154.8, 135.5, 129.1, 128.6, 127.1, 80.4, 60.7, 38.3, 34.1, 29.6, 28.2, 23.9, 14.1; HRMS (ESI$^+$) calcd for [M+H]$^+$ (C$_{19}$H$_{28}$NO$_5$S) 382.1688. found 382.1685.

Example 13

43.1 mg of compound 5ma (0.20 mmol, 40%), which is ethyl 3-(3-methylbutanoylthio)propanoate, was isolated as a colorless oil after column chromatography (SiO$_2$:EtOAc/n-hexane, 1:5; R$_f$ 0.80) in the same (or substantially the same) manner as in Example 1, except that isovaleric acid (76.7 mg, 0.75 mmol) was used instead of benzoic acid, and 50.9 mg of ethylacrylate (0.50 mmol), 171.5 mg of N,N'-diphenylthiourea (0.75 mmol) and 20.9 mg of compound 4 (0.10 mmol) in toluene (2.5 mL) were used.

Figure 28:
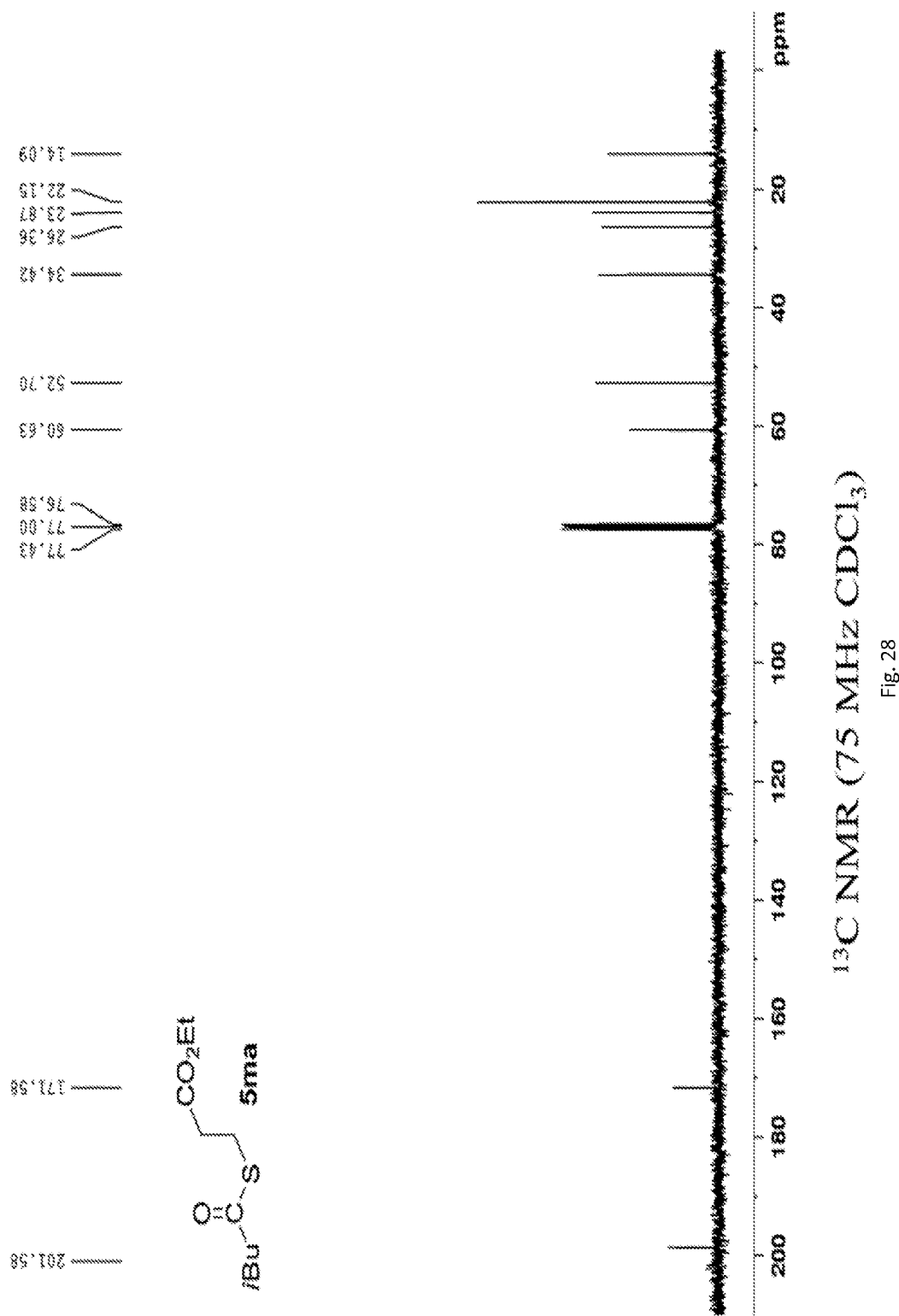
FIG. 28 shows $^{13}$C NMR spectrum for compound 5ma.

When monitoring Example 13 by $^1$H NMR, an intermediate product may be detected, and the intermediate product was reached the highest concentration in 6 hr. Then, the formation of compound 5ma was detected and accompanied with the decreasing of the intermediate product. The intermediate product may be presented by Formula 6 below. FIG. 27 shows $^1$H NMR spectrum for compound 5ma, and FIG. 28 shows $^{13}$C NMR spectrum for compound 5ma.

$^1$H NMR (300 MHz, CDCl3) δ 4.12 (q, J=7.2 Hz, 2H), 3.05 (t, J=6.9 Hz, 2H), 2.55 (t, J=6.9 Hz, 2H), 2.16 (d, J=6.6 Hz, 2H), 2.11-2.02 (m, 1H), 1.20 (t, J=7.2 Hz, 3H), 0.90 (d, J=6.6 Hz, 6H); $^{13}$C NMR (75 MHz, CDCl3) 201.5, 171.5, 60.6, 52.7, 34.4, 26.3, 23.8, 22.1, 14.1; HRMS (ESI$^+$) calcd for [M+H]$^+$ (C$_{10}$H$_{19}$O$_3$S) 219.1055. found 219.1055.

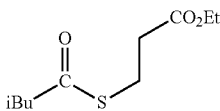

5ma

Figure 29:
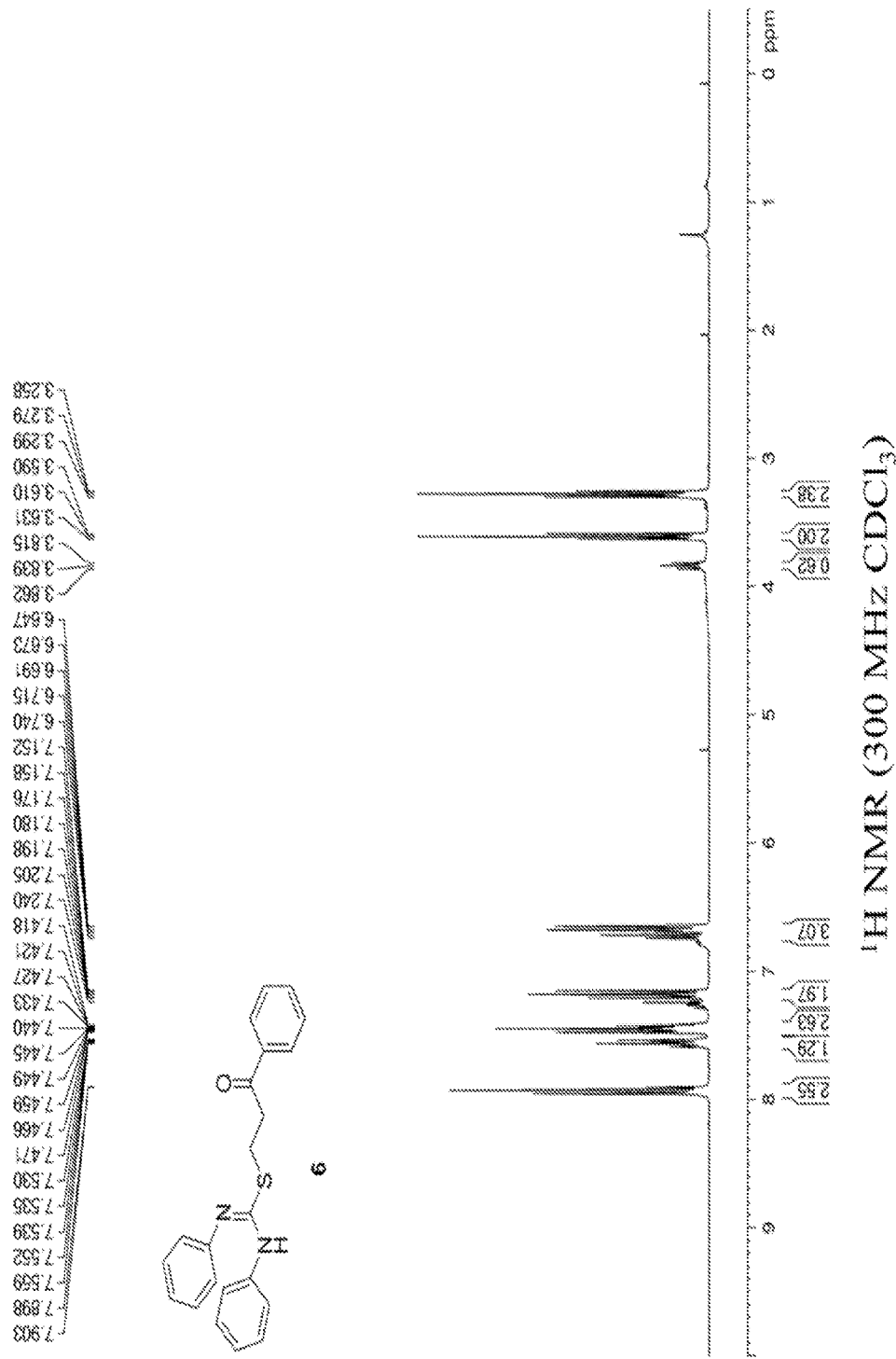
FIG. 29 shows $^1$H NMR spectrum for compound 6.

FIG. 29 shows $^1$H NMR spectrum for compound 6, and FIG. 30 shows $^{13}$C NMR spectrum for compound 6.

Mp104.0-105.0° C.; $^1$H NMR (300 MHz, CDCl3) δ 7.90-7.89 (m, 3H), 7.53-7.41 (m, 5H), 7.19-7.15 (m, 3H), 6.74-6.64 (m, 4H), 3.61 (t, J=6.0 Hz, 2H), 3.27 (t, J=6.0 Hz, 2H); $^{13}$C NMR (75 MHz, CDCl3) 199.1, 147.3, 136.6, 133.2, 129.5, 129.2, 128.5, 127.9, 117.8, 113.2, 38.8, 37.4; HRMS (FAB$^+$) calcd for [M]$^+$ (C$_{22}$H$_{20}$N$_2$OS) 360.1296. found 360.1293.

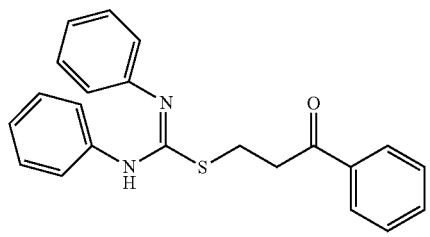

6

Example 14

Figure 32:
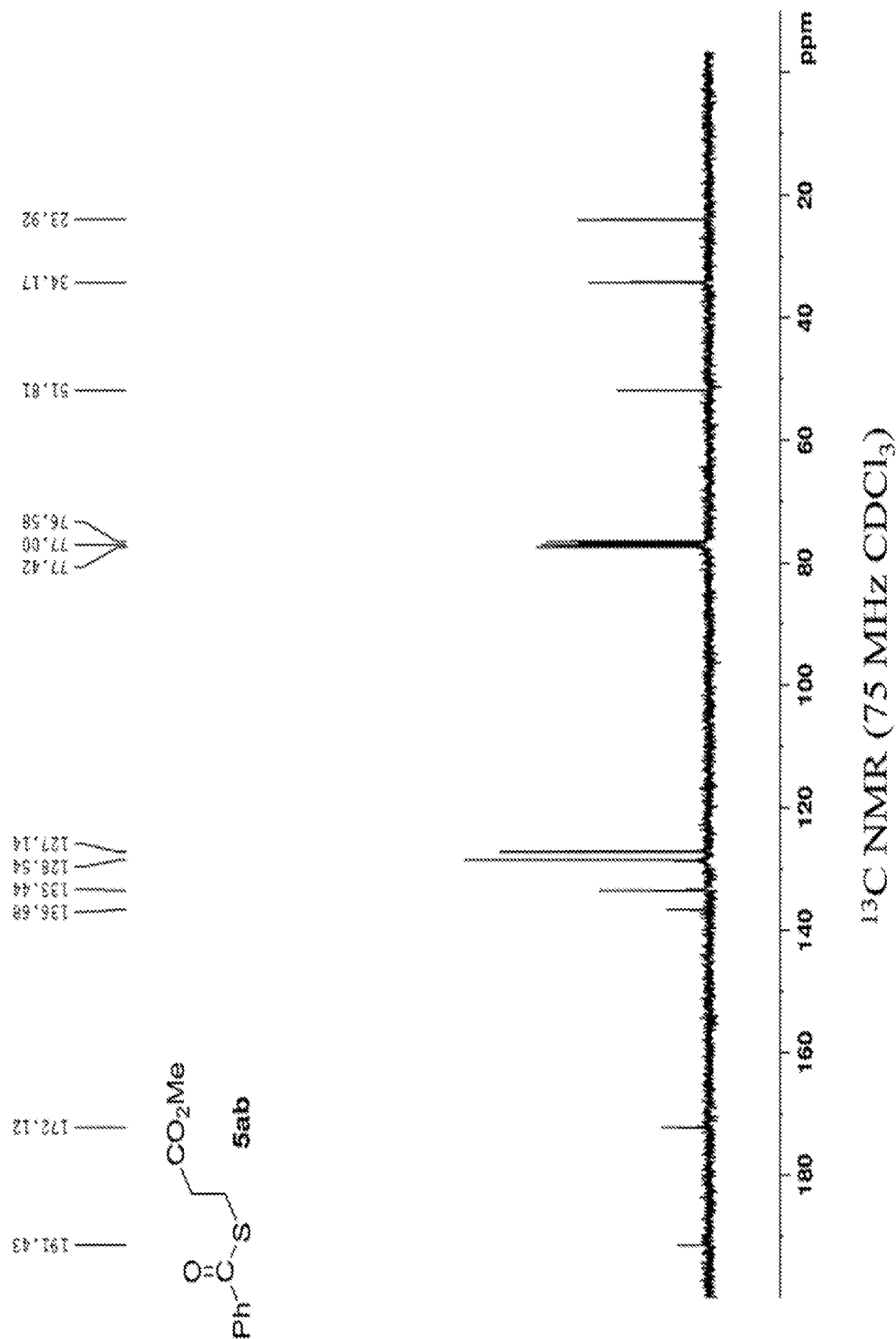
FIG. 32 shows $^{13}$C NMR spectrum for compound 5ab.

68.5 mg of compound 5ab (0.31 mmol, 51%), which is methyl 3-(benzoylthio)propanoate, was isolated as a colorless oil after column chromatography (SiO$_2$:EtOAc/n-hexane, 1:5; R$_f$ 0.75) in the same (or substantially the same) manner as in Example 1, except that methylacrylate (51.8 mg, 0.60 mmol) was used instead of ethylacrylate, and 110.1 mg of benzoic acid (0.90 mmol), 205.7 mg of N,N'-diphenylthiourea (0.90 mmol) and 25.1 mg of compound 4 (0.12 mmol) in toluene (2.5 mL) were used. FIG. 31 shows $^1$H NMR spectrum for compound 5ab, and FIG. 32 shows $^{13}$C NMR spectrum for compound 5ab.

$^1$H NMR (300 MHz, CDCl3) δ 7.92 (d, J=7.2 Hz, 2H), 7.53 (t, J=7.3 Hz, 1H), 7.41 (d, J=7.5 Hz, 2H), 3.67 (s, 3H), 3.28 (t, J=6.9 Hz, 2H), 2.71 (t, J=6.9 Hz, 2H); $^{13}$C NMR (75 MHz, CDCl3) 191.4, 172.1, 136.6, 133.4, 128.5, 127.1, 51.8, 34.1, 23.9; HRMS (ESI$^+$) calcd for [M+H]$^+$ (C$_{11}$H$_{13}$O$_3$S) 225.0585. found 225.0582.

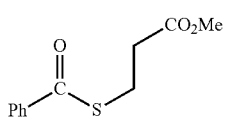

5ab

Example 15

Figure 34:
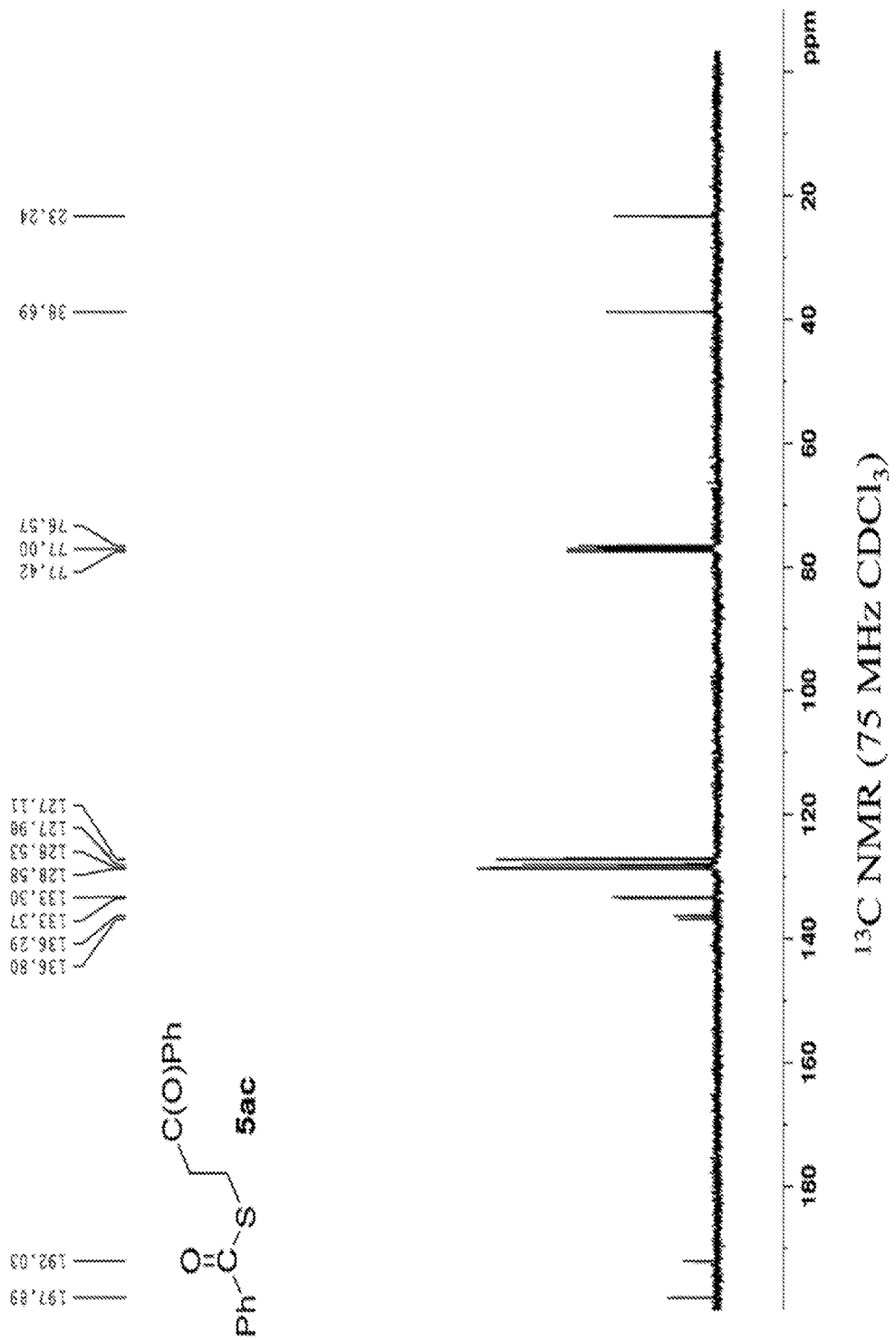
FIG. 34 shows $^{13}$C NMR spectrum for compound 5ac.

18.8 mg of compound 4 (0.09 mmol) used as a catalyst was added to a solution of benzoic acid (83.6 mg, 0.68 mmol), phenyl vinyl ketone (60.5 mg, 0.46 mmol), and N,N'-diphenylthiourea (156.4 mg, 0.68 mmol) in dicholomethane (2.5 mL). The reaction was heated in an oil bath (40° C.) for 48 h, and then the excess solvent was evaporated under vacuum. The crude product was purified by column chromatography (SiO$_2$:EtOAc/n-hexane, 1:5; R$_f$ 0.74), and 76.5 mg of compound 5ac (0.28 mmol, 62%), which is S-3-oxo-3-phenylpropyl benzothioate, was isolated as a colorless solid after column chromatography. FIG. 33 shows $^1$H NMR spectrum for compound 5ac, and FIG. 34 shows $^{13}$C NMR spectrum for compound 5ac.

Mp 48.0-49.0° C.; $^1$H NMR (300 MHz, CDCl3) δ 7.96-7.92 (m, 4H), 7.56-7.51 (m, 2H), 7.46-7.38 (m, 4H), 3.47-3.37 (m, 4H); $^{13}$C NMR (75 MHz, CDCl3) 197.8, 192.0, 136.8, 136.2, 133.4, 133.3, 128.6, 128.5, 127.9, 127.1, 38.6, 23.2; HRMS (ESI$^+$) calcd for [M+H]$^+$ (C$_{16}$H$_{15}$O$_2$S) 271.0793. found 271.0791.

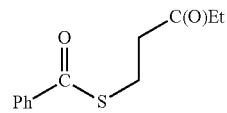

5ac

Example 16

Figure 36:
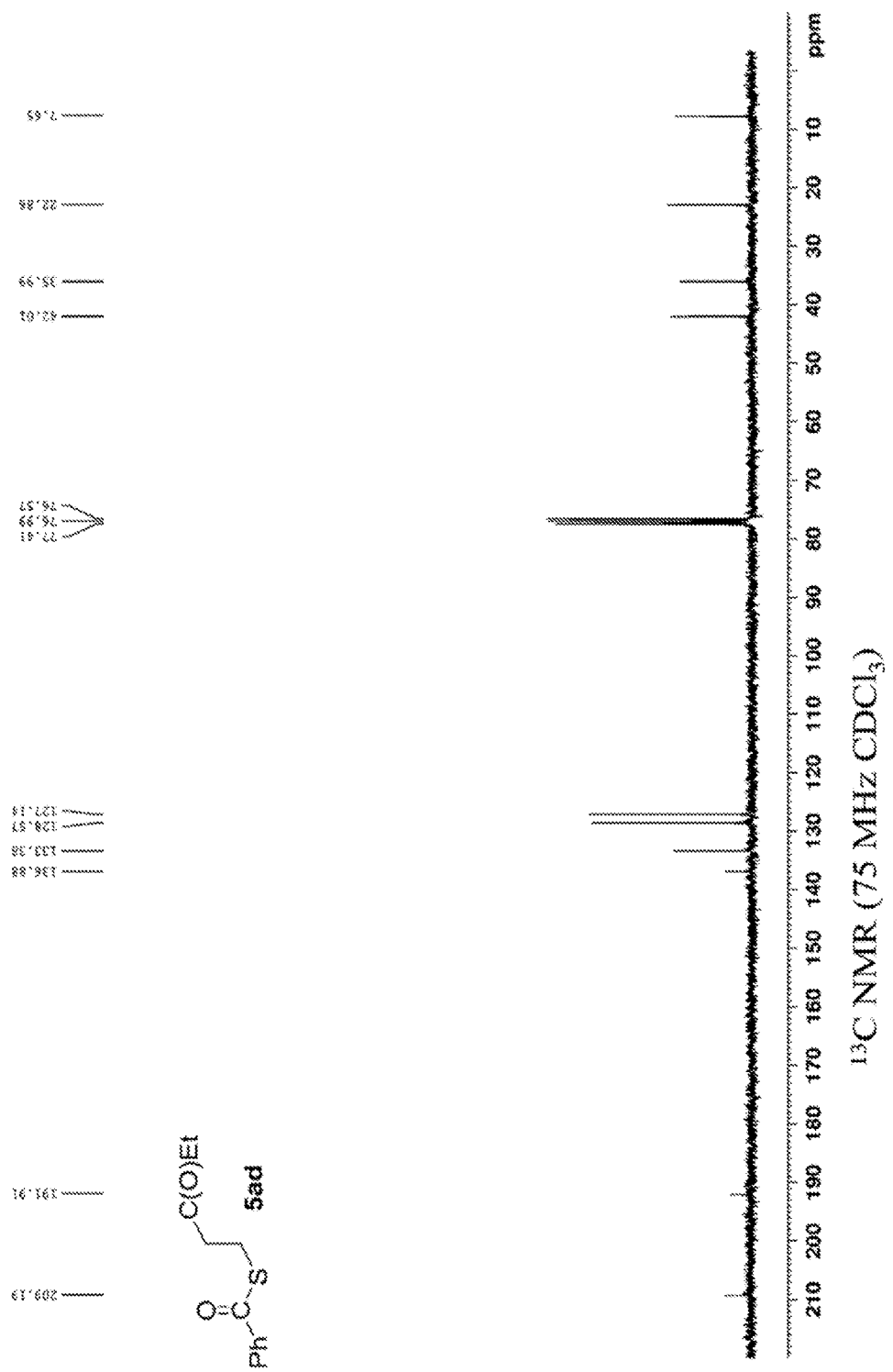
FIG. 36 shows $^{13}$C NMR spectrum for compound 5ad.

112.9 mg of compound 5ad (0.51 mmol, 42%), which is S-3-oxopentyl benzothioate, was isolated as a colorless oil after column chromatography (SiO$_2$:EtOAc/n-hexane, 1:5; R$_f$ 0.78) in the same (or substantially the same) manner as in Example 15, except that pent-1-en-3-one (101.6 mg, 1.21 mmol) was used instead of phenyl vinyl ketone, and 221.1 mg of benzoic acid (1.81 mmol), 413.2 mg of N,N'-diphenylthiourea (1.81 mmol) and 50.2 mg of compound 4 (0.24 mmol) in dichloromethane (5.0 mL) were used. FIG. 35 shows $^1$H NMR spectrum for compound 5ad, and FIG. 36 shows $^{13}$C NMR spectrum for compound 5ad.

$^1$H NMR (300 MHz, CDCl3) δ 7.93 (dd, J=7.5 Hz, J=0.6 Hz, 2H), 7.56 (dt, J=7.8 Hz, J=0.9 Hz, 1H), 7.41 (t, J=7.8 Hz, 2H); $^{13}$C NMR (75 MHz, CDCl3) 209.1, 191.9, 136.8, 133.3, 128.5, 127.1, 42.0, 35.9, 22.8, 7.6; HRMS (ESI$^+$) calcd for [M+H]$^+$ (C$_{12}$H$_{15}$O$_2$S) 223.0793. found 223.0790.

5ad

Example 17

Figure 37:
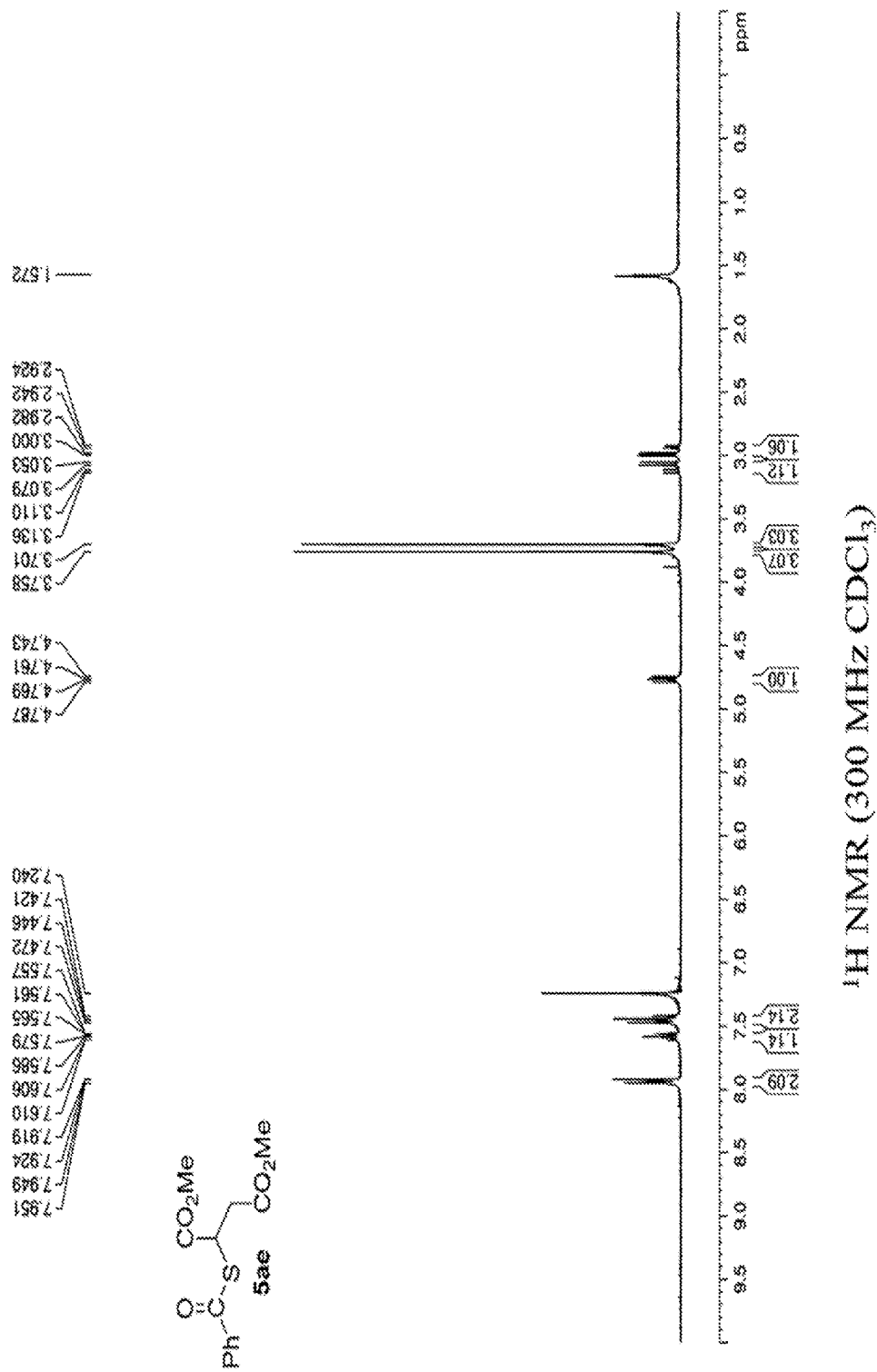
FIG. 37 shows $^1$H NMR spectrum for compound 5ae.
Figure 38:
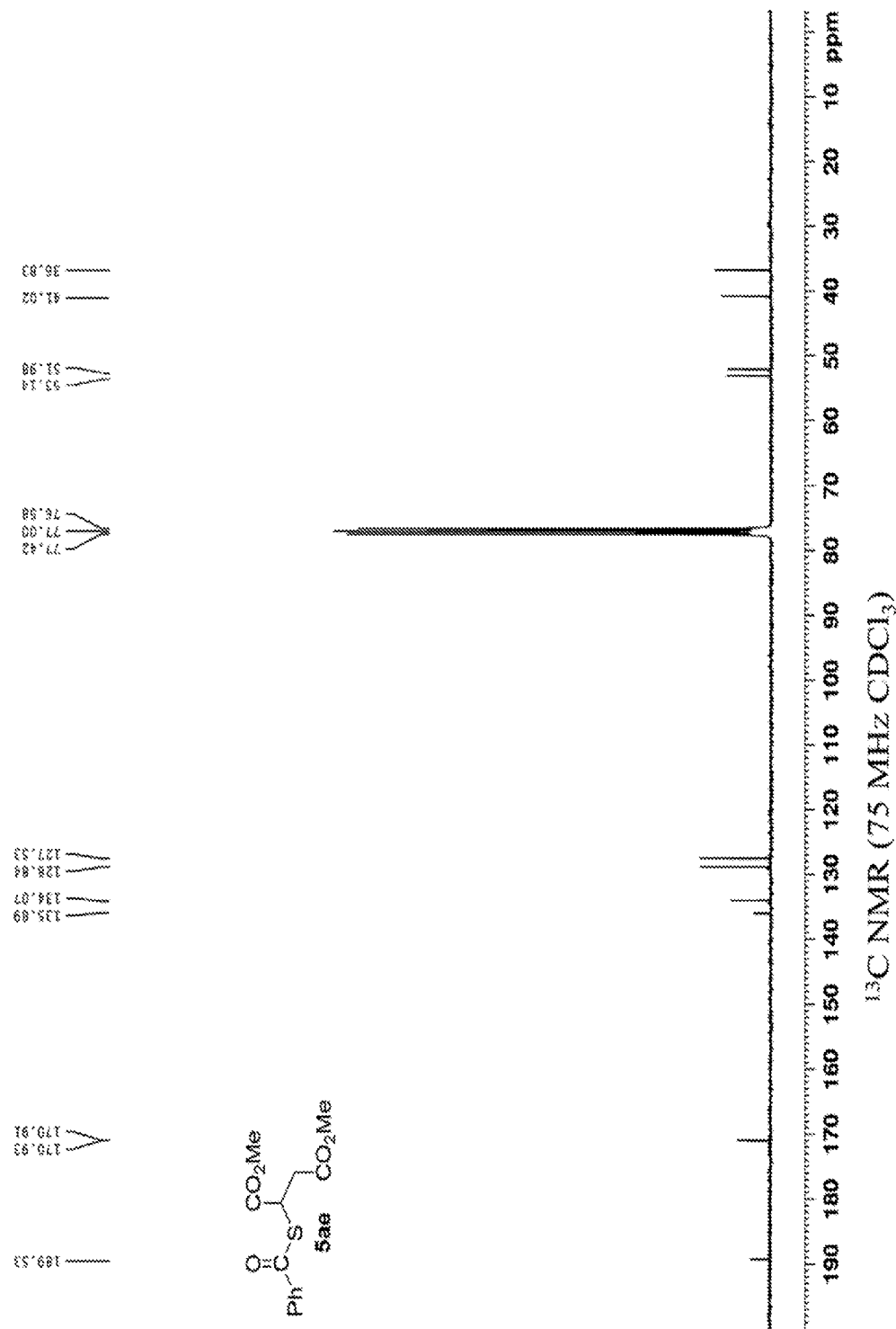
FIG. 38 shows $^{13}$C NMR spectrum for compound 5ae.

131.2 mg of compound 5ae (0.55 mmol, 55%), which is dimethyl 2-(benzoylthio)succinate, was isolated as a colorless oil after column chromatography (SiO$_2$:EtOAc/n-hexane, 1:5; R$_f$ 0.75) in the same (or substantially the same) manner as in Example 8, except that dimethylfumarate (100.4 mg, 0.69 mmol) was used instead of ethylacrylate, benzoic acid (127.5 mg, 1.04 mmol) was used instead of 1-naphthoic acid, and 237.4 mg of N,N'-diphenylthiourea (1.04 mmol) and 29.3 mg of compound 4 (0.14 mmol) in toluene (5.0 mL) were used. FIG. 37 shows $^1$H NMR spectrum for compound 5ae, and FIG. 38 shows $^{13}$C NMR spectrum for compound 5ae.

$^1$H NMR (300 MHz, CDCl3) δ 7.94 (dd, J=7.8 Hz, J=0.9 Hz, 2H), 7.56 (dt, J=7.5 Hz, J=0.9 Hz, 1H), 7.41 (dt, J=7.8 Hz, J=1.8 Hz, 2H), 4.78-4.74 (m, 1H), 3.75 (s, 3H), 3.70 (s,

3H), 3.13-2.92 (m, 2H); $^{13}$C NMR (75 MHz, CDCl3) 189.2, 170.9, 170.9, 135.8, 134.0, 128.7, 127.4, 53.1, 51.9, 41.0, 36.8, 29.8; HRMS (ESI$^+$) calcd for [M+H]$^+$ (C$_{13}$H$_{15}$O$_5$S) 283.0640. found 283.0638.

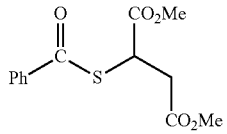

5ae

Example 18

Figure 40:
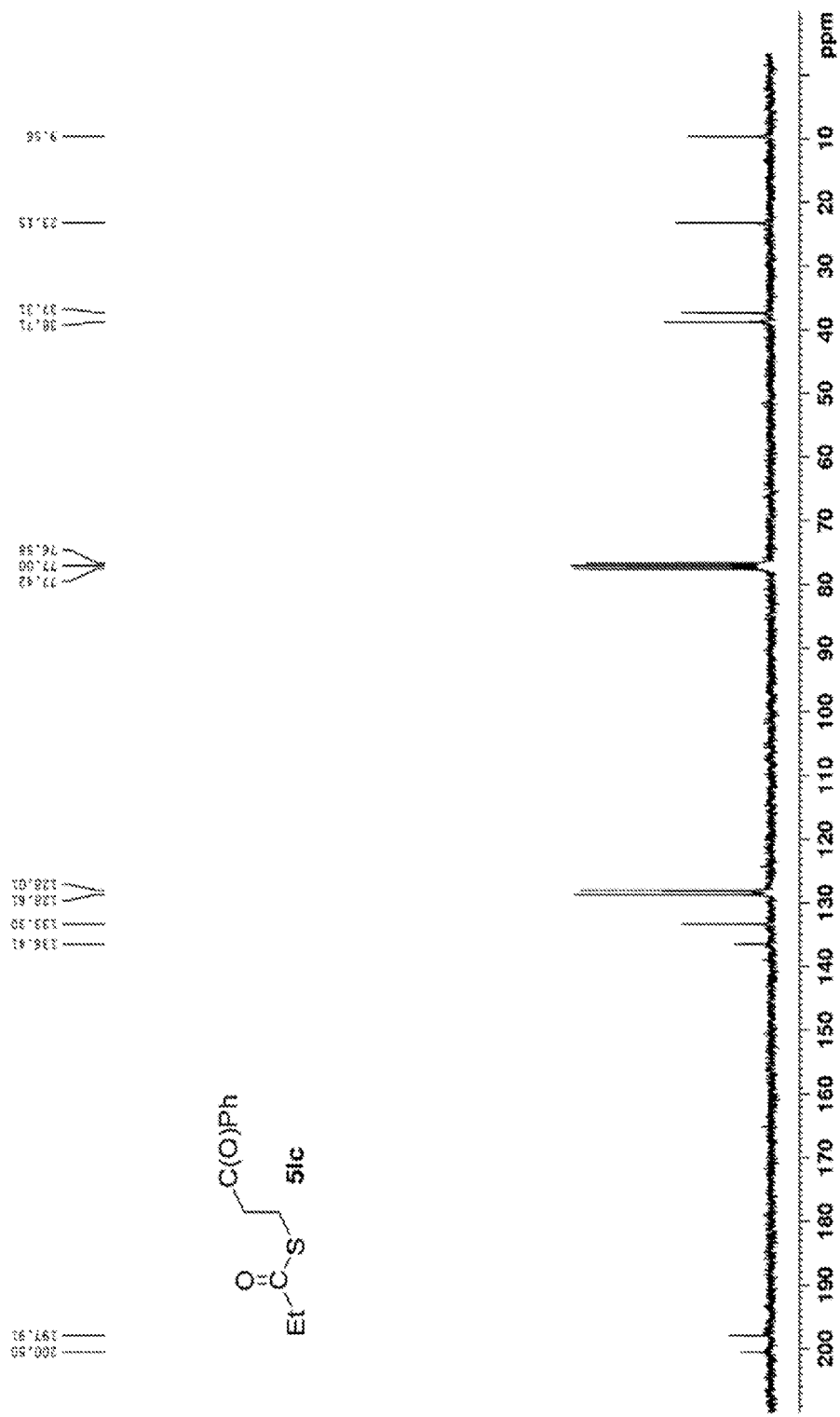
FIG. 40 shows $^{13}$C NMR spectrum for compound 5lc.
Figure 42:
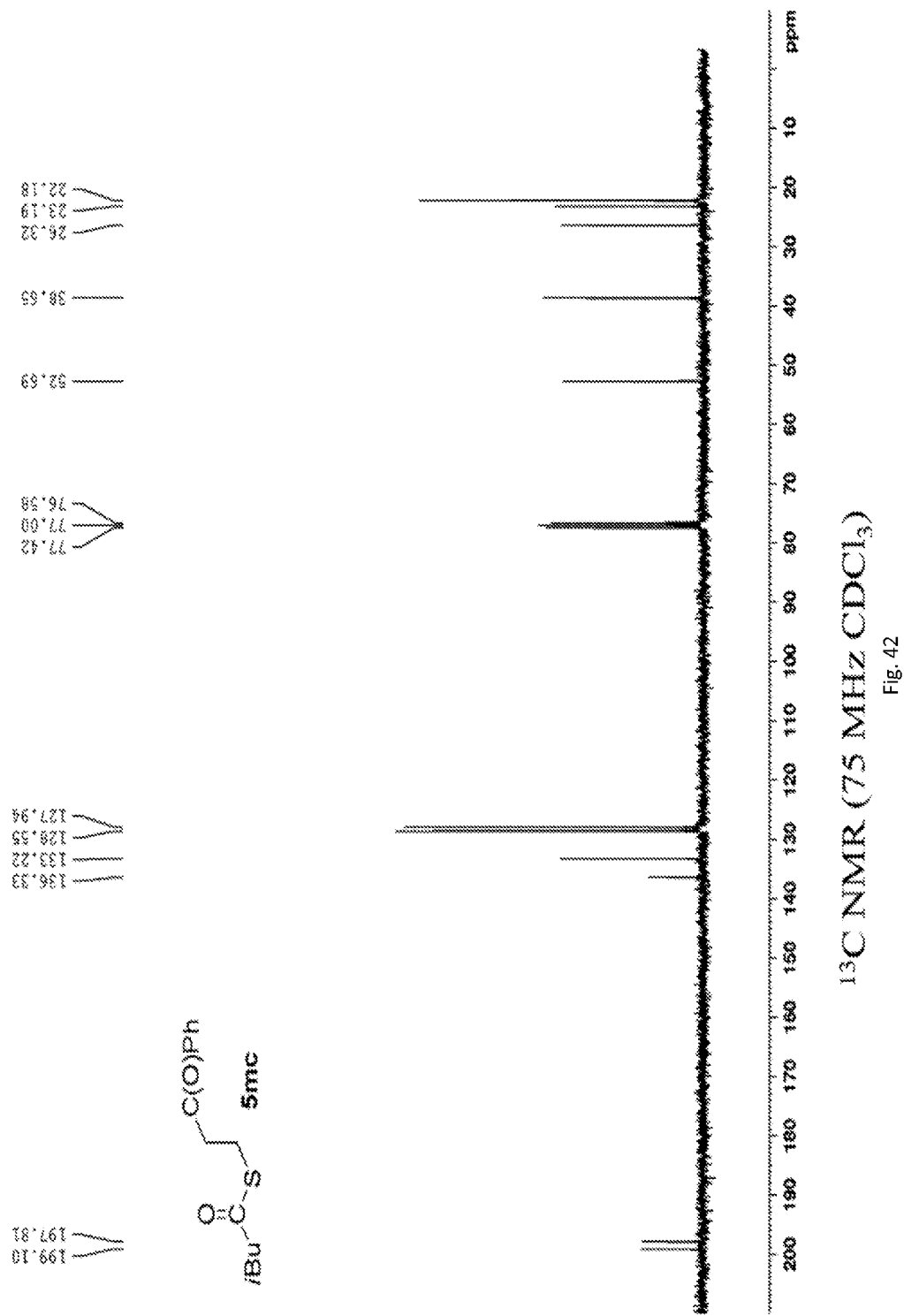
FIG. 42 shows $^{13}$C NMR spectrum for compound 5mc.

38.2 mg of compound 5lc (0.17 mmol, 45%), which is S-3-oxo-3-phenylpropyl propanethioate, was isolated as a colorless oil after column chromatography (SiO$_2$:EtOAc/n-hexane, 1:5; R$_f$ 0.75) in the same (or substantially the same) manner as in Example 15, except that 1-phenylprop-2-en-1-one (50.8 mg, 0.38 mmol) was used instead of phenyl vinyl ketone, propionic acid (42.6 mg, 0.57 mmol) was used instead of benzoic acid, and 131.5 mg of N,N'-diphenylthiourea (0.57 mmol) and 24.1 mg of compound 4 (0.11 mmol) in dichloromethane (2.5 mL) were used. FIG. 39 shows $^1$H NMR spectrum for compound 5lc, and FIG. 40 shows $^{13}$C NMR spectrum for compound 5lc.

$^1$H NMR (300 MHz, CDCl3) δ 7.94 (dd, J=7.2 Hz, J=1.5 Hz, 2H), 7.57 (dt, J=7.2 Hz, J=1.5 Hz, 1H), 7.46 (dt, J=7.2 Hz, J=1.5 Hz, 2H), 3.32-3.19 (m, 4H), 2.58 (q, J=7.5 Hz, 2H), 1.15 (t, J=7.5 Hz, 3H); $^{13}$C NMR (75 MHz, CDCl3) 200.5, 197.9, 136.4, 133.3, 128.6, 128.0, 38.7, 37.3, 23.1, 9.5; HRMS (ESI$^+$) calcd for [M+H]$^+$ (C$_{12}$H$_{15}$O$_2$S) 223.0793. found 223.0789.

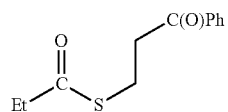

5lc

Example 19

63.1 mg of compound 5mc (0.25 mmol, 66%), which is S-3-oxo-3-phenylpropyl 3-methylbutanethioate, was isolated as a colorless solid after column chromatography (SiO$_2$:EtOAc/n-hexane, 1:5; R$_f$ 0.76) in the same (or substantially the same) manner as in Example 1, except that 1-phenylprop-2-en-1-one (50.2 mg, 0.38 mmol) was used instead of ethylacrylate, isovaleric acid (58.1 mg, 0.57 mmol) was used instead of benzoic acid, and 129.6 mg of N,N'-diphenylthiourea (0.57 mmol) and 23.8 mg of compound 4 (0.11 mmol) in toluene (2.5 mL) were used.

Mp 44.0-45.0° C.; $^1$H NMR (300 MHz, CDCl3) δ 7.92 (d, J=7.8 Hz, 2H), 7.52 (t, J=7.5 Hz, 1H), 7.41 (t, J=7.5 Hz, 2H), 3.28-3.18 (m, 4H), 2.39 (d, J=7.2 Hz, 2H), 2.16-2.07 (m, 1H), 1.15 (t, J=7.5 Hz, 3H), 0.91 (d, J=6.6 Hz, 6H); $^{13}$C NMR (75 MHz, CDCl3) 199.1, 197.8, 136.3, 133.2, 128.5, 127.9, 52.6, 38.6, 26.3, 23.1, 22.1; HRMS (ESI$^+$) calcd for [M+H]$^+$ (C$_{14}$H$_{19}$O$_2$S) 251.1106. found 251.1102.

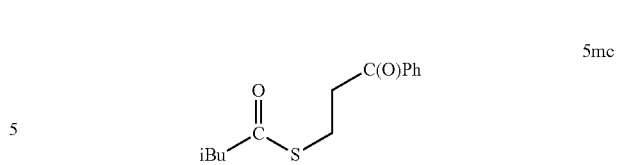

5mc

Example 20

Figure 43:
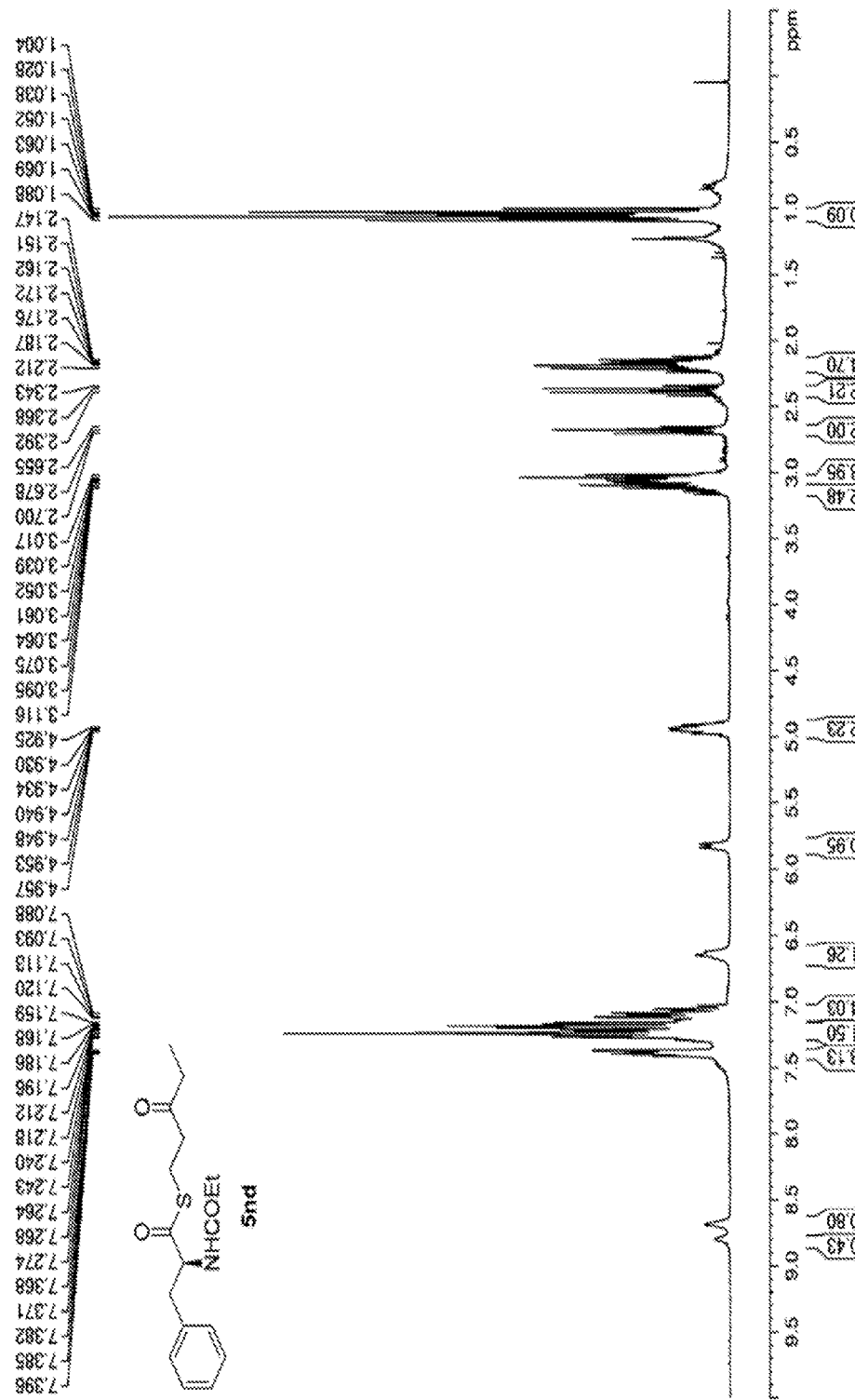
FIG. 43 shows $^1$H NMR spectrum for compound 5nd.
Figure 44:
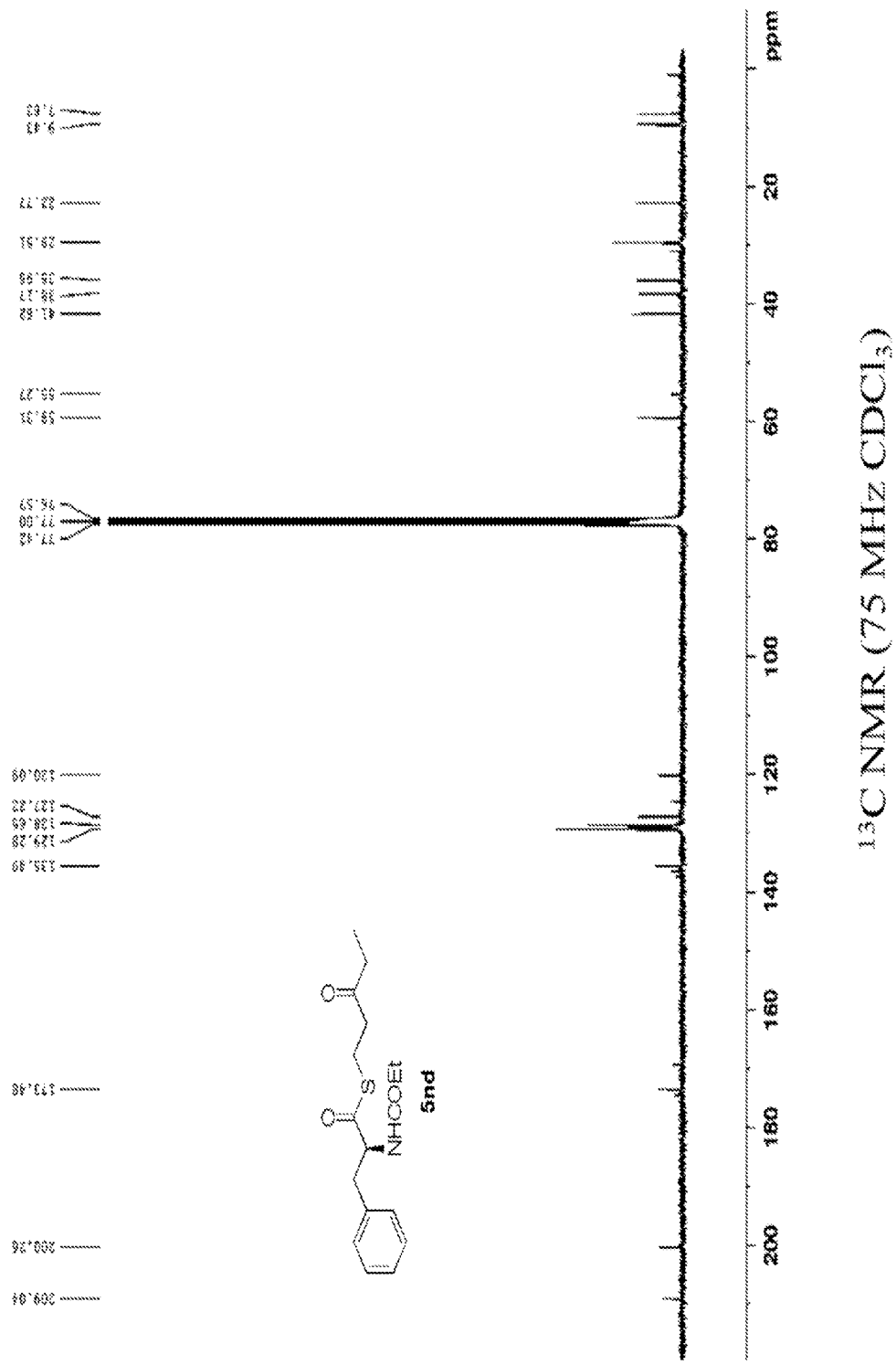
FIG. 44 shows $^{13}$C NMR spectrum for compound 5nd.

64.5 mg of compound 5nd (0.20 mmol, 34%), which is (S)—S-3-Oxopentyl 3-phenyl-2-propionamidopropanethioate, was isolated as a colorless solid after column chromatography (SiO$_2$:EtOAc/n-hexane, 2:1; R$_f$ 0.33) in the same (or substantially the same) manner as in Example 8, except that 1-phenylprop-2-en-1-one (49.6 mg, 0.59 mmol) was used instead of ethylacrylate, (S)-3-phenyl-2-propionamidopropanoic acid (194.7 mg, 0.88 mmol) was used instead of 1-naphthoic acid, and 200.9 mg of N,N'-diphenylthiourea (0.88 mmol) and 25.2 mg of compound 4 (0.12 mmol) in toluene (2.0 mL) were used. FIG. 43 shows $^1$H NMR spectrum for compound 5nd, and FIG. 44 shows $^{13}$C NMR spectrum for compound 5nd.

$^1$H NMR (500 MHz, CDCl3) δ 7.39-7.34 (m, 5H), 6.65 (br, 1H), 4.97-4.89 (m, 1H), 3.11-2.97 (m, 2H), 2.68 (t, J=6.6 Hz, 2H), 2.41 (q, J=7.2 Hz, 2H), 2.21-2.14 (m, 4H), 1.09-1.01 (m, 6H); HRMS (ESI$^+$) calcd for [M+Na]$^+$ (C17H23NO3SNa) 344.1296. found 344.1290.

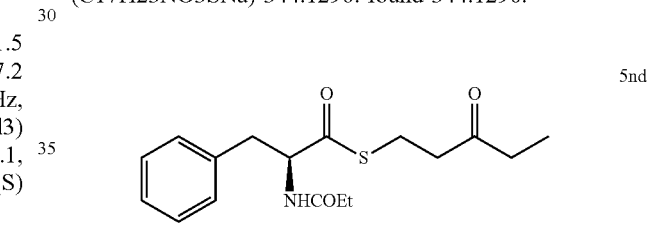

5nd

The following are examples of synthesizing the thioesters according to Reaction Scheme 2 of the present invention, by using compound 4 prepared above as a catalyst.

Example 21

Synthesis of Compound 6

N,N'-diphenylthiourea (26.2 mg, 0.115 mmol) was added to a solution of 1-phenylprop-2-en-1-one (15.2 mg, 0.115 mmol) in toluene (0.5 mL). The reaction was heated in an oil bath (80° C.) for 5 h, and then the excess solvent was evaporated under vacuum. The crude product was purified by column chromatography (SiO$_2$:EtOAc/n-hexane, 1:4; R$_f$ 0.62) to give the compound 6 (29.5 mg, 0.081 mmol, 71%) as a yellow solid. Compound 6 is the same as the compound 6 detected as an intermediate in the synthesis of compound 5ma of Example 13 by $^1$H NMR, therefore, the description of compound 6 is omitted.

Synthesis of Thioester 4.8 mg of compound 4 (0.023 mmol), used as a catalyst, and 11.7 mg isovaleric acid (0.115 mmol) were added to a solution of compound 6 (26.2 mg, 0.115 mmol) in toluene (0.5 mL). The reaction was heated at 80° C. for 16 h. The crude product was purified by column chromatography (SiO$_2$:EtOAc/n-hexane, 1:5; R$_f$ 0.76), and 21.6 mg of compound 5mc (0.086 mmol, 75%) was obtained as a colorless solid. The compound 5mc is the same as the compound in Example 19, therefore, the description of compound 5mc is omitted.

The carboxylic acid, the Michael acceptor, and the thioester compounds synthesized in Examples 1 to 20 and comparative example 1 are shown in table 1 below.

TABLE 1

Thioesterification of Carboxylic Acids[a]

| | Carboxylic acid | Michael acceptor | thioester | yield (%)[b] |
|---|---|---|---|---|
| EXP. 1 | 1a (PhCO₂H) | 2a (CH₂=CHCO₂Et) | 5a (Ph-C(O)-S-CH₂CH₂-CO₂Et) | 80 (55) |
| EXP. 2 | 1b (2-methylbenzoic acid) | 2a | 5ba | 84 (60) |
| EXP. 3 | 1c (3,4-dimethylbenzoic acid) | 2a | 5ca | 72 (55) |
| EXP. 4 | 1d (2,6-dimethylbenzoic acid) | 2a | 5da | 68 (52) |
| EXP. 5 | 1e (4-methoxybenzoic acid) | 2a | 5ea | 81 (62) |
| EXP. 6 | 1f (4-nitrobenzoic acid) | 2a | 5fa | 60 (41) |

TABLE 1-continued
Thioesterification of Carboxylic Acids[a]
| | Carboxylic acid | Michael acceptor | thioester | yield (%)[b] |
|---|---|---|---|---|
| EXP. 7 | 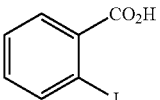<br>1g | 2a | 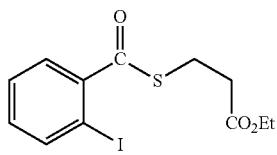<br>5ga | 52 (30) |
| EXP. 8[c] | 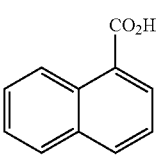<br>1h | 2a | 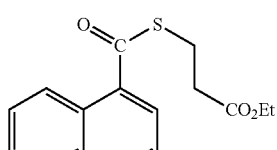<br>5ha | 70 (46) |
| EXP. 9[c] | 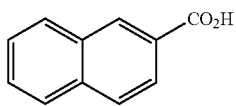<br>1i | 2a | 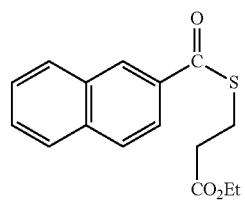<br>5ia | 75 (52) |
| EXP. 10[c] | 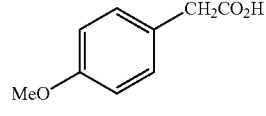<br>1j | 2a | 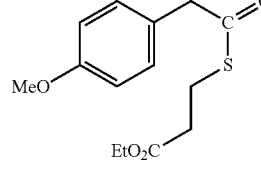<br>5ja | 80 (58) |
| EXP. 11[c] | 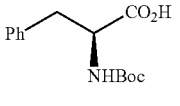<br>1k | 2a | 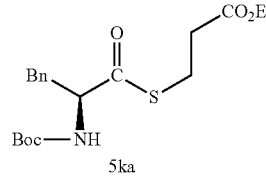<br>5ka | 65 (40) |
| EXP. 12 | CH$_3$CH$_2$CO$_2$H<br>1l | 2a | 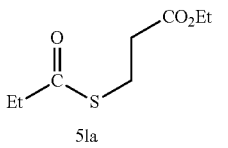<br>5la | 50 (25) |
| EXP. 13 | 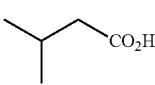<br>1m | 2a | 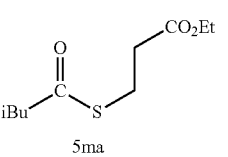<br>5ma | 64 (40) |

TABLE 1-continued

Thioesterification of Carboxylic Acids[a]

| | Carboxylic acid | Michael acceptor | thioester | yield (%)[b] |
|---|---|---|---|---|
| EXP. 14 | PhCO₂H (1a) | CH₂=CH-CO₂Me (2b) | Ph-C(O)-S-CH₂CH₂-CO₂Me (5ab) | 75 (51) |
| EXP. 15[d] | 1a | CH₂=CH-C(O)Ph (2c) | Ph-C(O)-S-CH₂CH₂-C(O)Ph (5ac) | 85 (62) |
| EXP. 16[d] | 1a | CH₂=CH-C(O)Et (2d) | Ph-C(O)-S-CH₂CH₂-C(O)Et (5ad) | 60 (42) |
| EXP. 17[c] | 1a | MeO₂C-CH=CH-CO₂Me (2e) | Ph-C(O)-S-CH(CO₂Me)-CH₂-CO₂Me (5ae) | 46 (20) |
| EXP. 18[d] | 1l | 2c | Et-C(O)-S-CH₂CH₂-C(O)Ph (5lc) | 70 (45) |
| EXP. 19 | 1m | 2c | iBu-C(O)-S-CH₂CH₂-C(O)Ph (5mc) | 85 (66) |
| EXP. 20 | Bn-CH(NHCOEt)-CO₂H (1n) | 2d | Bn-CH(NHCOEt)-C(O)-S-CH₂CH₂-COEt (5nd) | 55 (35) |

[a] reaction conducted in toluene, 80° C., 24 h, N,N'-diphenylthiourea was applied.
[b] yield determined by 1H NMR; isolated yields shown in parentheses.
[c] reaction conducted in toluene, 80° C., 48 h
[d] reaction conducted in CH2Cl2, 40° C., 40 h.

Referring to Table 1, by using the compound represented by Formula I as a catalyst, the thioesters may be synthesized without a thiol, activating agent and base, and the method for synthesizing of thioesters is a one-pot synthesis.

Further, referring to Example 21, by using the compound represented by Formula I as a catalyst, the thioesters may be synthesized by compound 6 and carboxylic acid compounds, without a thiol, activating agent and base.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. A method of synthesizing thioesters using a compound as a catalyst, the compound represented by Formula I below:

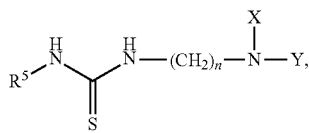

wherein R⁵ represents H, a substituted or unsubstituted alkyl, a substituted or unsubstituted aryl, or a substituted or unsubstituted heteroaryl; X and Y each independently represents one of H, $C_{1-10}$ alkyl, $C_{6-10}$ aryl, $C_{1-10}$ alkyl alcohol, thiohydroxy, carbonyl, sulfonyl, sulfamoyl, carbamoyl, $C_{1-10}$ alkoxycarbonyl, $C_{1-10}$ alkoxycarbamoyl, $C_{1-10}$ alkylamino, $C_{1-10}$ alkylsulfonyl, $C_{1-10}$ haloalkylsulfonyl, ureido, amido and $C_{1-10}$ alkoxylcarbamoyl; and n is 0, 1, 2, 3, 4 or 5, wherein the method includes Reaction Scheme 1 shown below:

Reaction Scheme 1

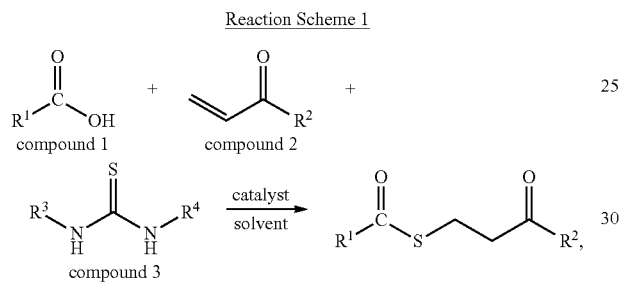

wherein $R^1$, $R^2$, $R^3$, and $R^4$ is one group selected from the group consisting of H, a substituted or unsubstituted alkyl, a substituted or unsubstituted alkoxy, a substituted or unsubstituted aryl, or a substituted or unsubstituted heteroaryl, and the catalyst in Reaction Scheme 1 is the compound represented by Formula I.

2. The method as in claim 1, wherein molar ratio of compound 1:compound 2:compound 3:catalyst is 1-1.5:1-1.5:1-1.5:0.1-0.5.

3. The method as in claim 1, wherein one or more substituents of the substituted alkyl, the substituted alkoxy, the substituted aryl, and the substituted heteroaryl is selected from the group consisting of: a halogen atom, a hydroxyl, a cyano, a nitro, a thiohydroxy, an amino, a carbonyl, a carbamoyl, a sulfamoyl, a $C_{1-20}$ alkyl, a $C_2-C_{20}$ alkenyl, a $C_2-C_{20}$ alkynyl, a $C_1-C_{20}$ alkoxy, $C_{1-20}$ alkyl alcohol, $C_{1-20}$ haloalkyl, $C_{1-20}$ haloalkylthio, $C_{1-4}$ alkylamino, $C_{1-20}$ alkylamido, $C_{1-20}$ alkylsulfonyl, $C_{1-20}$ haloalkylsulfonyl, $C_{1-20}$ alkoxycarbonyl, $C_{1-20}$ alkylcarbamoyl, $C_{6-10}$ aryl, $C_{4-9}$ cycloalkyl, $C_{4-9}$ heteroaryl, and $C_{4-9}$ heterocycloalkyl.

4. The method as in claim 1, wherein $R^1$ represents a substituted or unsubstituted alkyl or a substituted or unsubstituted aryl;

$R^2$ represents a substituted or unsubstituted alkyl, a substituted or unsubstituted alkoxy, or a substituted or unsubstituted aryl;

$R^3$ and $R^4$ each independently represents a substituted or unsubstituted alkyl or a substituted or unsubstituted aryl.

\* \* \* \* \*